US 6,748,334 B1

(12) United States Patent
Perez et al.

(10) Patent No.: US 6,748,334 B1
(45) Date of Patent: Jun. 8, 2004

(54) SPECIALTY GAS ANALYSIS SYSTEM

(76) Inventors: Jorge E. Perez, 1937 Lakeview Rd., SW, Albuquerque, NM (US) 87105; Richard T. Meyer, 9201 Preston Trail, NE, Albuquerque, NM (US) 87111

( * ) Notice: Subject to any disclaimer, the term of this patent is extended or adjusted under 35 U.S.C. 154(b) by 0 days.

(21) Appl. No.: 09/731,550

(22) Filed: Dec. 6, 2000

Related U.S. Application Data
(60) Provisional application No. 60/169,335, filed on Dec. 6, 1999.

(51) Int. Cl.[7] ........................... G01N 31/00; G06F 19/00
(52) U.S. Cl. ....................................................... 702/24
(58) Field of Search ............................. 702/24, 23, 22, 702/31; 7/23.2, 23.36, 23.37; 250/339.03, 339.08, 339.11, 339.13, 339.12

(56) References Cited

U.S. PATENT DOCUMENTS

| | | | | |
|---|---|---|---|---|
| 5,039,614 A | * | 8/1991 | Dekmezian et al. | 436/43 |
| 5,473,162 A | * | 12/1995 | Busch et al. | 250/341.6 |
| 5,572,125 A | * | 11/1996 | Dunkel | 324/307 |
| 5,790,250 A | * | 8/1998 | Wang et al. | 356/451 |
| 5,793,042 A | * | 8/1998 | Quick | 250/339.08 |
| 5,838,008 A | * | 11/1998 | Esler et al. | 250/339.08 |
| 5,968,587 A | * | 10/1999 | Frankel | 427/8 |
| 5,982,486 A | * | 11/1999 | Wang | 356/451 |
| RE36,529 E | | 1/2000 | Lewis et al. | 356/456 |
| 6,049,727 A | * | 4/2000 | Crothall | 600/310 |
| 6,049,762 A | * | 4/2000 | Ganz et al. | 702/104 |
| 6,072,576 A | * | 6/2000 | McDonald et al. | 356/300 |
| 6,110,258 A | * | 8/2000 | Fraenkel et al. | 95/117 |
| 6,208,137 B1 | * | 3/2001 | Sardashti et al. | 324/306 |
| 6,225,061 B1 | * | 5/2001 | Becker et al. | 435/6 |
| 6,254,828 B1 | * | 7/2001 | LaCount | 422/78 |
| 6,260,997 B1 | * | 7/2001 | Claybourn et al. | 374/45 |
| 6,284,196 B1 | * | 9/2001 | Casal et al. | 422/62 |
| 6,300,633 B1 | * | 10/2001 | Hunt et al. | 250/339.12 |
| 6,319,565 B1 | * | 11/2001 | Todd et al. | 427/531 |
| 6,343,239 B1 | * | 1/2002 | Toda et al. | 700/121 |
| 6,426,045 B1 | * | 7/2002 | Jeng et al. | 422/82.05 |

OTHER PUBLICATIONS

Haaland, D. "Multivariate Calibration Methods Applied to Quantitative FT–IR Analyses" Practical Fourier Transform Infrared Spectroscopy, 1990. pp. 395–468.

Haaland, D. et al. "Use of CLS to Understand PLS IR Calibration for Trace Detection of Organic Molecules in Water" Applied Spectroscopy, vol. 53, No. 4, 1999. pp. 390–395.

Haaland, D. et al. "Improved Sensitivity of Infrared Spectroscopy by the Application of Least Squares Methods" Applied Spectroscopy, vol. 34, No. 5, 1980. pp. 539–548.

Haaland, D. et al. "Application of New Least–Squares Methods for the Quantitative Infrared Analysis of Multicomponent Samples" Applied Spectroscopy, vol. 35, No. 6, 1982. pp. 665–673.

Griffith, D. "Synthetic Calibration and Quantitative Analysis of Gas–Phase FT–IR Spectra" Applied Spectroscopy, vol. 50, No. 59, 1996. pp. 59–70.

Jaakkola, P. et al. "Instrumental Resolution Considerations for Fourier Transform Infrared Gas–Phase Spectroscopy" Applied Spectroscopy, vol. 51, No. 8, 1997. pp. 1159–1169.

Esler, M. et al. "Precision Trace Gas Analysis by FT–IR Spectroscopy. 1. Simultaneous Analysis of CO2, CH4, N2O and CO in Air" Analytical Chemistry, vol. 72, No. 1, 2000. pp. 206–215.

Esler, M. et al. "Precision Trace Gas Analysis by FT01R Spectroscopy. 2. The 13C/12C Isotope Ratio of CO2" Analytical Chemistry, vol. 72, No. 1, 2000. pp. 216–221.

(List continued on next page.)

*Primary Examiner*—John Barlow
*Assistant Examiner*—Demetrius Pretlow

(57) ABSTRACT

A system and method for detection of impurities in gases comprising a Fourier transform infrared spectrometer and computation devices for system control, spectral analysis, and chemometrics.

22 Claims, 39 Drawing Sheets

SYSTEM BLOCK DIAGRAM

OTHER PUBLICATIONS

Haaland, D. et al. "Multivariate Least–Squares Methods Applied to the Quantitative Spectral Analysis of Multicomponent Samples" Applied Spectroscopy, vol. 39, No. 1, 1985. pp. 73–84.

Haaland, D. "Methods to Include Beer's Law Nonlinearities in Quantitative Spectral Analysis" Computerized Quantitative Infrared Analysis, STP vol. 934, 1987. pp. 78–94.

Haaland, D. et al. "Multi–Window Classical Least–Squares Multivariate Calibration Methods for Quantitative ICP–AES Analyses" Applied Spectroscopy, vol. 54, No. 9, 2000. pp. 1291–1302.

Haaland, D. et al. "New Prediction–Augmented Classical Least–Squares (PACLS) Methods: Application to Unmodeled Interferents" Applied Spectroscopy, vol. 54, No. 9, 2000. pp. 1303–1312.

Stallard, B. et al. "Trace Water Vapor Determination in Corrosive Gases by Infrared Spectroscopy" Sandia Report SAND93–4026 (Sandia National Labs, Albuquerque, NM), 1993.

Salomaa, I. et al., "Origin of and Compensation for the Baseline Errors in Fourier Transform Spectra" Applied Spectroscopy, vol.52, No. 4, 1998. pp. 579–586.

Meyer, R.T., Turnkey Industrial Instrumentation for Fast–response, On–line Analysis of PPB Impuritites in the Electronic Semiconductor Gases, Jul. 2000, Electronic Optics, Optical Sensing in Semiconductor Manufacturing, pp. II33–II34.*

* cited by examiner

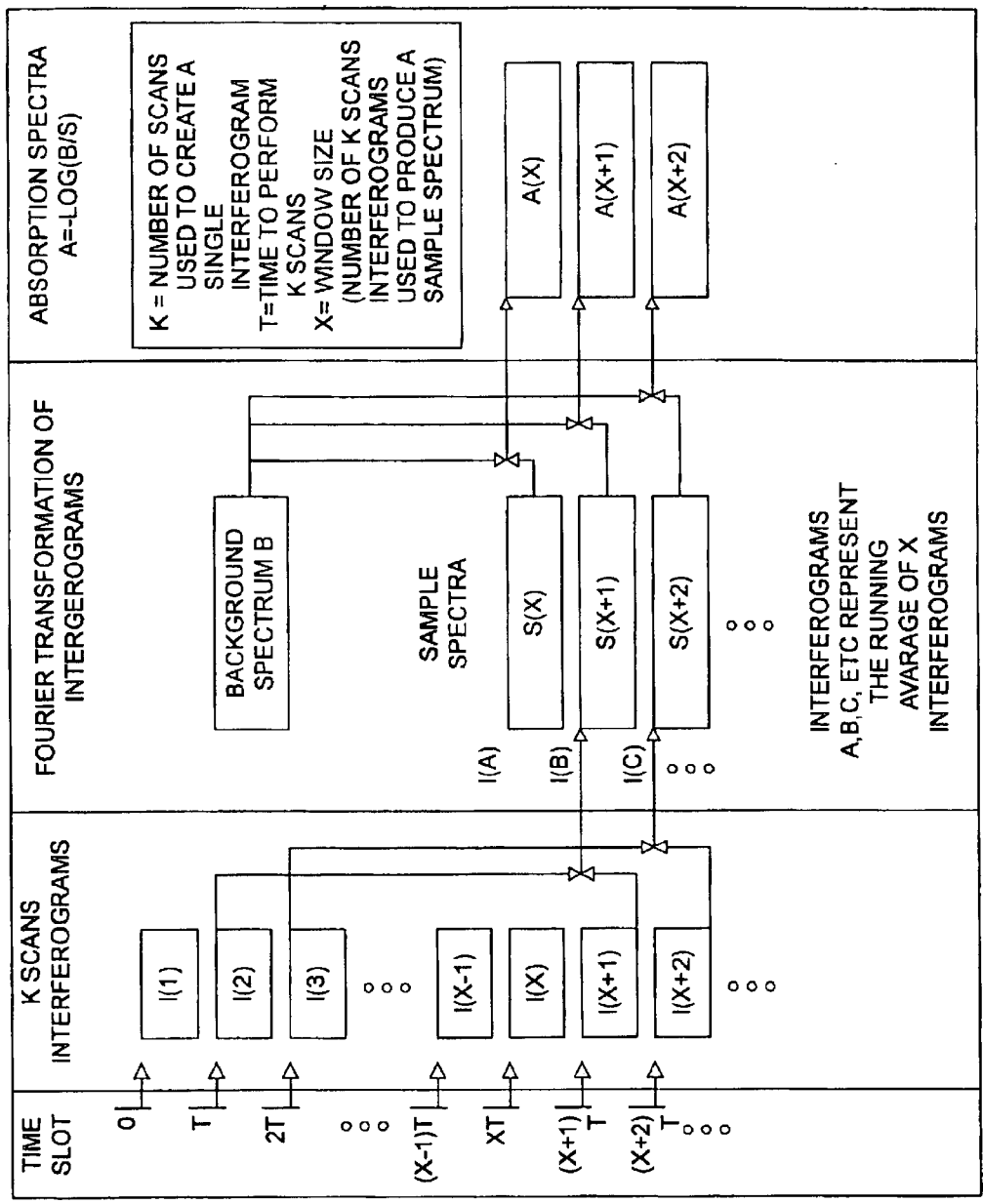
FIG. 1 PROCESS 1 - DATA COLLECTION

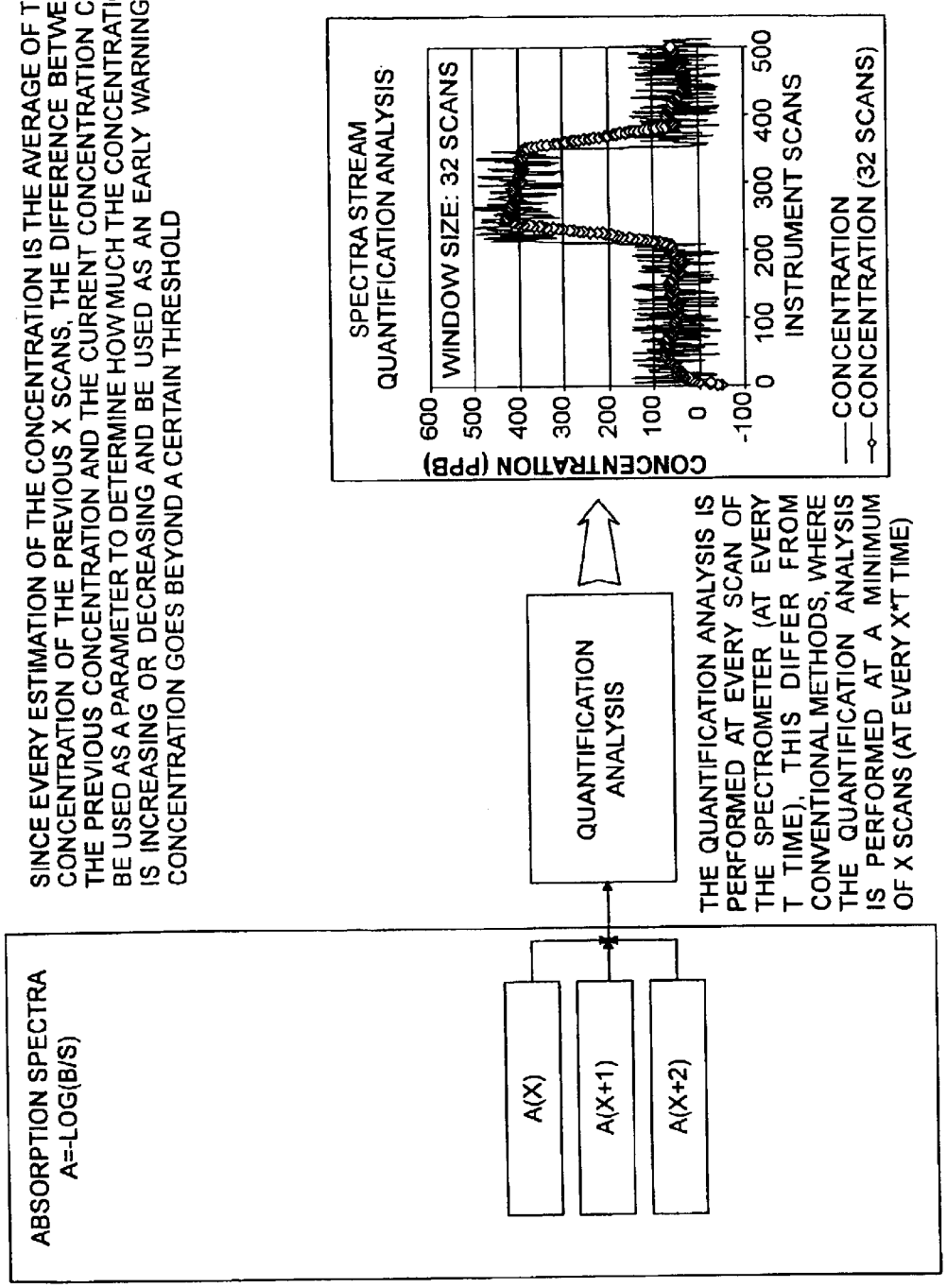
FIG 2 PROCESS 2 - DATA QUANTIFICATION

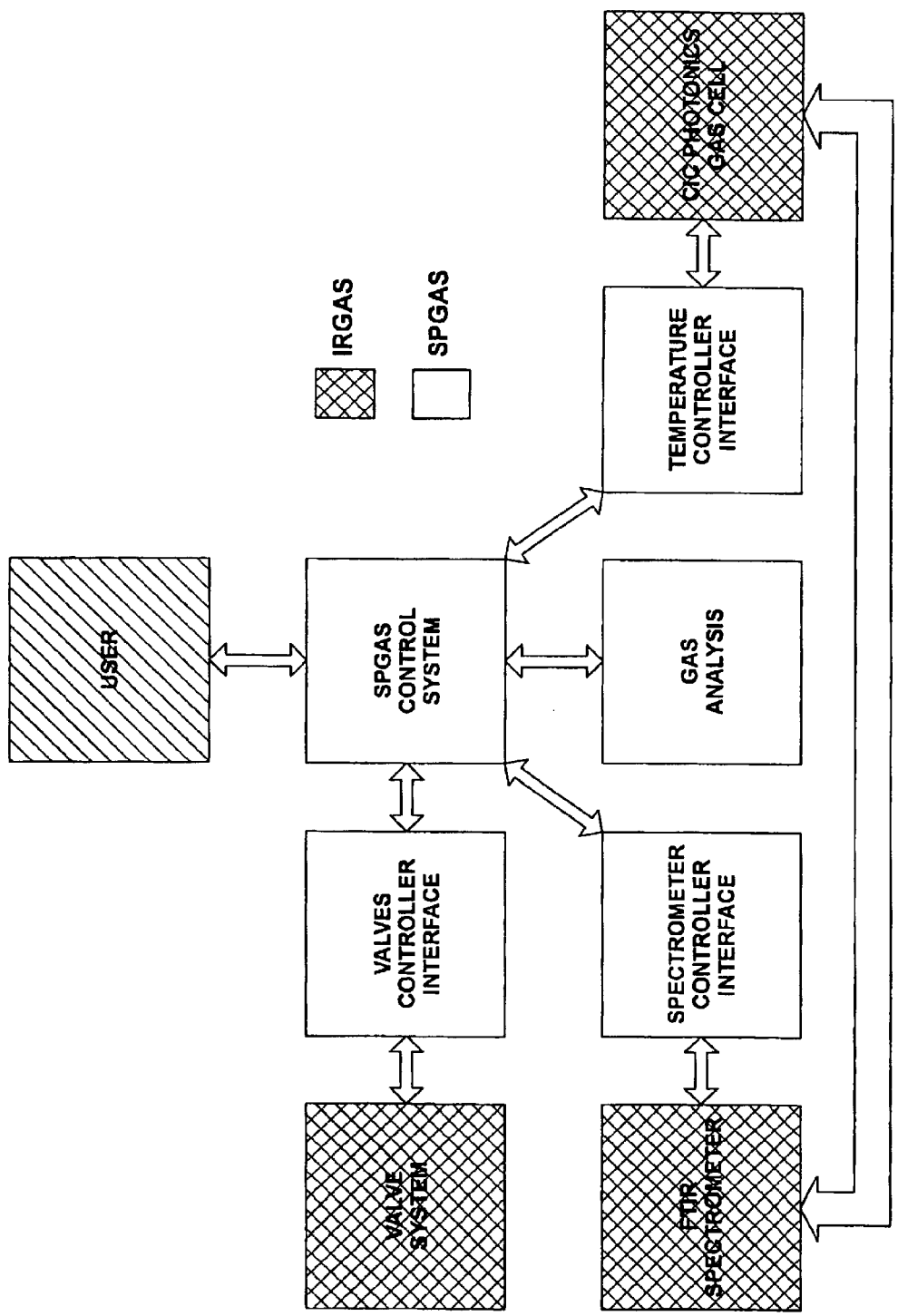
FIG. 3 SYSTEM BLOCK DIAGRAM

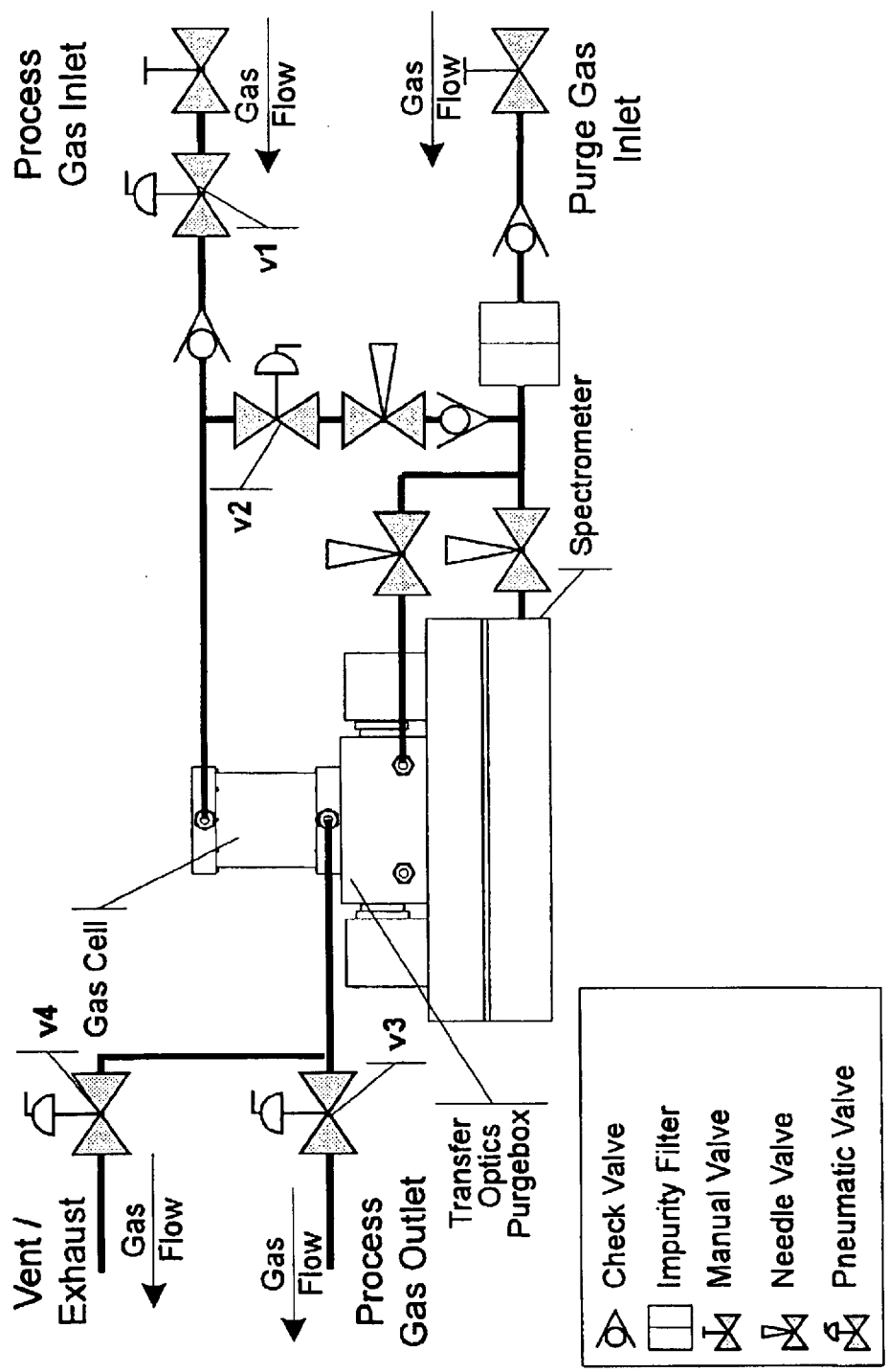
Fig. 4 System Hardware Configuration

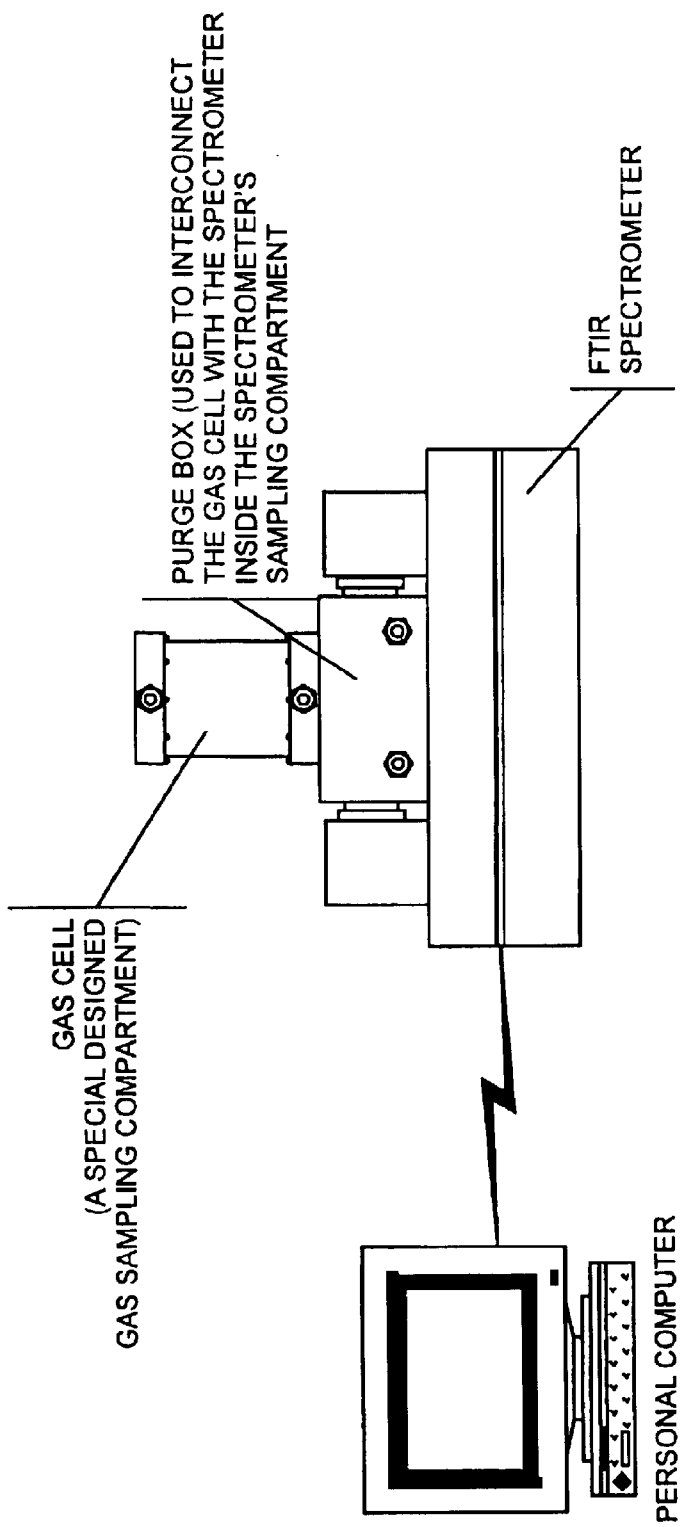
FIG. 5 FTIR SPECTROMETER AND PERSONAL COMPUTER INTERCONNECTION

PROCESS 1
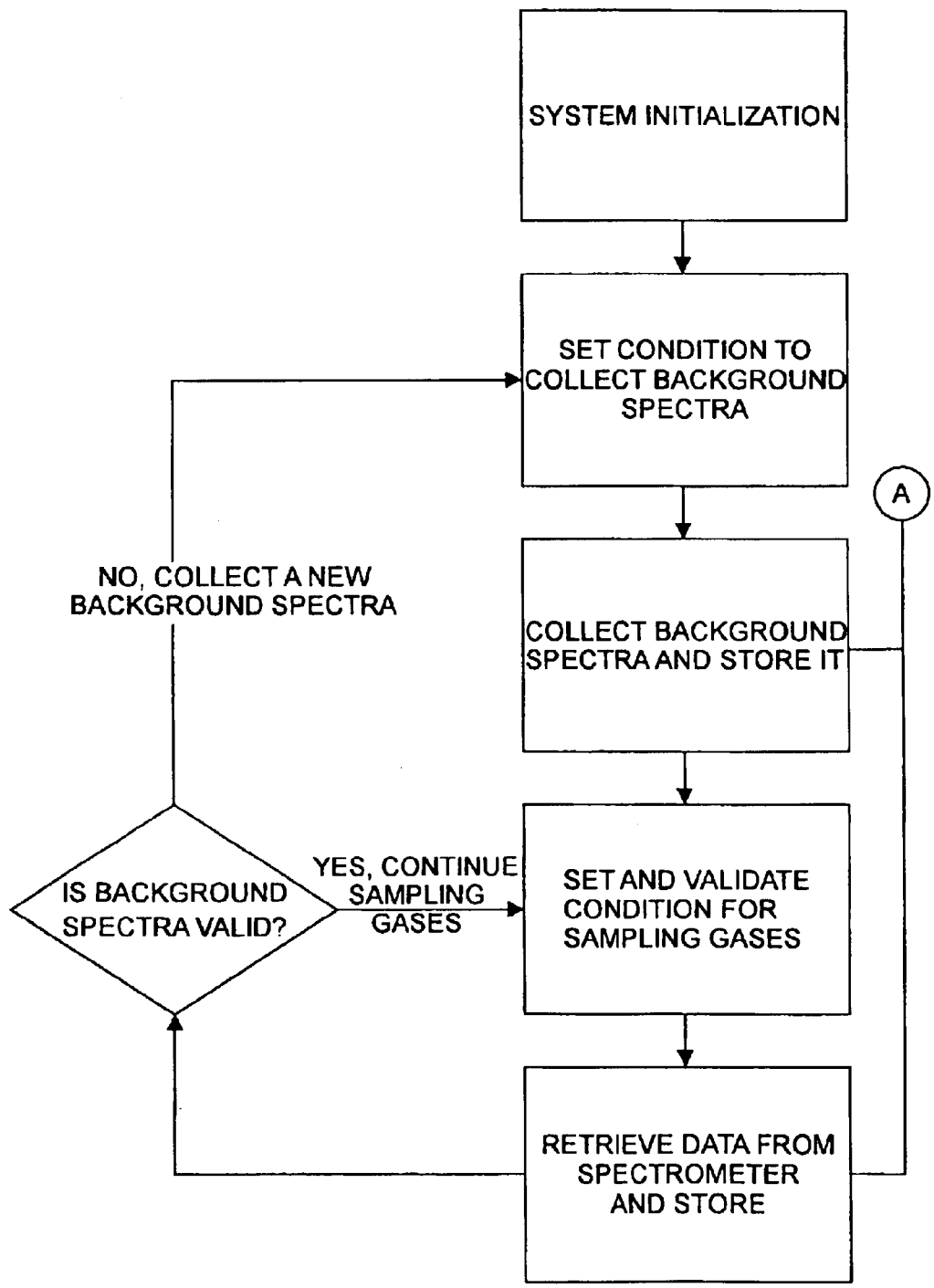
FIG. 6A PROCESS 1 AND 2 BLOCK DIAGRAM

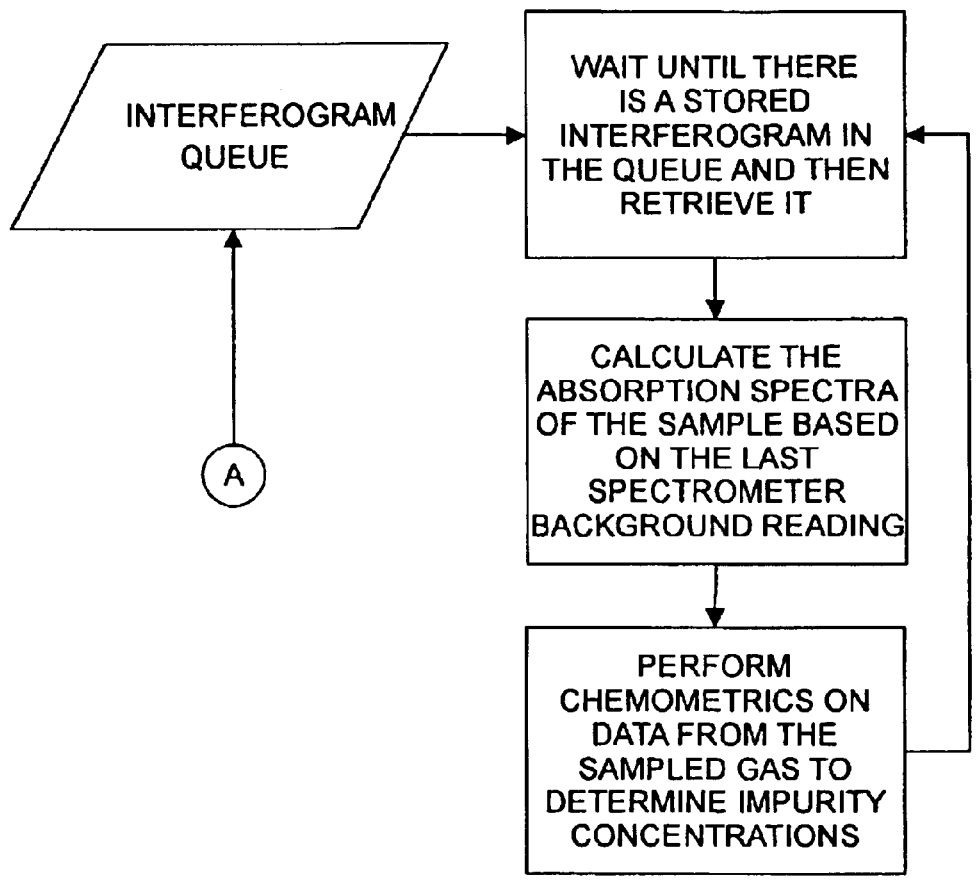
FIG. 6B PROCESS 1 AND 2 BLOCK DIAGRAM

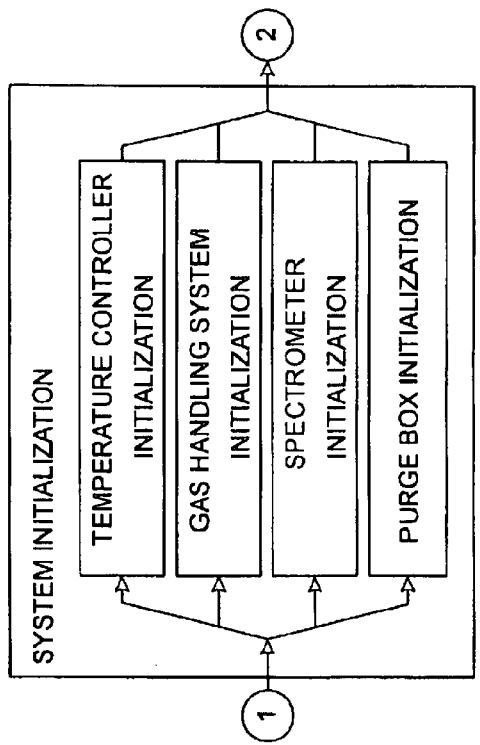
FIG. 7A PROCESS 1 AND SUB-PROCESSES

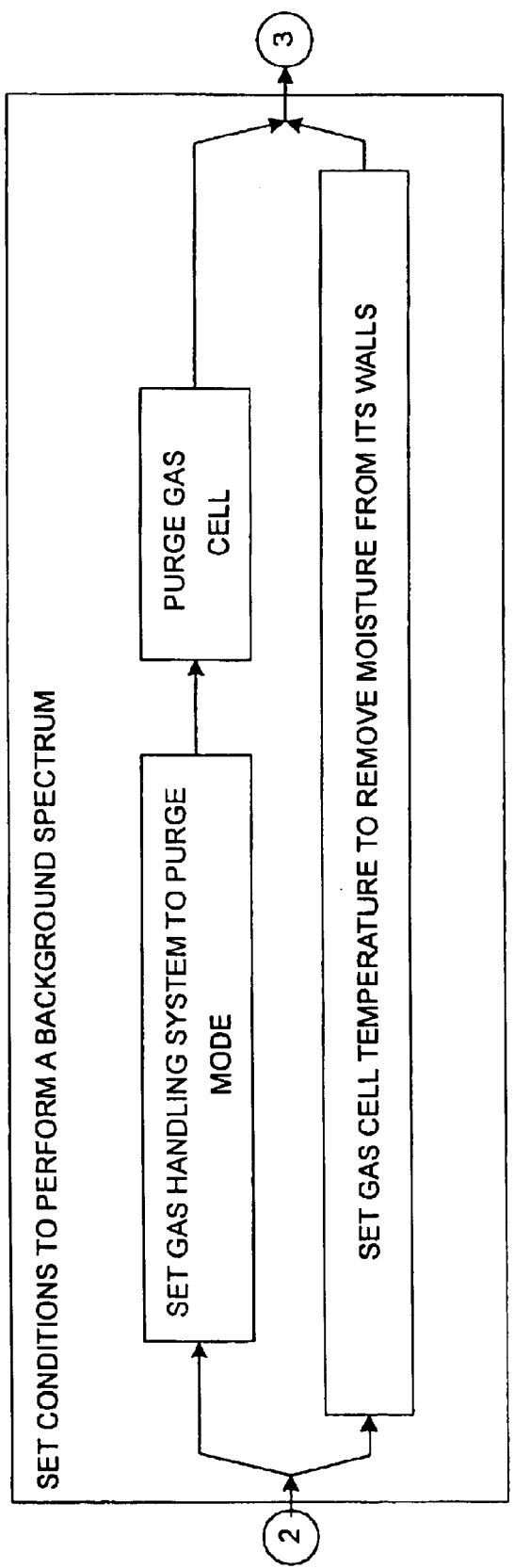
FIG. 7B PROCESS 1 AND SUB-PROCESSES

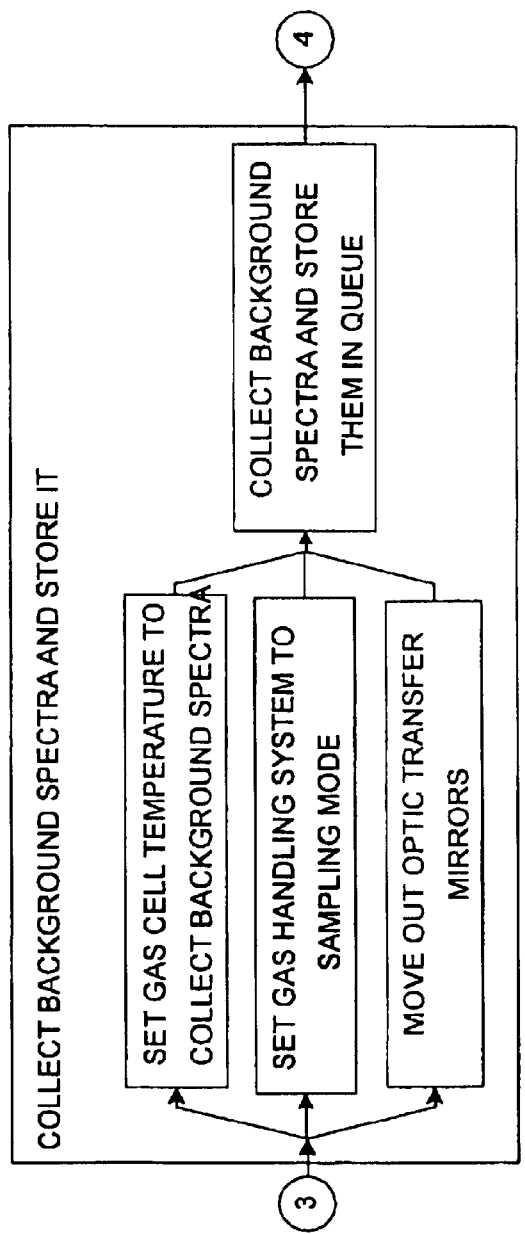
FIG. 7C PROCESS 1 AND SUB-PROCESSES

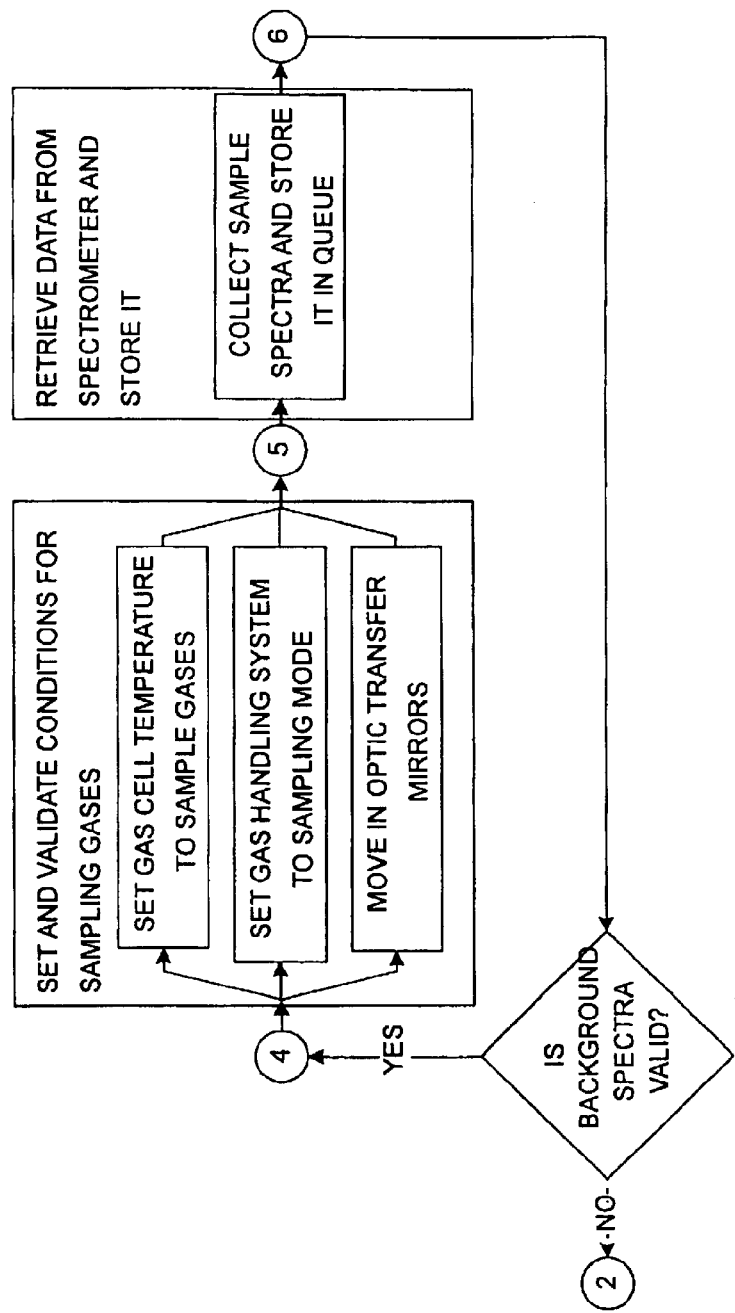
FIG 7D PROCESS 1 AND SUB-PROCESSES

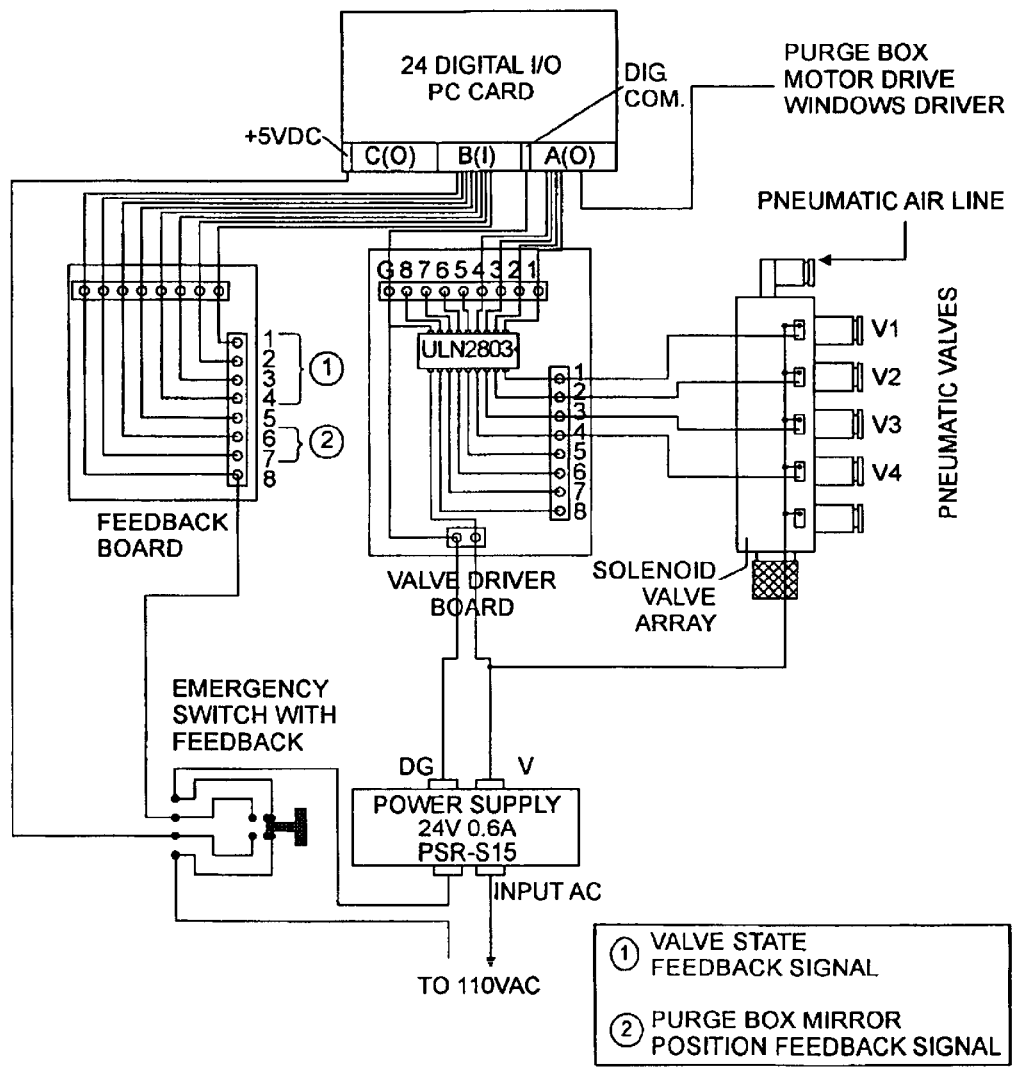
FIG. 8 GAS HANDLING SYSTEM HARDWARE DRIVER

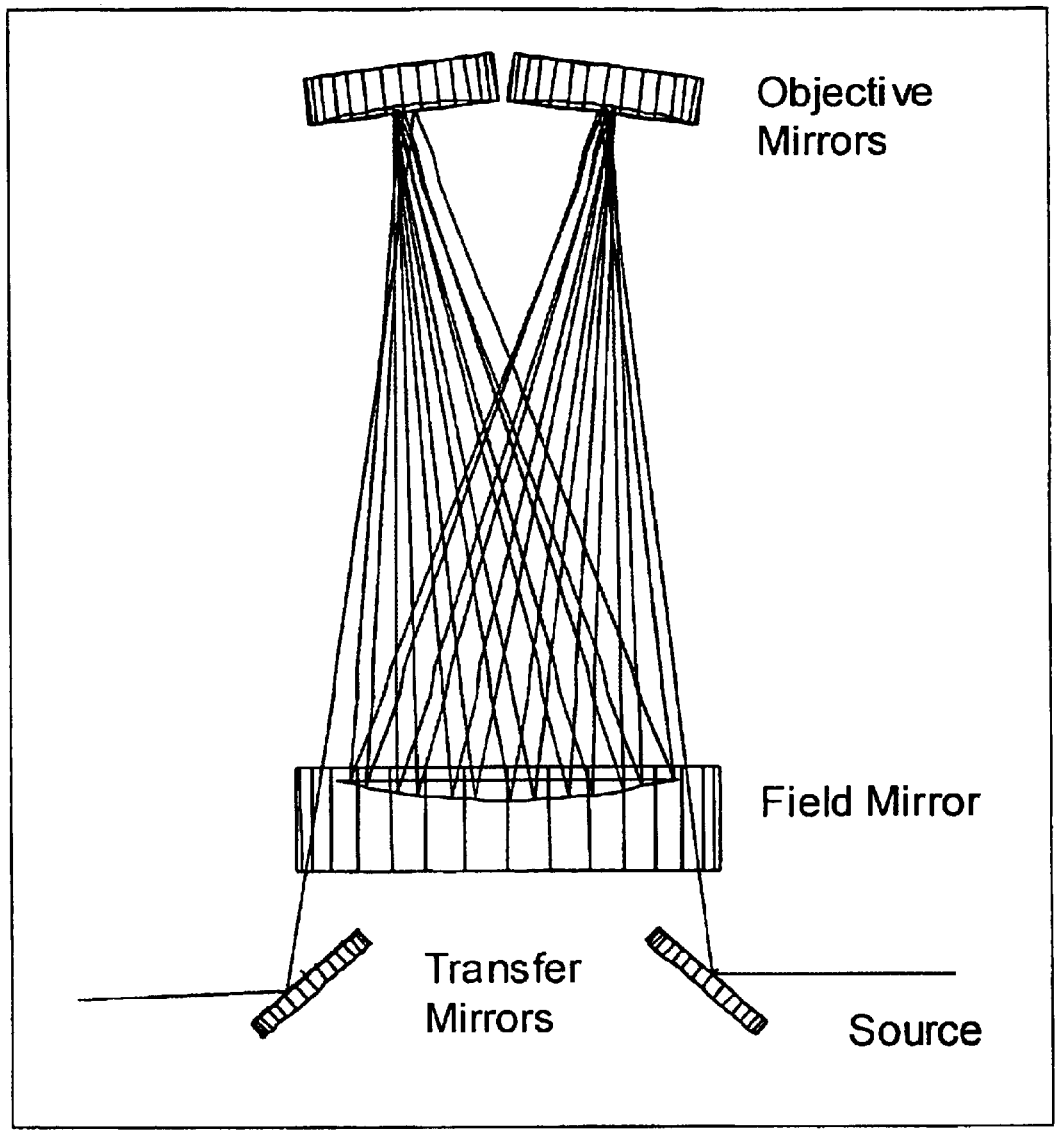
FIG. 9 WHITE CELL DESIGN

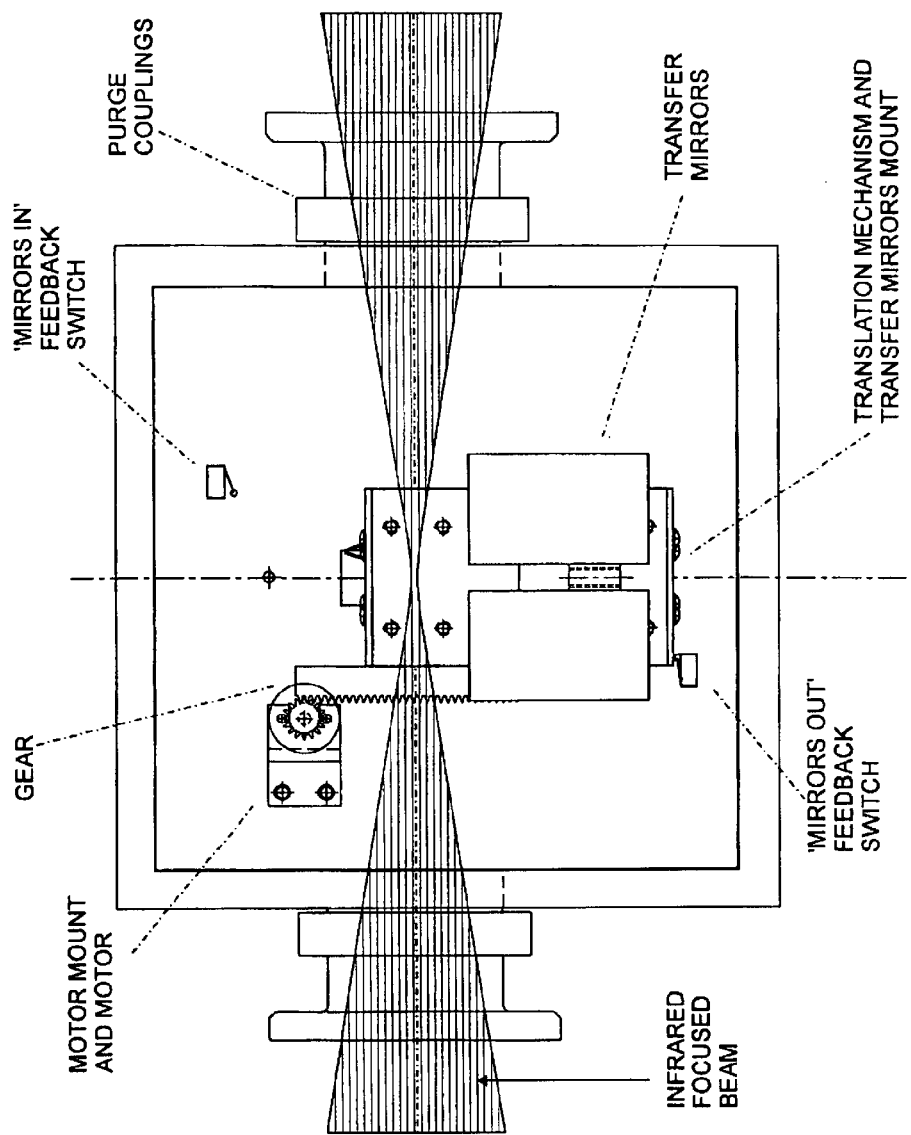
FIG. 10 PURGE BOX 'MIRRORS OUT' POSITION

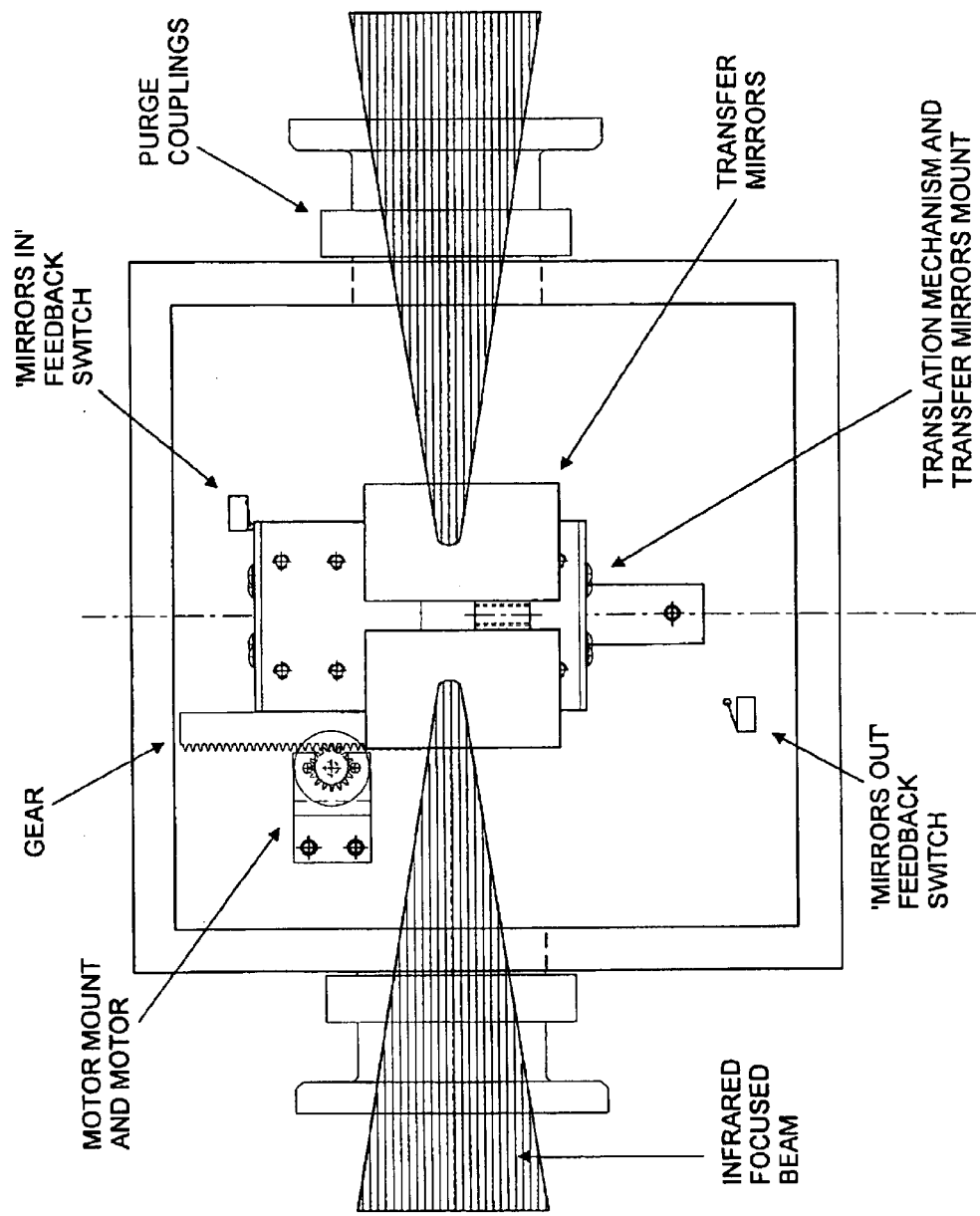
FIG 11 PURGE BOX 'MIRRORS IN' POSITION

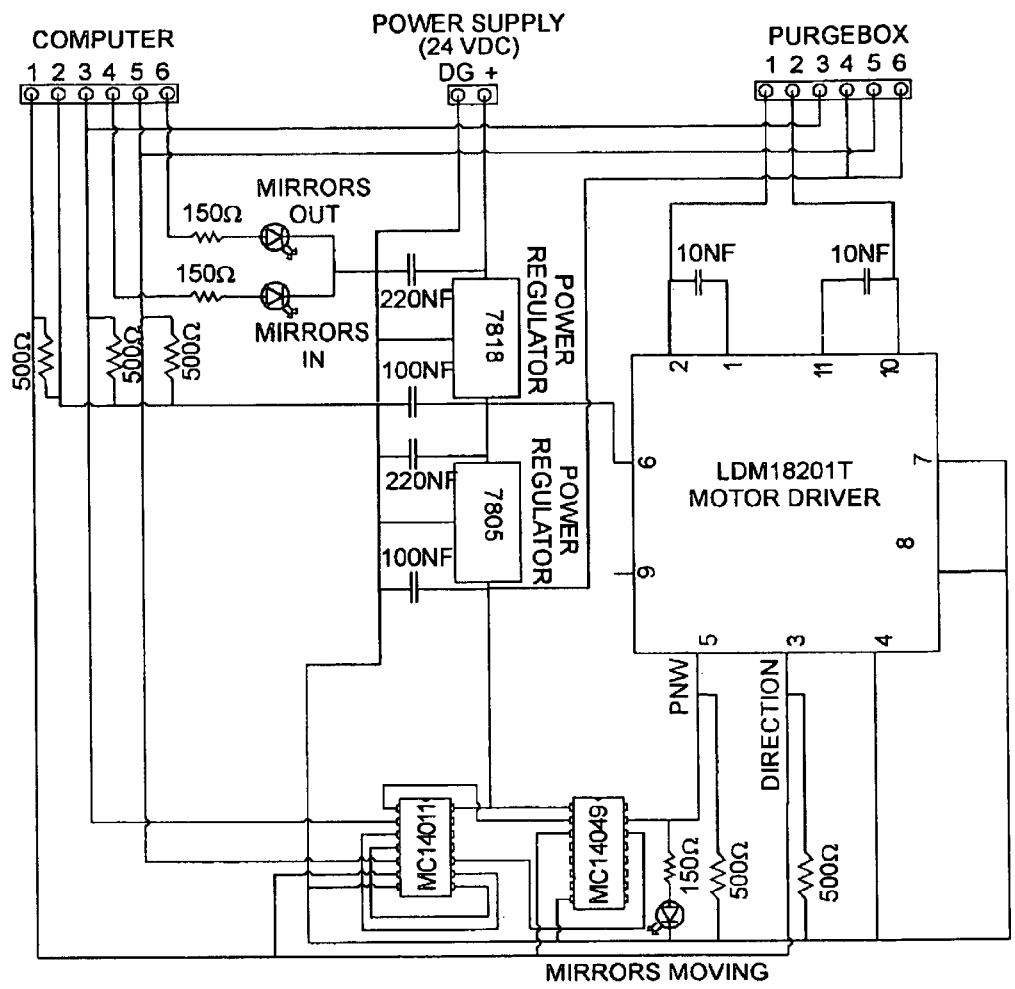
FIG. 12 PURGE BOX DC MOTOR HARDWARE DRIVER

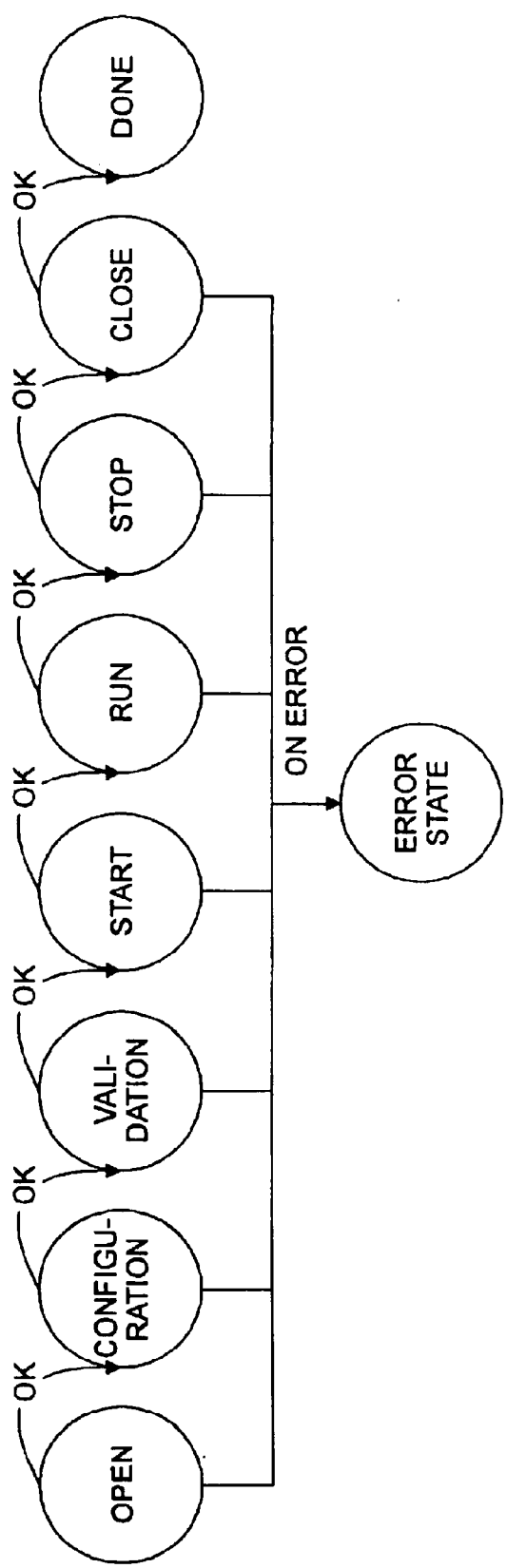
FIG 13 TINSTRUMENT STATE DIAGRAM

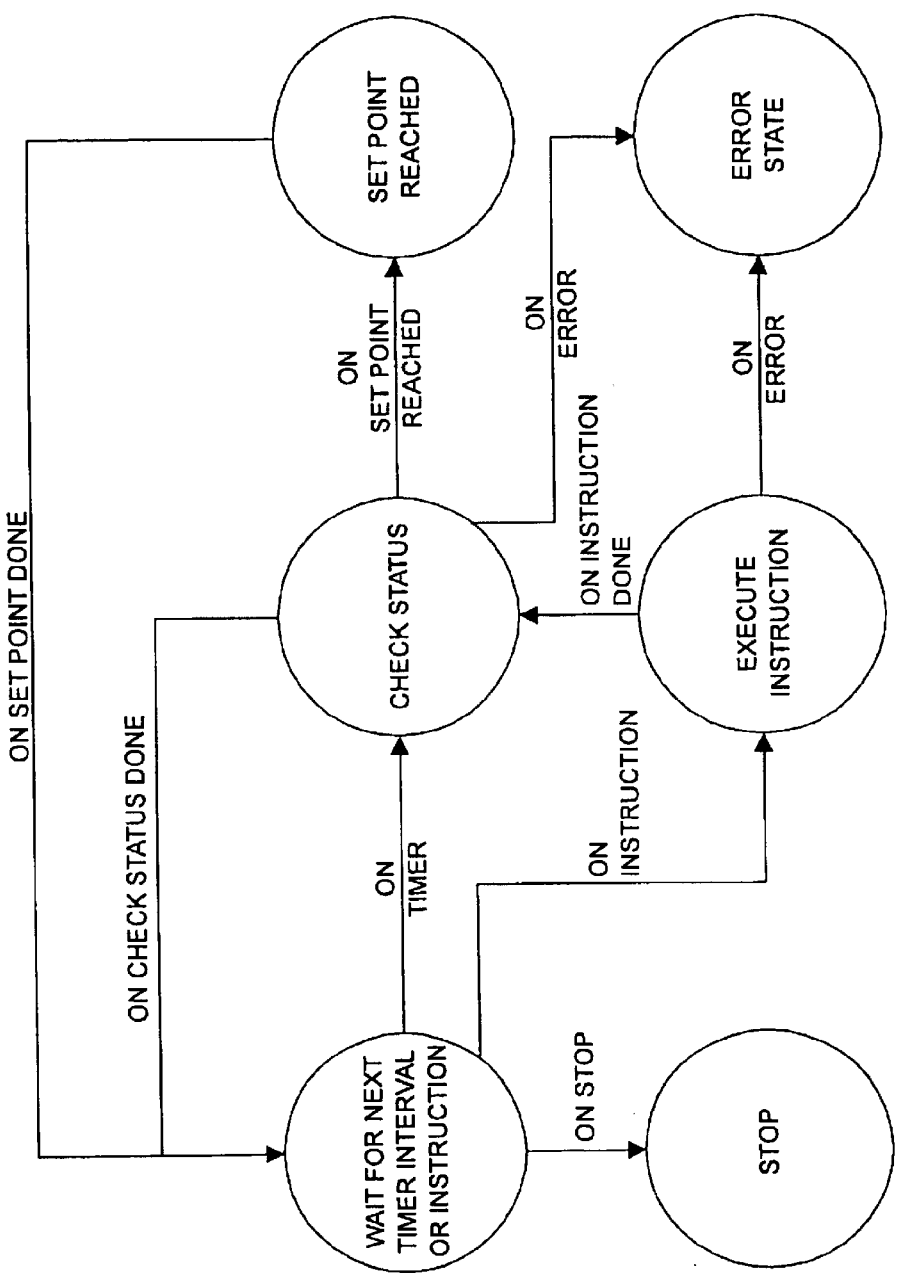
FIG. 14 RUN STATE DIAGRAM

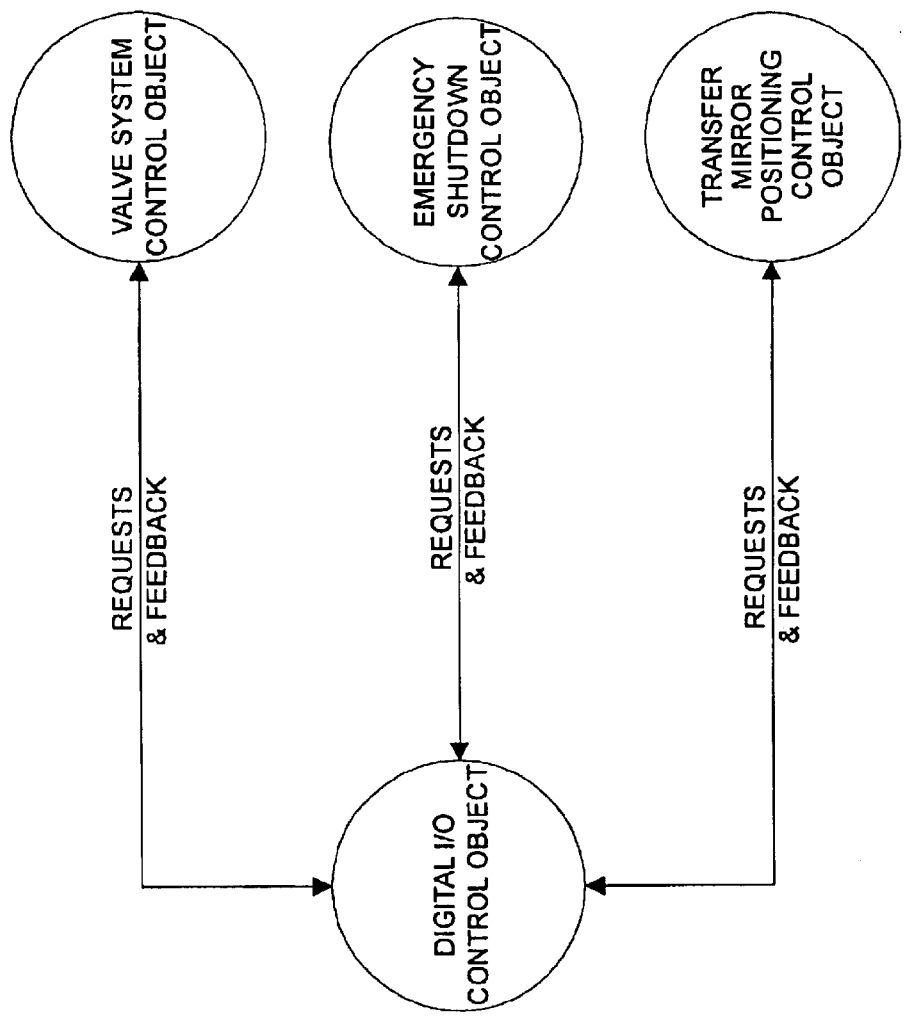
FIG. 15 DIGITAL I/O CONTROLLER INTERACTION WITH OTHER CONTROLLERS

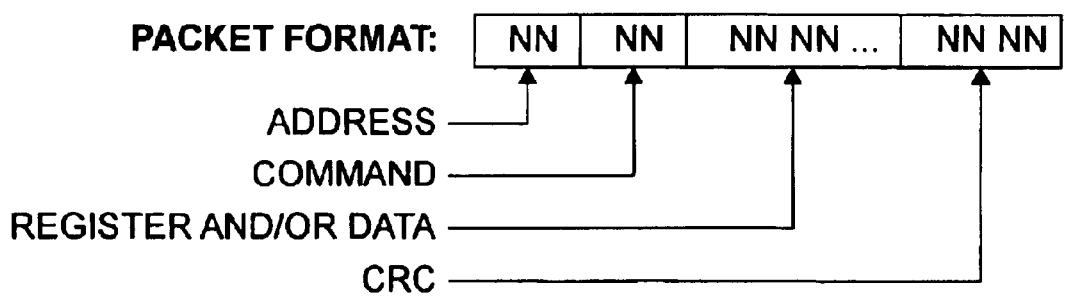
FIG. 16 CONTROLLER PACKET FORMAT

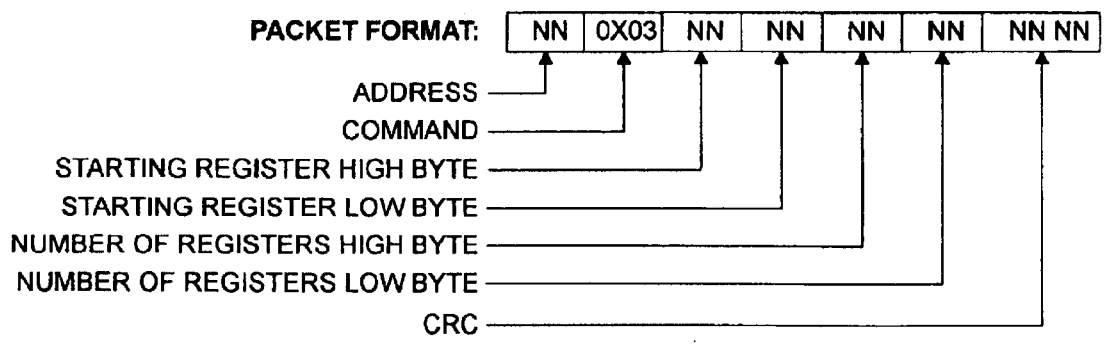
FIG. 17 READ COMMAND DATA FORMAT

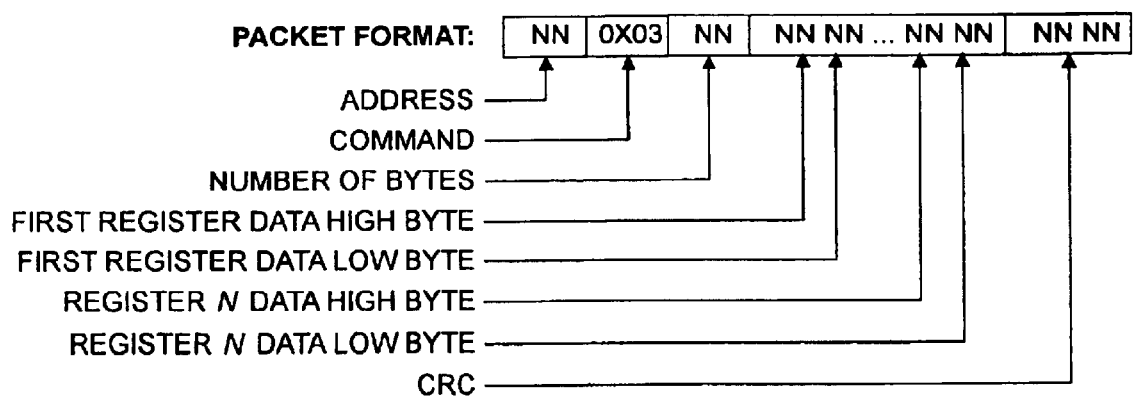
FIG. 18 RESPOND TO A READ COMMAND DATA FORMAT

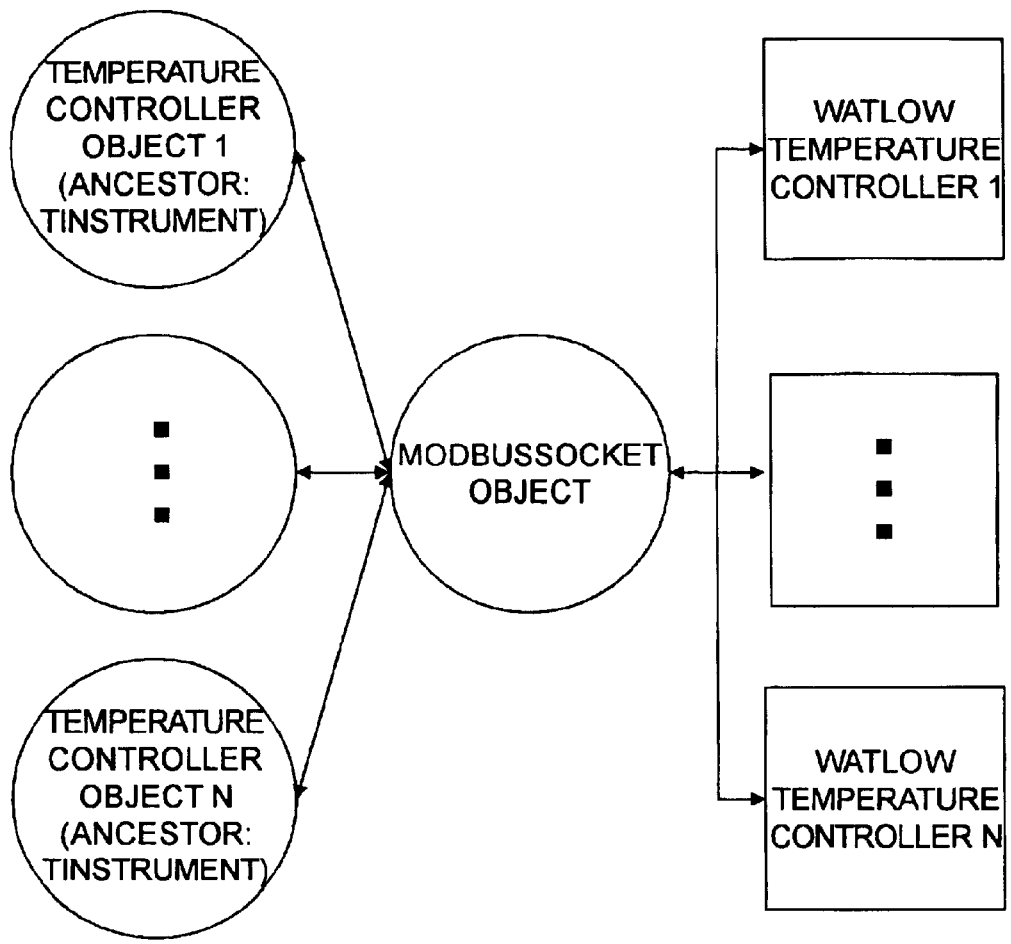
FIG. 19 MODBUSSOCKET INTERACTION BLOCK DIAGRAM

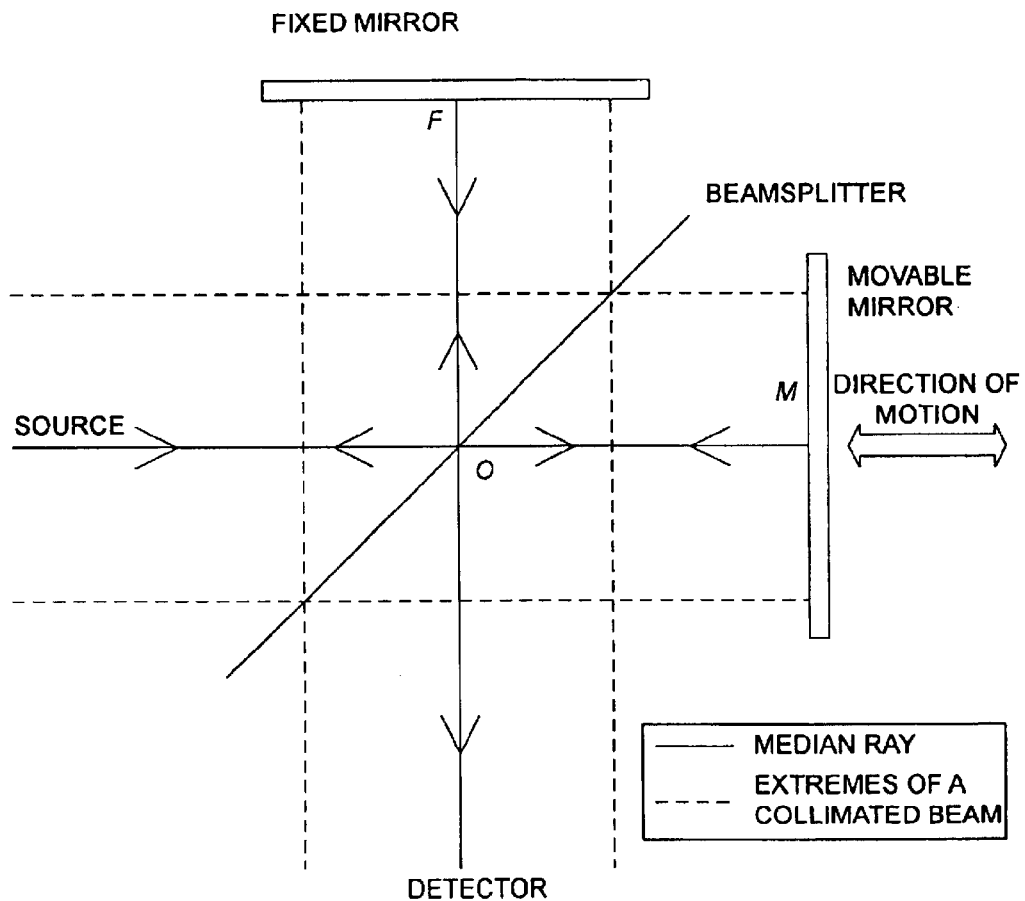
FIG. 20 SHCEMETIC REPRESENTATION OF A MICHELSON INTERFEROMETER.

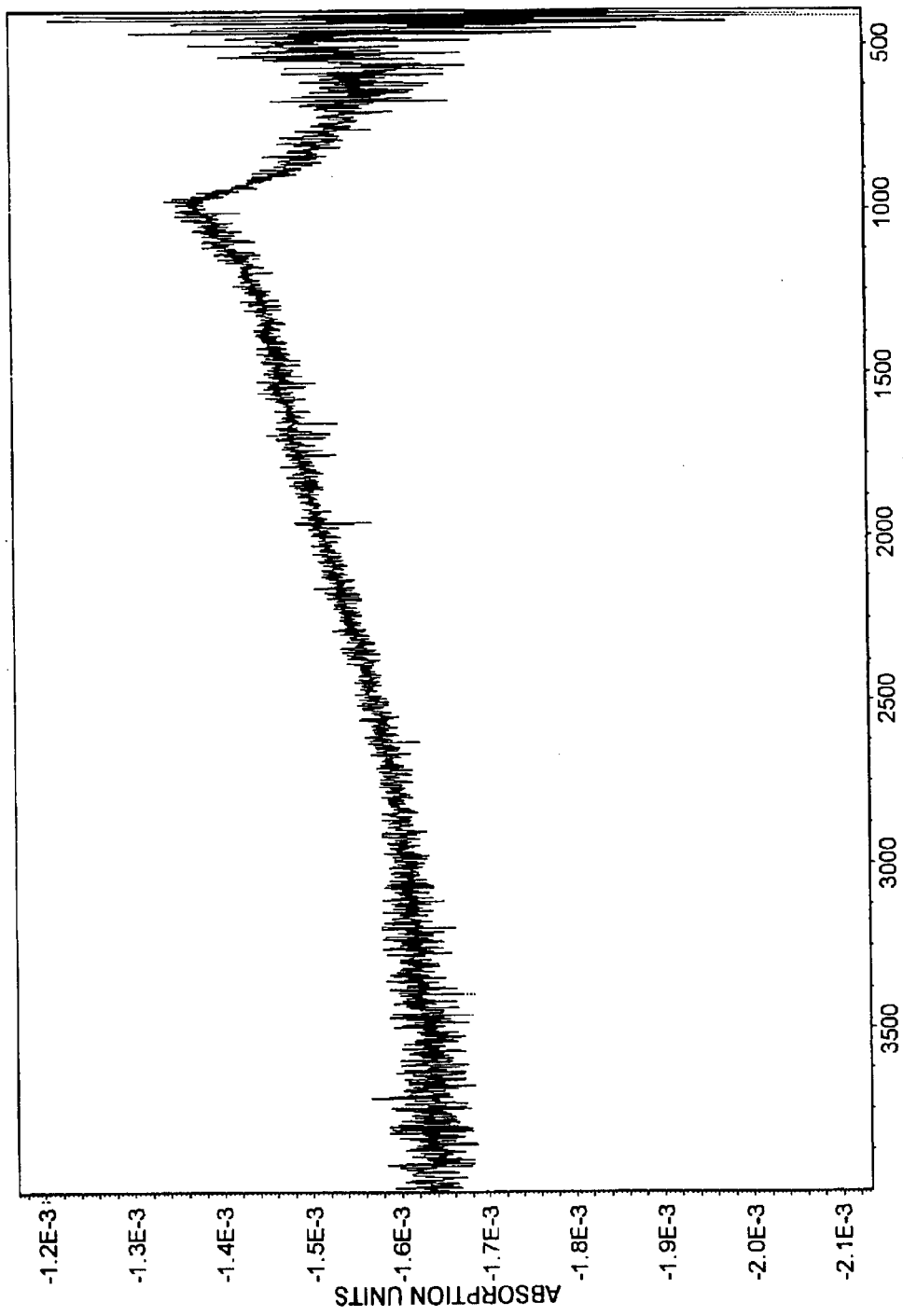
FIG. 21 SYSTEM BASELINE AFTER COLLECTING A LONG BACKGROUND AND SAMPLE SPECTRA

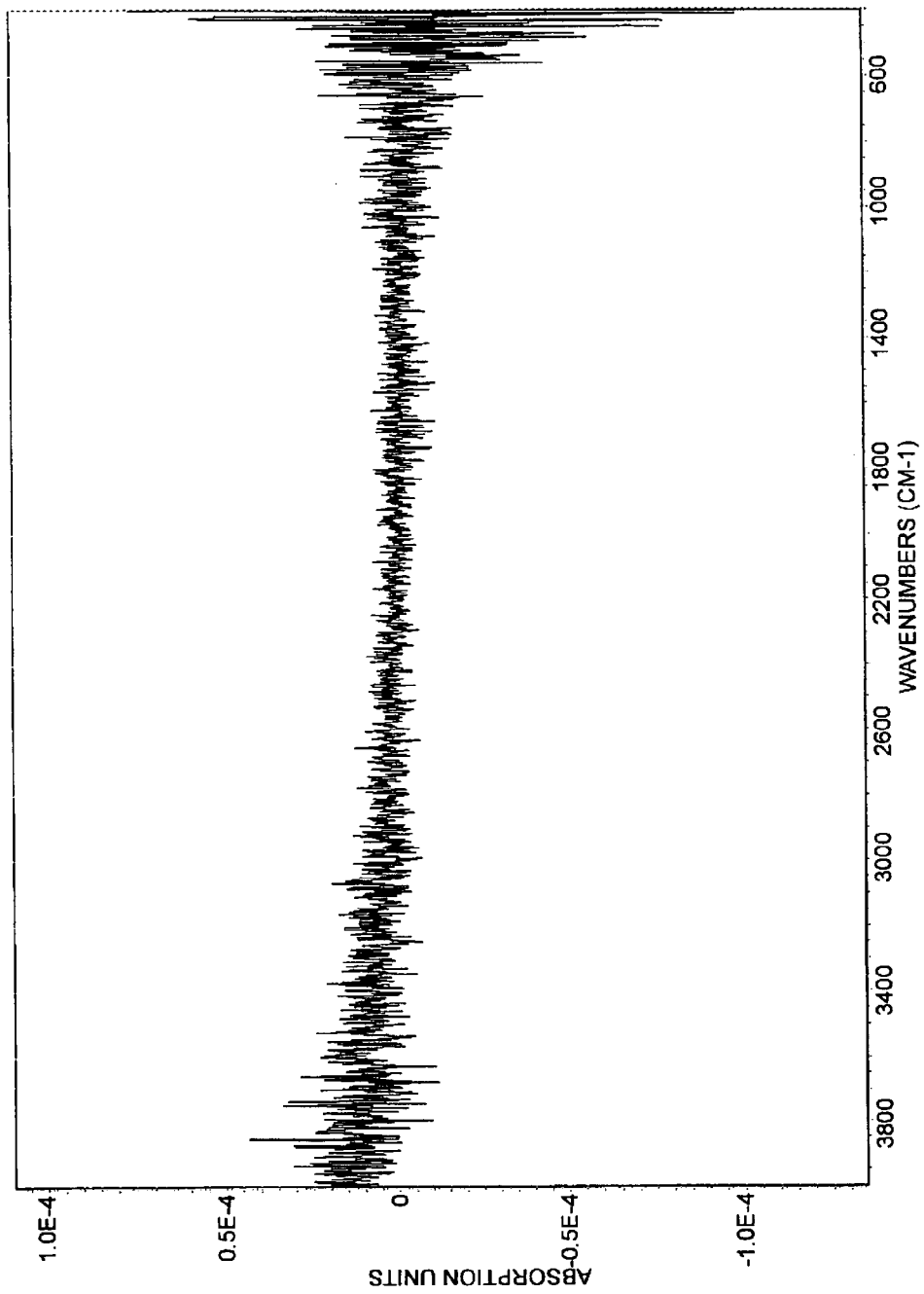
FIG. 22 SYSTEM BASELINE USING SPECTRASTREAM

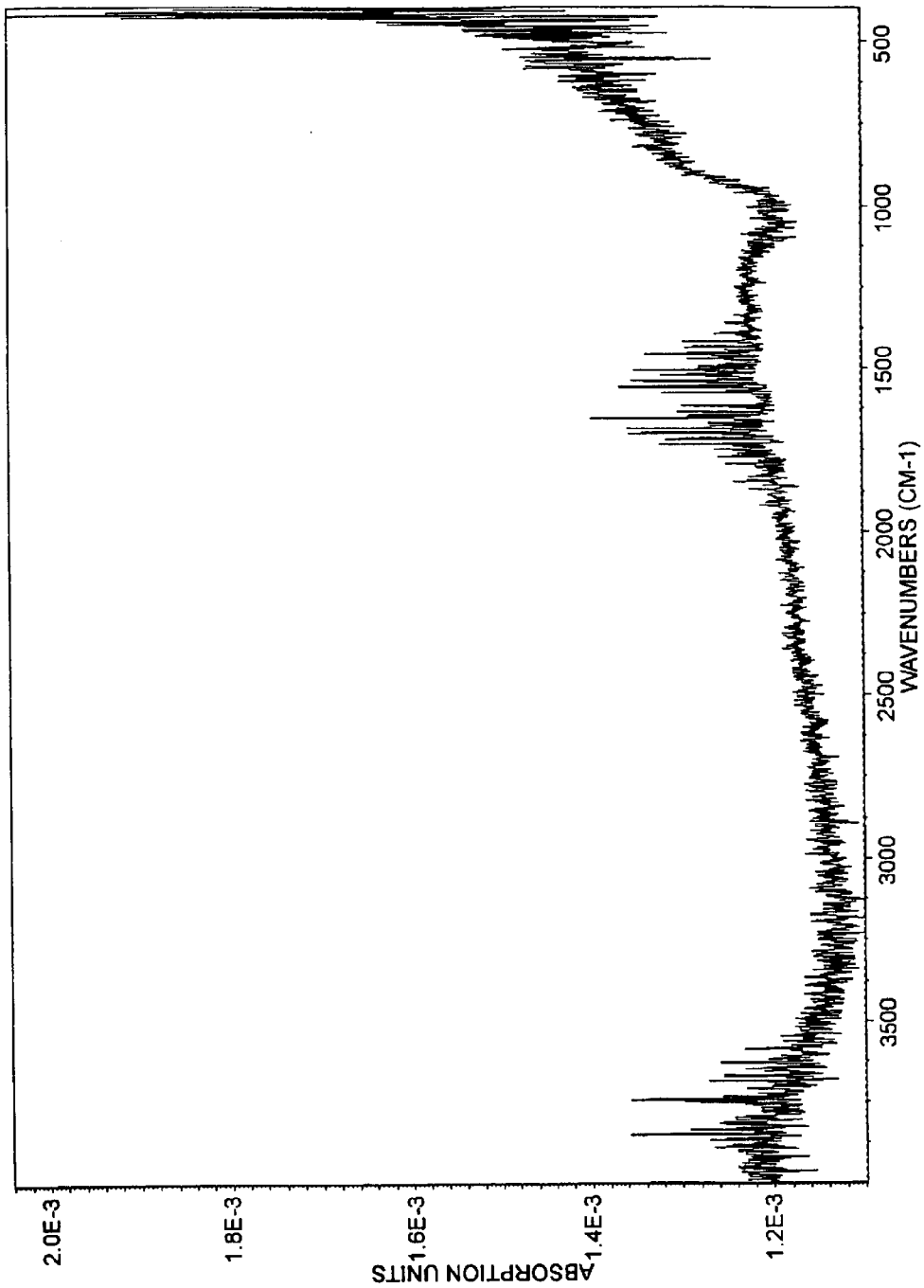
FIG. 23 CONVENTIONAL BASELINE COLLECTION WITH LOW FLOW RATE PURGING

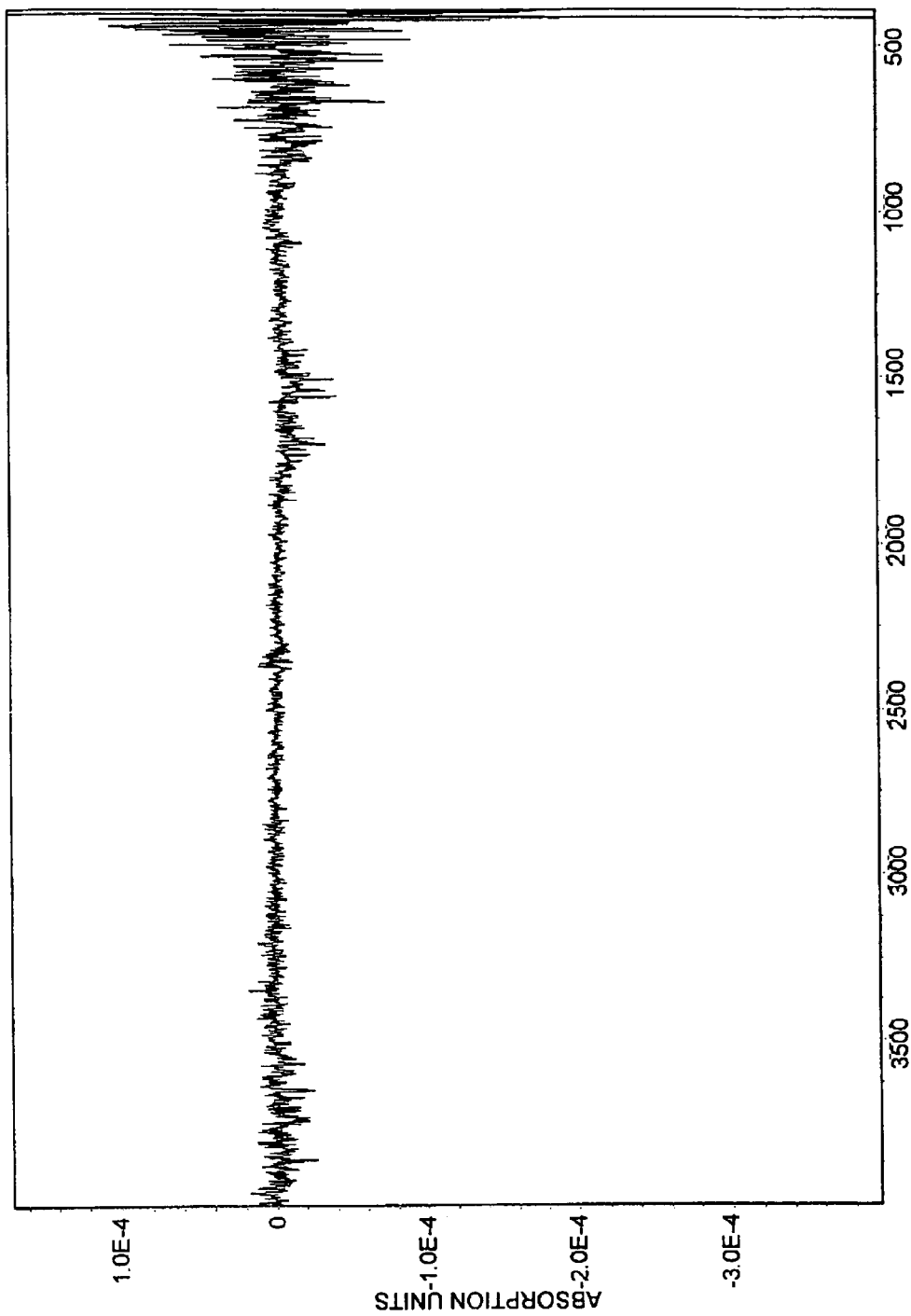
FIG 24 SYSTEM BASELINE USING SPECTRASTREAM WITH NO SYSTEM PURGING AT ALL

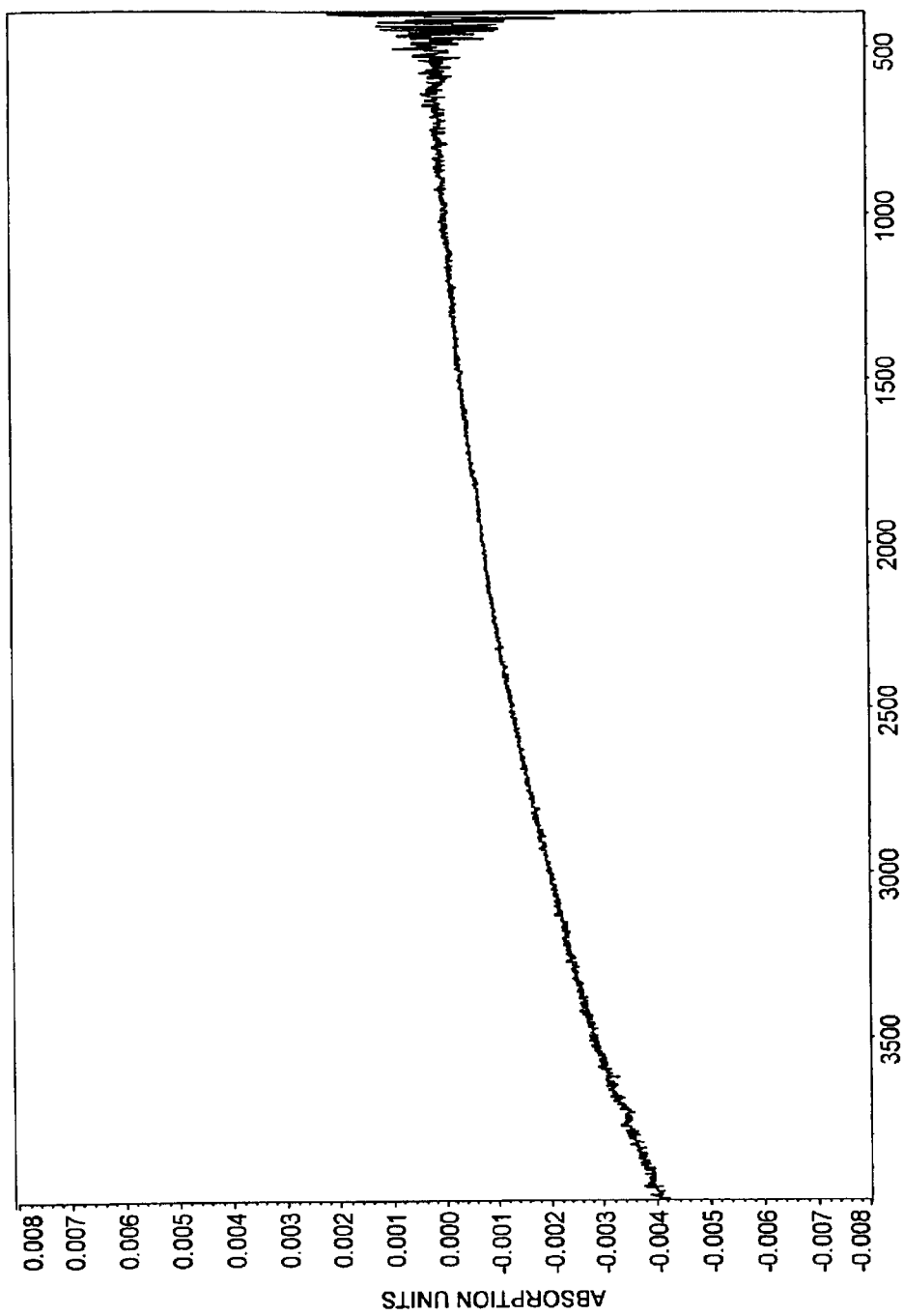
FIG 25 GAS CELL BASELINE SPECTRUM MINUS SAMPLE SPECTRA

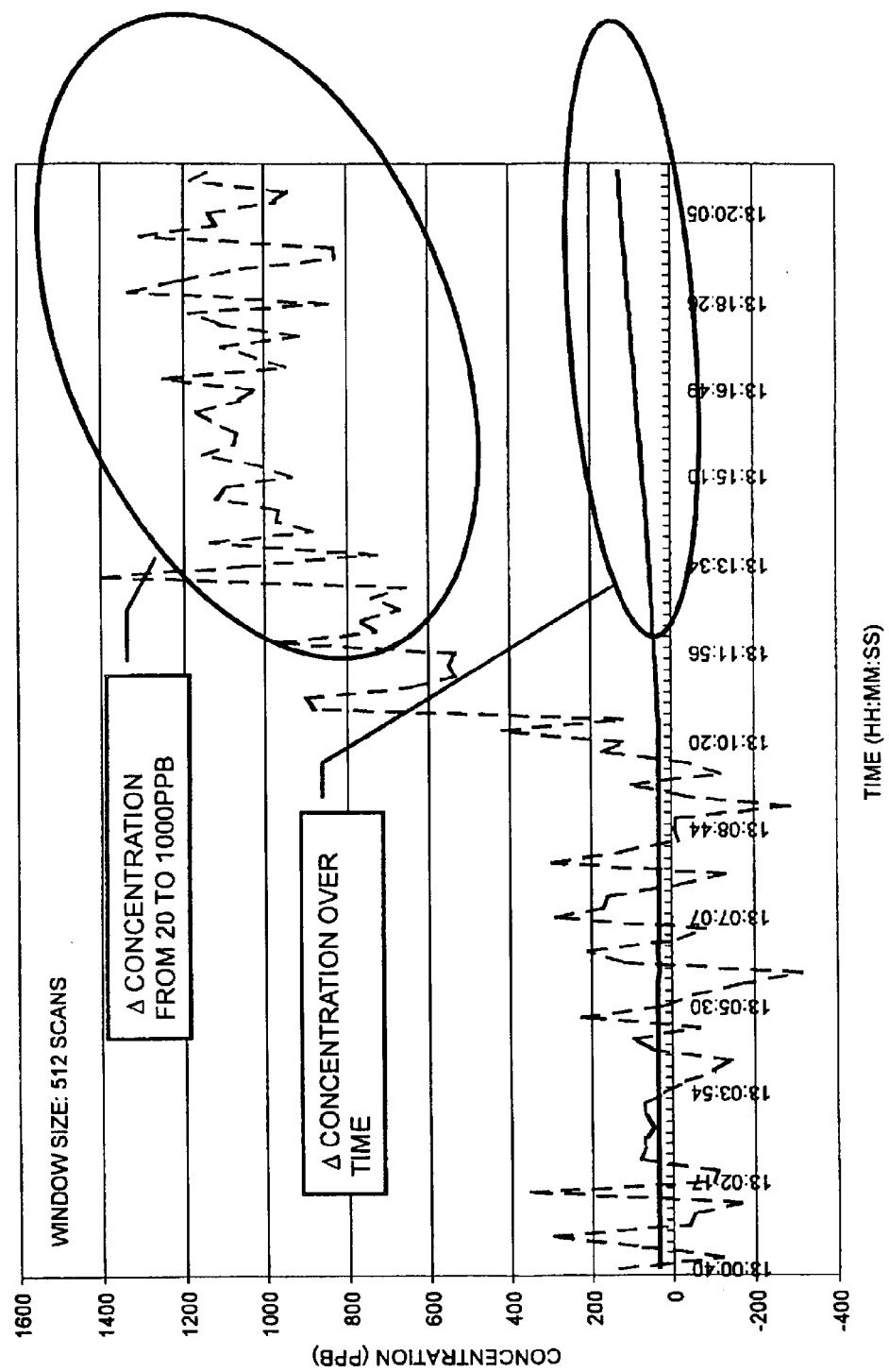
FIG. 26 MOISTURE DETECTION ANALYSIS

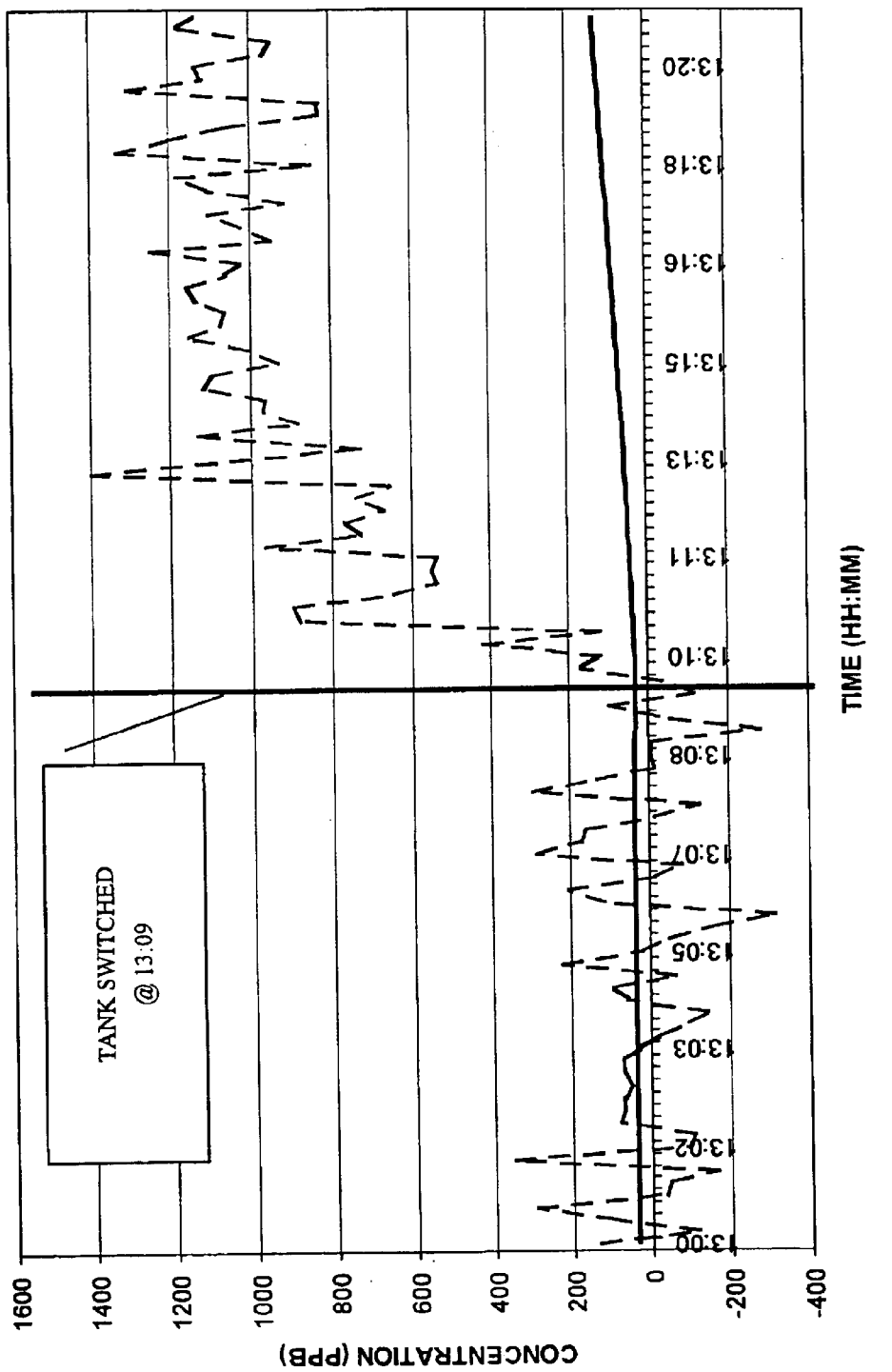
FIG. 27 DETECTION OF CH4 (METANE)

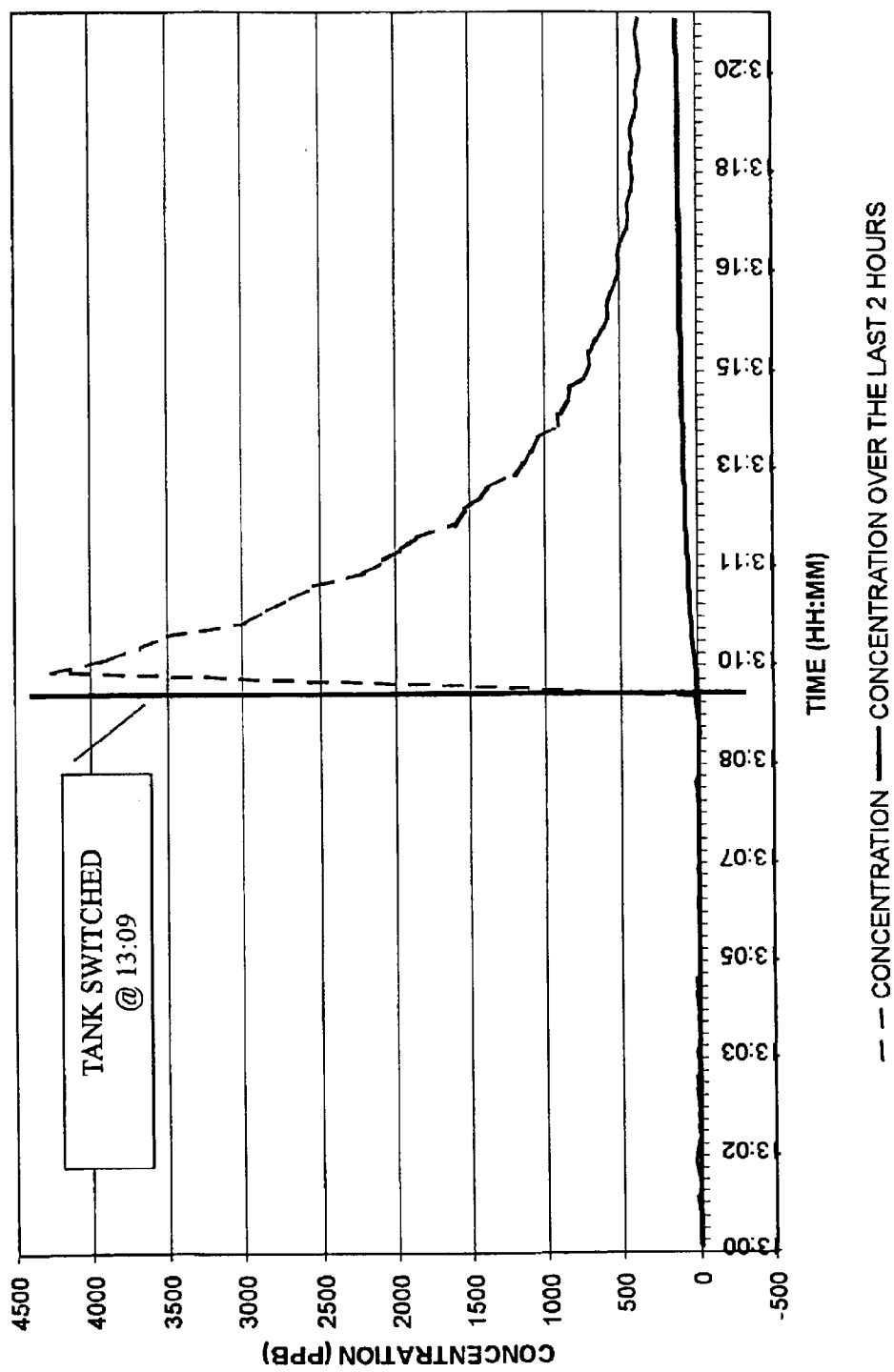
FIG. 28 DETECTION OF CO2 (CARBON DIOXIDE)

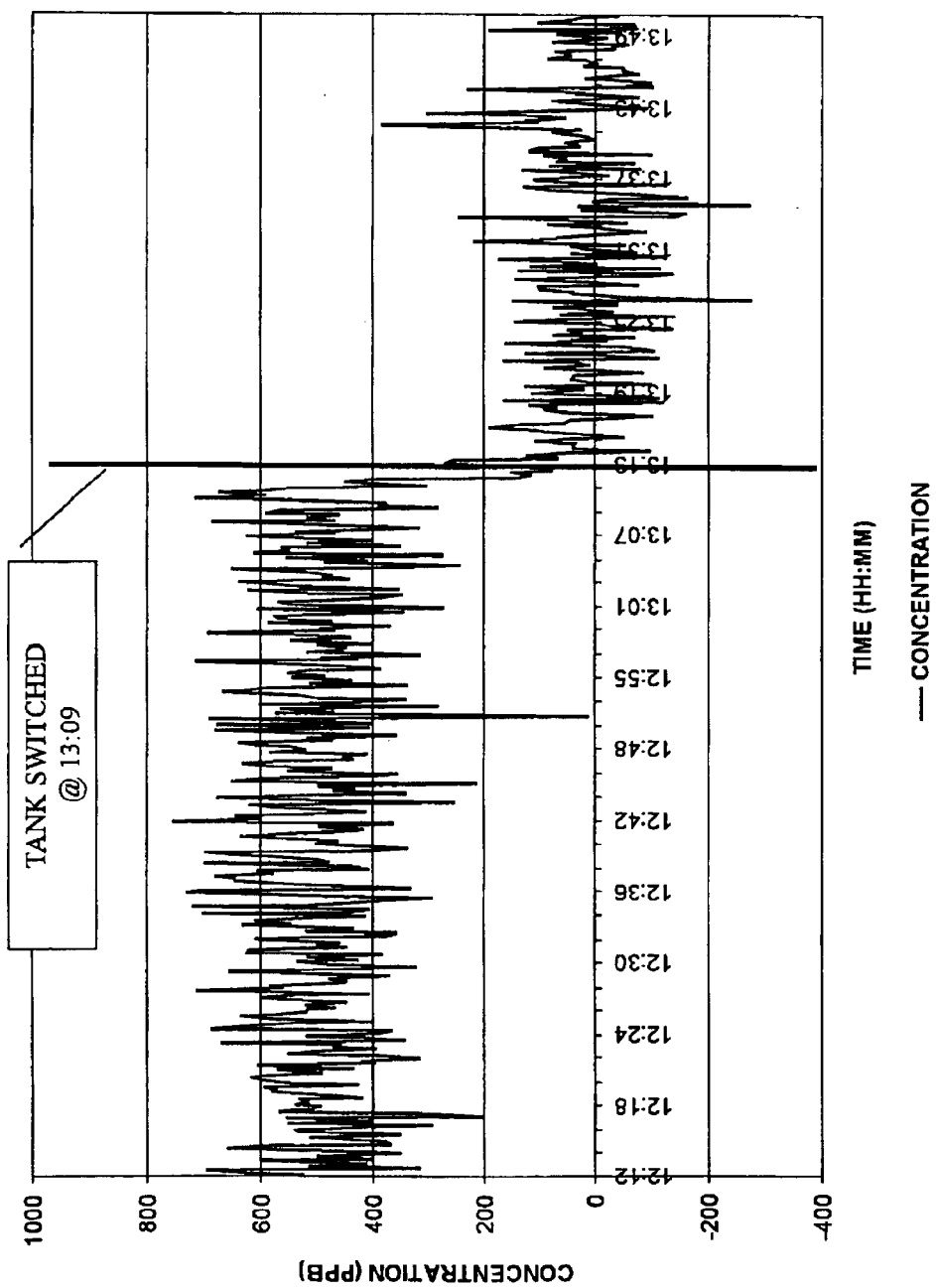
FIG. 29 DETECTION OF CO (CARBON MONOXIDE)

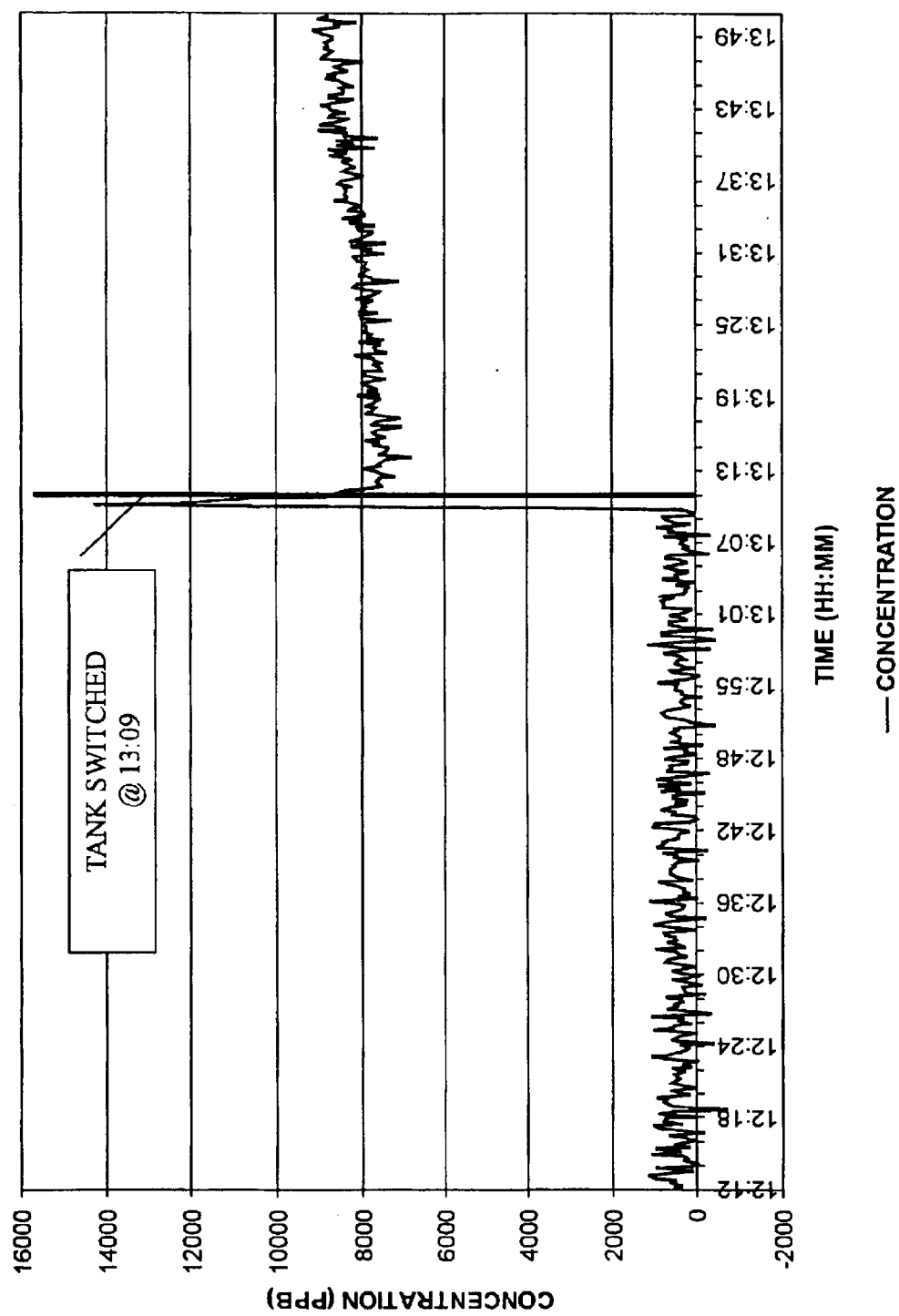
FIG 30 DETECTION OF H2O (WATER)

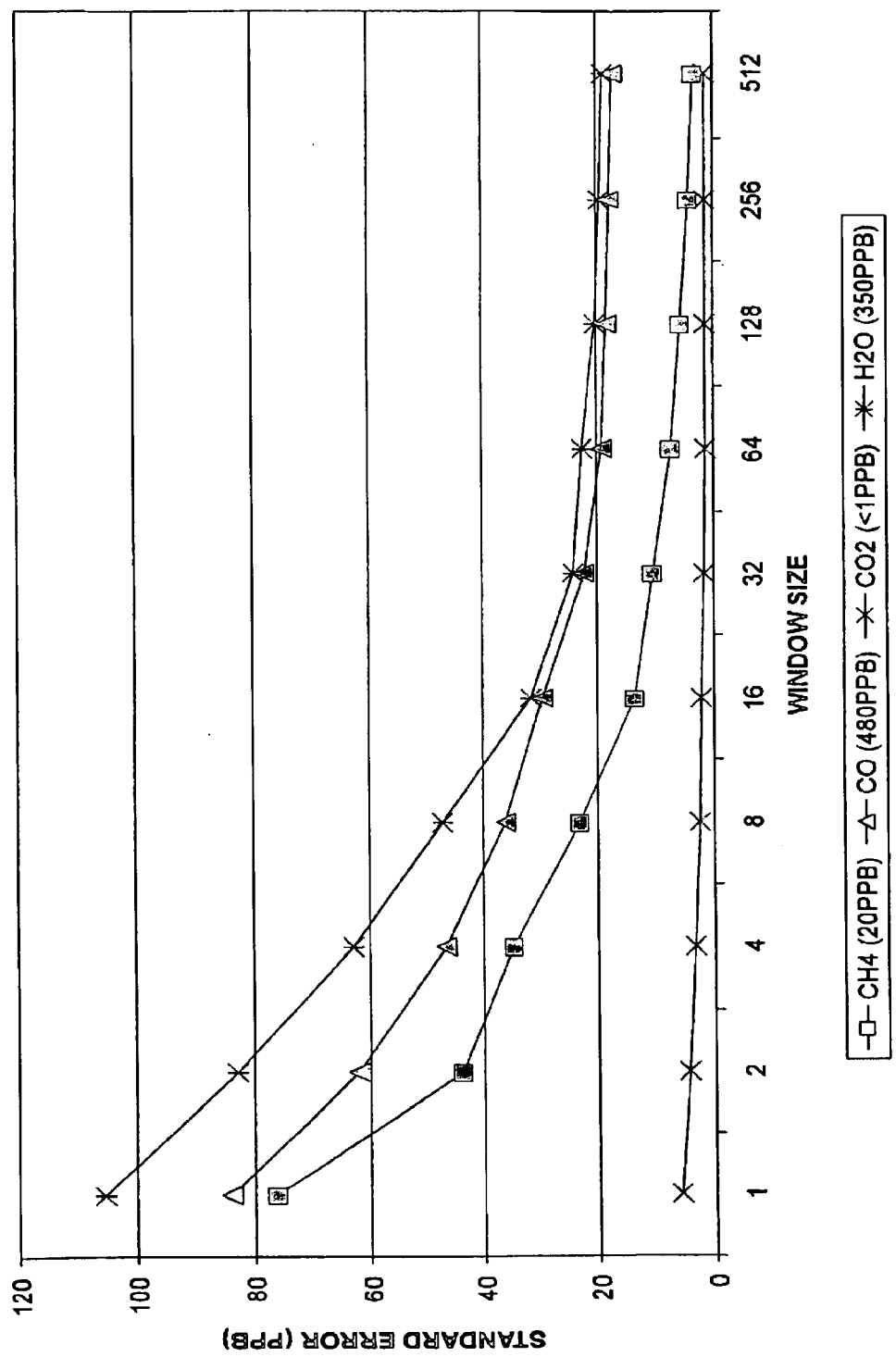
FIG 31 STANDARD ERROR OF DIFFERENT GASES AT DIFFERENT CONCENTRATIONS USING SPECTRASTREAM

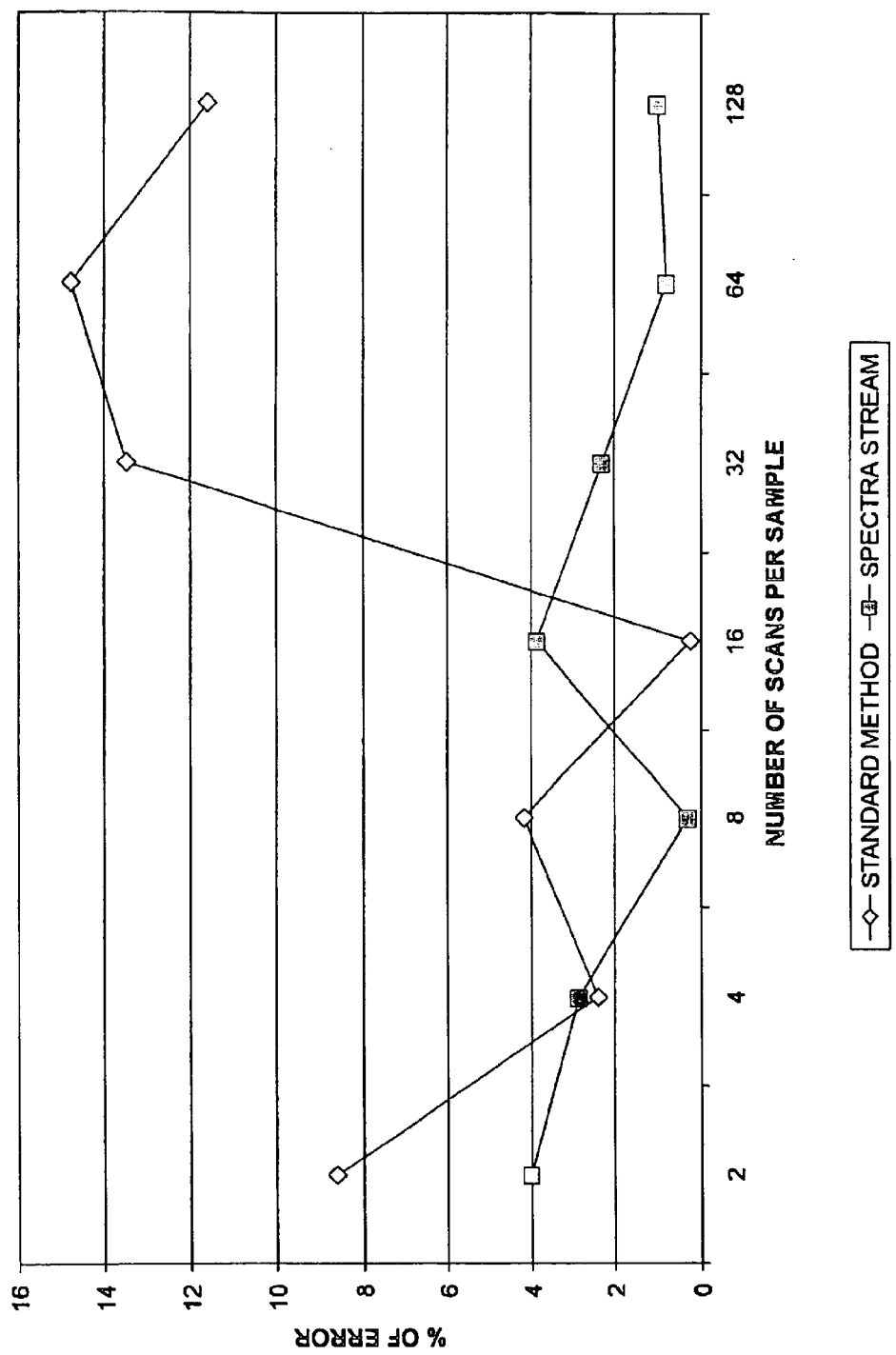
FIG. 32 DETECTION OF 480 PPB OF CO IN N2

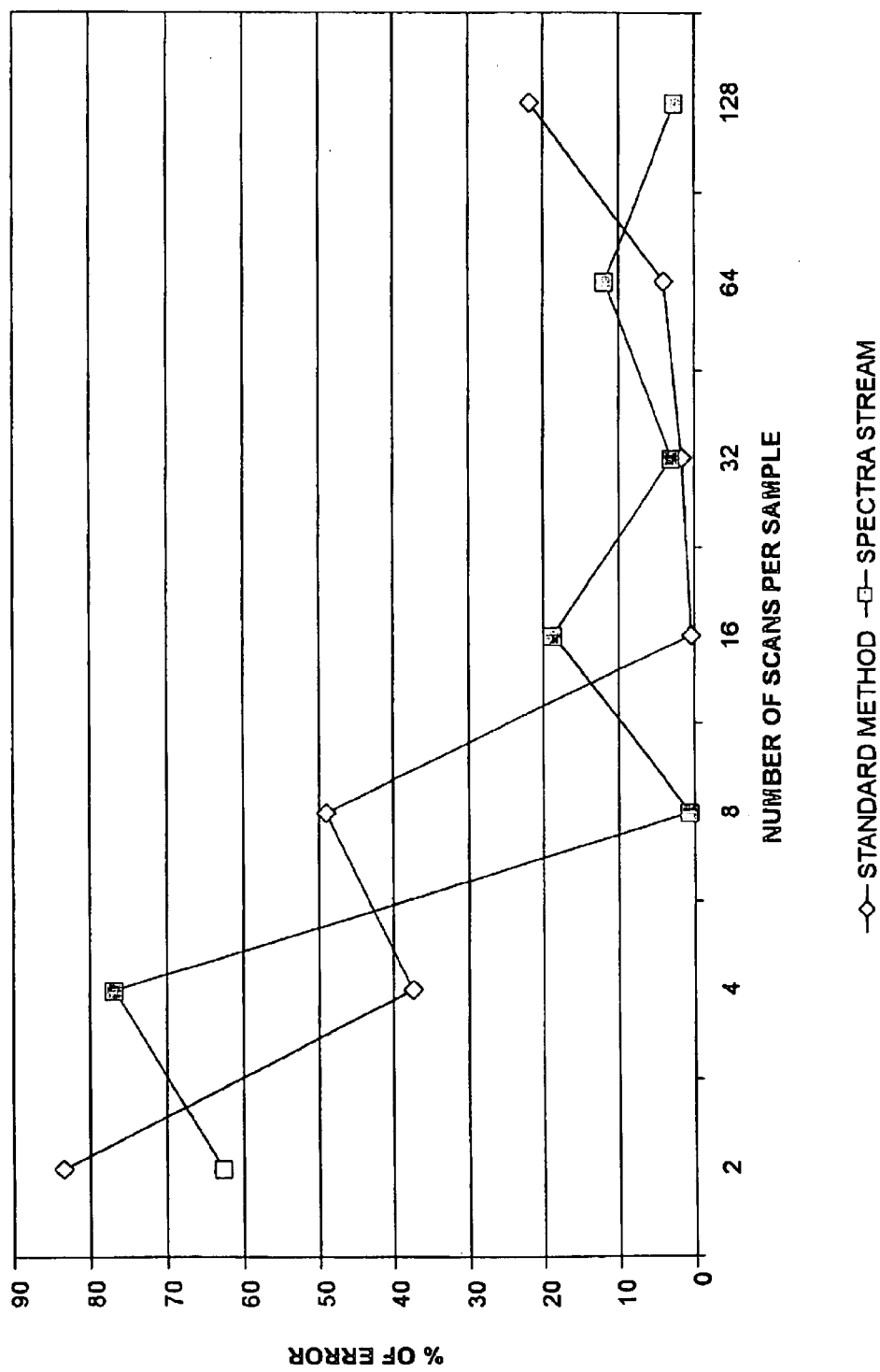
FIG. 33 DETECTION OF 1 PPB OF CO2 IN N2

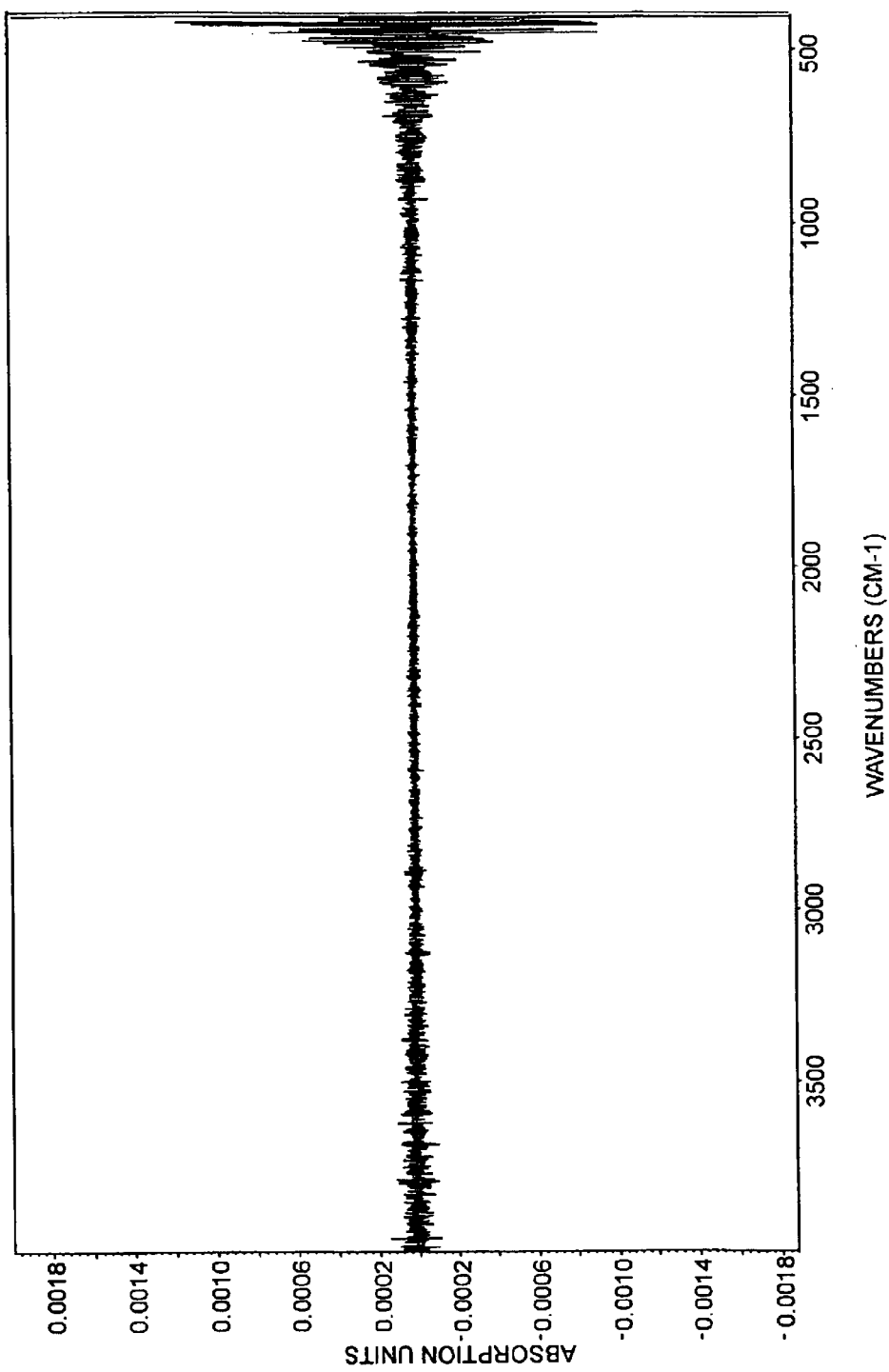
FIG. 34 GAS CELL BASELINE SPECTRA CURVE FITTED TO SAMPLE SPECTRA

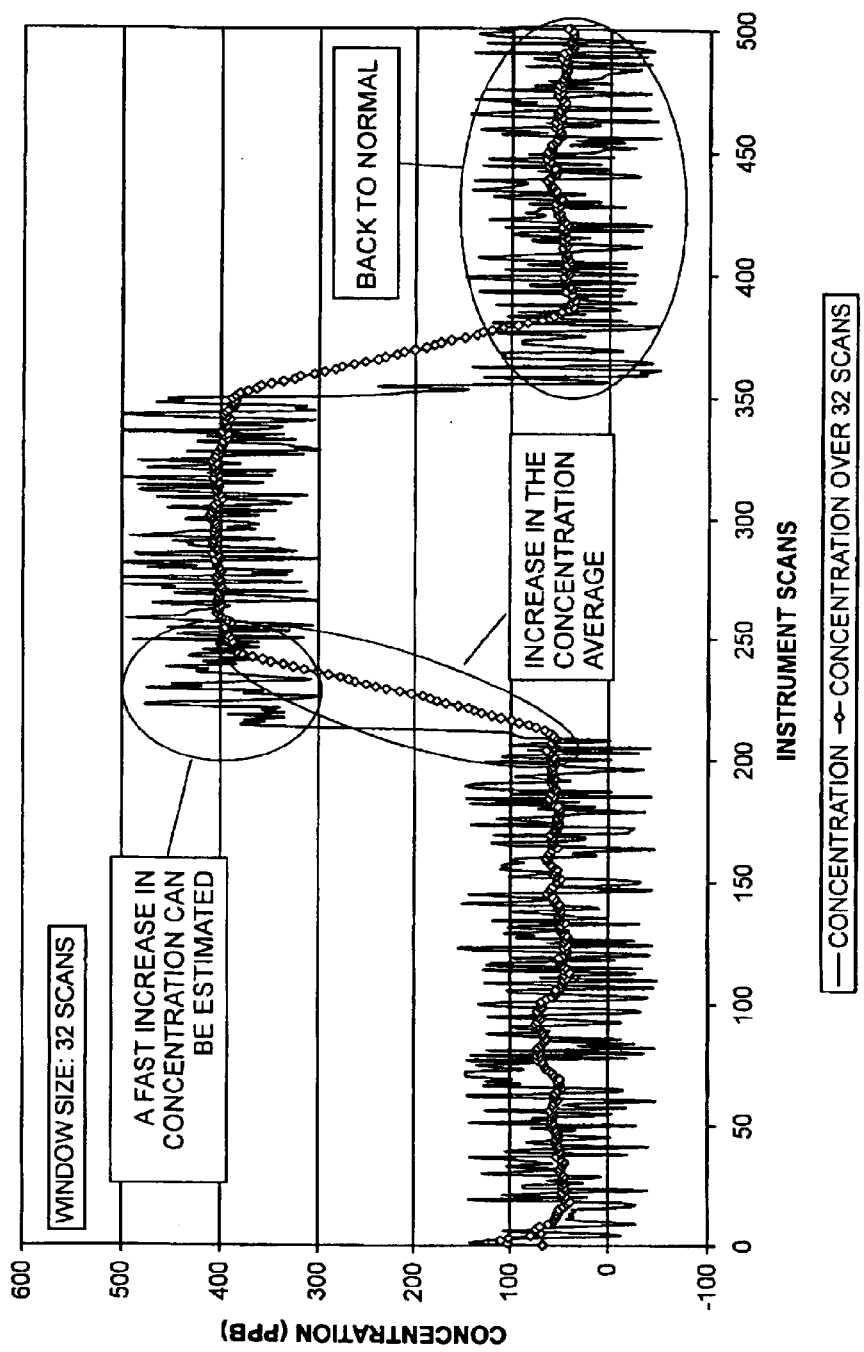
FIG. 35 PLOT ANALYSIS

SPECIALTY GAS ANALYSIS SYSTEM

CROSS-REFERENCE TO RELATED APPLICATIONS

This application claims the benefit of the filing of U.S. Provisional Patent Application Serial No. 60/169,335 entitled "Fast-Response Real-Time, On-Line Chemical Process Spectroscopy Algorithms", filed on Dec. 6, 1999, and the specification thereof is incorporated herein by reference.

BACKGROUND OF THE INVENTION

BACKGROUND ART

Spectroscopy has been used for years in research laboratories and in numerous chemical industries for identifying, measuring, monitoring, and controlling the development and the commercial production of new and existing chemicals, pharmaceuticals, foods, beverages, paints, plastics, semiconductors, and other chemically-based materials. The application of spectroscopy requires both instrumentation and numerical tools to resolve and quantify the chemical compounds which make up the composite spectral records when multicomponent systems are analyzed.

For many years, chemical spectroscopy in industrial settings was performed off-line from the process line, with samples being extracted and taken to an analytical laboratory for analysis and interpretation; this procedure often consumed hours or days before the results were reported back to the chemical process engineer or technician. As a consequence, if the analysis revealed that the chemical process had strayed for its design formulation, the final products could not be used and great quantities of material, time, and money were wasted. In more recent years, on-line instrumentation has been developed and applied to provide chemical analyses which are timely within tens of minutes or more; the result being significantly greater economies of operation and production and higher qualities of finished products. With each improvement achieved, however, process engineers and company executives demand even better systems and increased cost savings.

Every year the semiconductor industry increases the development and use of technology; this leads to added refinements in their production standards and quality levels. Among these changes, the semiconductor industry demands electronic specialty gases with increasingly higher levels of purity every year.

The presence of impurities such as moisture in etching gases can cause corrosion of gas handling systems. The corrosion in a gas handling system leads to the production of particles that can be transported by the high purity gas stream to the wafer. If the gas handling system is contaminated by corrosion particles, these particles can impact device yields or can even cause a process line failure. In both cases, the corroded gas handling system must be replaced. For example, a gas such as HCl containing moisture contamination levels as low as one part per million over volume (1 ppm/v) can cause this problem. Equally important, the variation in moisture impurity levels changes the kinetics of the chemical etching process by perturbing the time sequence for the etching stages. This can cause incorrect electronic circuitry to be generated in the silicon wafer, which can cause entire batches of wafers to be wasted.

Specialty gas manufacturers are required to perform a gas analysis for certification on every gas tank shipped to wafer fab plants. So every gas tank has to go from the production area to the analytical lab to be certified by qualified personnel. On the other hand, at the semiconductor facility, even though every gas tank has been certified, there is still the issue of gas contamination introduced by gas tank degradation over time and improper connection of the gas tank to the manifold system. Also, there is a concern for the presence of leaks between the gas tank and the etching tools when using sub-atmospheric pressure to transport the etching gases; so a final check at the semiconductor facility is also required, either at the gas tank supply point and/or at the process tool.

There are many tools in today's market which provide manual off-line gas analysis and certification. But, to date, there does not exist an analytical tool assembled together, as a complete solution, available on the market that can provide on-line continuous analysis for low concentrations (below the 1 ppm/v level) of moisture and other impurities in the corrosive etching gases. However, as the system described in this thesis continues to develop, a system which meets these needs will soon be introduced to the market.

There are several techniques available to determine moisture concentration in gases, but not all of them are suitable for industrial applications such as on-line gas analysis. The following is a table (Table 1) of these techniques, including their pros and cons, for industrial application.

TABLE 1

Pros and Cons of Techniques to Determine Traces of Moisture in Gases for Industrial Applications

| Technique | Pros | Cons |
| --- | --- | --- |
| Chilled Mirror Hydrometer | Most widely accepted technique for determining trace water in inert gases | Sample requires being in contact with transducer<br>Requires long time to reach equilibrium point<br>Relatively bulky<br>Expensive |
| Electrolytic Hydrometer | Reliable technique for trace water in inert gases above 50 ppb/v | Sample requires being in contact with transducer<br>Slow response time<br>Loss of sensitivity after prolonged use in a dry environment |
| Quartz Crystal Oscillator | None | Sample requires being in contact with transducer<br>Its suitability for use in corrosive gases has not been fully evaluated |

TABLE 1-continued

Pros and Cons of Techniques to Determine Traces
of Moisture in Gases for Industrial Applications

| Technique | Pros | Cons |
| --- | --- | --- |
| Capacitive (Aluminum Oxide and Silicon Oxide) Hygrometers | None | Sample requires being in contact with transducer Sensors can suffer from hysteresis instability and drift in calibration |
| Atmospheric Pressure Ionization Mass Spectrometer | Reliable laboratory technique Offers the lowest detection limit for the measurement of sub-ppb/v to ppt/v water levels | Sample requires being in contact with transducer Impractical for on-line analysis in the microelectronics industry |
| FTIR Spectroscopy and Chemometrics | Sampling is based on optical methods, and the sample is not in contact with transducer Corrosive resistant materials can be used to handle samples Successfully used for trace water detection in corrosive gases Suitable for the detection of other impurities beside water Suitable for the development of an on-line analysis system for the semiconductor industry | Instrumental parameters and data analysis capabilities must be optimized to achieve optimal performance The minimum detectability is estimated to be around 10–25 ppb/v |

As shown in Table 1, FTIR Spectroscopy offers the best characteristics for an on-line, continuous gas analyzer. It offers not only the means of determining moisture concentrations in corrosive etching gases, but it is also suitable for detecting other destructive impurities which may be present in the gas at the same time. This method can be used not only with corrosive gases but also with all gases in general as well. So, the present inventions provides a real-time, on-line and continuous system that can detect traces of different impurities present in the corrosive etching gases.

This present invention provides an industrial turnkey system comprising an automatic on-line monitoring analytical tool for the detection of impurities in corrosive gases in real-time. The system is based on FTIR spectroscopy and controlled by software running on a personal computer. The software provides integration and control of the hardware elements, as well as the spectral analysis and chemometrics, to determine the concentration of impurities in gases. The system is not only capable of detection of low levels of impurities in real-time, but it also provides a method to minimize problems commonly associated with FTIR quantification analysis.

The present invention provides a 10-to-100-fold advancement in the time resolution available to process engineers for monitoring the quality of their real-time chemical process operations. This advancement is obtained by creating chemical spectroscopy quantification software which records, counts, and displays the dynamic impact of every single spectral scan, while at the same time producing data that are time-averages of multiple scans from any type of scanning spectrometer.

As a consequence, changes in an ongoing chemical process, whether undesired or desired, can be detected within the smallest resolvable time interval or period of a single scan of a given spectrometer. For example, using a FTIR spectrometer, the period of a single scan is typically a few seconds. So the effective time resolution for process monitoring becomes seconds rather than minutes.

The present invention achieves its enhancement in time resolution by means of the application of mathematical algorithms which manage and display the data associated with every single spectrometer scan. The invention is available either integrated with the chemical spectroscopy quantification software of the present invention or as a module which can be incorporated into existing commercial spectral analysis software.

SUMMARY OF THE INVENTION
(DISCLOSURE OF THE INVENTION)

The present invention is of a system and method for detection of impurities in gases comprising: providing a Fourier transform infrared spectrometer and employing computer apparatus comprising system control computation apparatus, spectral analysis computation apparatus, and chemometrics computation apparatus. A limit of detection of gas impurities of between approximately 10–25 ppb/v. is provided. In the preferred embodiment, the system control controls gas flow through a gas manifold using gas flow control computation apparatus, controls moisture buildup employing temperature control computation apparatus, and adjusts a transfer mirror. Signal-to-noise ratio is increased by alternating scans between background spectra and sample spectra. Chemometrics employs a running average of a plurality of scans, computes an average concentration of an impurity at every scan, and reports changes in impurity concentrations occurring from both scan to scan and over said plurality of scans. Errors resulting from baseline drift are reduced by assuming that system baseline is not necessarily centered around an x-axis of collected spectra.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 1 is a block diagram of the data collection of the present invention;

FIG. 2 is a block diagram of the data quantification of the present invention;

FIG. 3 is a system block diagram of the present invention;

FIG. 4 is the preferred system hardware configuration of the present invention;

FIG. 5 is a diagram of the FTIR spectrometer and personal computer interconnection used in the present invention;

FIG. 6 is a block diagram of the present invention;

FIG. 7 is a block diagram of Process 1 and sub-processes;

FIG. 8 is a diagram of the gas handling system hardware driver of the present invention;

FIG. 9 is a prior art White cell design;

FIG. 10 shows purge box mirrors in a "Mirrors Out" position;

FIG. 11 shows purge box mirrors in a "Mirrors In" position;

FIG. 12 shows a purge box DC motor hardware driver;

FIG. 13 shows a TInstrument state diagram of the present invention;

FIG. 14 shows a run state diagram of the present invention;

FIG. 15 shows a block diagram of the digital I/O controller interaction with other controllers;

FIG. 16 shows a controller packet format of the present invention;

FIG. 17 shows a read command data format of the present invention;

FIG. 18 shows a respond to a read command data format of the present invention;

FIG. 19 is a "MODBUSSocket" interaction block diagram of the present invention;

FIG. 20 is a prior art schematic representation of a Michelson interferometer;

FIG. 21 is a graph showing the baseline after collecting a long background and sample spectra;

FIG. 22 is a graph showing the system baseline using "SpectraStream" with no system purging at all;

FIG. 23 is a graph showing conventional baseline collection with low flow rate purging;

FIG. 24 is a graph showing the system baseline using "SpectraStream" with no system purging at all;

FIG. 25 is a graph showing gas cell baseline spectra minus sample spectra;

FIG. 26 is a graph showing moisture detection analysis in accordance with the present invention;

FIG. 27 is a graph showing detection of $CH_4$ (methane) in accordance with the present invention;

FIG. 28 is a graph showing detection of $CO_2$ (carbon dioxide) in accordance with the present invention;

FIG. 29 is a graph showing detection of CO (carbon monoxide) in accordance with the present invention;

FIG. 30 is a graph showing detection of $H_2O$ (water) in accordance with the present invention;

FIG. 31 is a graph showing the standard error of different gases at different concentration using "SpectraStream" of the present invention;

FIG. 32 is a graph showing detection of 480 ppb of CO in $N_2$ in accordance with the present invention; and FIG. 33 is a graph showing detection of 1 ppb of $CO_2$ in $N_2$ in accordance with the present invention.

FIG. 34 is a graph of gas cell baseline spectra curve fitted to sample spectra; and FIG. 35 is a graph showing quantification analysis.

DESCRIPTION OF THE PREFERRED EMBODIMENTS

Best Modes for Carrying Out the Invention

Fourier Transform Infrared (FTIR) Spectroscopy bases its functionality on the principle that almost all molecules absorb infrared light. Only the monatomic (He, Ne, Ar, etc.) and homopolar diatomic ($H_2$, $N_2$, $O_2$, etc.) molecules do not absorb infrared light. Molecules only absorb infrared light at those frequencies where the infrared light affects the dipolar moment of the molecule. In a molecule, the differences of charges in the electronic fields of its atoms produce the dipolar moment of the molecule. Molecules with a dipolar moment allow infrared photons to interact with the molecule causing excitation to higher vibrational states. The homopolar diatomic molecules do not have a dipolar moment since the electronic fields of its atoms are equal. Monatomic molecules do not have a dipolar moment since they only have one atom. Therefore, homopolar diatomic molecules and monatomic do not absorb infrared light. But all other molecules do.

Most FTIR spectroscopy uses a Michelson interferometer to spread a sample with the infrared light spectrum and measure the intensity of the infrared light spectrum not absorbed by the sample. FTIR spectroscopy is a multiplexing technique, where all optical frequencies from the source are observed simultaneously over a period of time known as scan time.

The spectrometer measures the intensity of a specially-encoded infrared beam after it has passed through a sample. The resulting signal, which is a time domain digital signal, is called an interferogram and contains intensity information about all frequencies present in the infrared beam. This information can be extracted by switching this signal from a time domain digital signal to a frequency domain digital signal, which is accomplished by applying a Fourier transform over the interferogram and producing what is called a single beam spectrum. Another characteristic of this signal is that it is a statistically stationary signal, so the higher the number of scans of which this signal is composed, the better the estimate that can be extracted from the data.

As mentioned earlier, almost all molecules absorb infrared light, and each type of molecule only absorbs infrared light at certain frequencies. This property provides a unique characteristic for each molecule. It provides a way to identify the molecule type (qualitative analysis) and the amount or quantity of this molecule in the sample (quantitative analysis). Since each type of molecule only absorbs at certain frequencies, it provides a unique absorption spectral pattern or fingerprint through the entire infrared light spectrum. In this way, the more molecules of the same type in the sample, the more infrared light is absorbed at those specific frequencies at which those molecules absorb infrared light.

One can observe, by looking at moisture "fingerprints" with absorption bands, that different moisture concentrations present almost identical patterns, but the sample with the most moisture has higher peaks.

The height of the peaks are defined by the Beer-Lambert relationship (or Beer's law). Beer's law states that the concentration C is directly proportional to the absorbance A. This is:

$$A = abC \qquad \text{Equation 1}$$

where a is the absorptivity of the molecule and b is the pathlength or distance that the light travels through the sample gas.

This relationship is used to determine the concentration of a molecule in a gas by comparing the height of a maximum absorption peak of the molecule in a reference gas spectrum to the height of the corresponding peak in a sample spectra.

An absorption spectrum is calculated by performing the logarithmic ratio between a sample single beam spectrum and a background single beam spectrum. The sample measures the intensity of the infrared light reaching the detector with a sample placed in the path of the encoded infrared light. The background is a single beam spectrum that measures the intensity of the infrared light reaching the detector without any sample. The frequencies of infrared light radiation that are absorbed and the strength of these absorption bands are determined by the sample's chemical makeup.

It is important to note that the single beam background spectrum is used as a point of reference to determine the absorption of a sample inside the sample compartment. This background reflects the conditions inside the spectrometer at the moment it was taken, so it is important to maintain a stable environment inside the spectrometer. This means that the conditions inside the spectrometer must have minimal fluctuations, through all background and sample collections.

As an example, consider the normal impurities inside a spectrometer. These impurities start absorbing infrared light immediately after the light is emitted by the infrared light source. The infrared light absorbed by these impurities are reflected in the background spectrum; however, since the sample spectrum goes through the same path inside the spectrometer, the sample should reflect the same amount of infrared light absorbed plus the infrared light absorbed by the sample. If the impurities increase inside the spectrometer while the scanning of the sample spectrum is in progress, then this increment in impurities is interpreted as part of the impurities in the sample.

The present invention provides a turnkey system comprising an automatic on-line monitoring analytical tool for the detection of impurities in corrosive gases in real-time. This system is based on FTIR spectroscopy and controlled by software preferably running on a personal computer. A system architecture was designed to provide the integration and control of the system elements, as well as the spectral analysis and chemometrics, to determine the concentration of impurities in gases. This software is referred to as "specialty gas analysis software" or "SPGAS." Features of the software are as follows:

Provides the interface to interact automatically with the hardware required for an optimal analysis;

Provides a limit of detection (LOD) for gas impurities of at least 10–25 ppb/v.;

Reduces the detection time normally associated with FTIR spectrometry;

Increases the SNR of the collected data from the FTIR spectrometer;

Reduces the response time and increases the accuracy of the system for the detection of impurities; and Reduces the effects of spectrometer drift upon the spectral data.

The present invention provides a gas or fluid analysis tool that permits the user or process engineer in a facility (e.g., a semiconductor wafer etching facility) to know almost instantaneously when a gaseous or fluid component starts to stray from its prescribed or acceptable concentration level. Whereas prior art spectral analysis requires ten minutes or more to detect and signal a concentration change in the ppb range, the method of the present invention can do so in a matter of seconds. The present invention draws upon multi-band, multi-component classical least squares formulation of the "SPGAS" and "SpectraStream" (both described below) quantification software as applied to FTIR spectroscopy. In the best case, the minimum time interval in which a concentration change can be detected with reliability is the time duration of a single scan of the interferometer. Hence, departures of the actual concentration level from the prescribed level are detected immediately as an early warning signal. Not only does the method of the invention respond faster to concentration changes but it also permits continuous flow of the gas sample and continuous concentration monitoring. In addition, the lower noise levels normally associated with multiple scans are preserved without the requirement of multiple scans.

"SpectraStream" is a system of the present invention that reduces the effects of three critical problems of spectra collection (spectral noise; spectrometer drift; and spectra collection time). The invention comprises several methods. One is a data collection method and another is a data quantification process method. These two methods provide the mathematical steps which must be imbedded in spectral analysis quantification programs to accomplish the fast-response, real-time features of the invention. The data collection method follows:

Data Collection Process Method

1. //Reservation of system resources
2. Reserve enough systems resources to store a Max_Window_Size data arrays of k scan interferogram (InterferogramArray)
3. Reserve enough systems resources to store a data array of a single Interferogram (Interferogram)
4. Reserve enough systems resources to store a data array of a single Sample spectra (Sample)
5. Reserve enough systems resources to store a data array of a single Background spectra (Background)
6. Reserve enough systems resources to store a data array of a single Absorbance spectra (Absorbance)
7. //Collection and storage of background spectra
8. Set spectrometer conditions to collect a m scans background spectra
9. Start the m scans background spectra collection
10. Wait until spectrometer is done with the m scan background spectra
11. Retrieve background spectra data from spectrometer.
12. Store background spectra data in Background
13. //After each new background spectra, reinitialize collection of sample interferogram
14. Set Interferogram$_{Index}$=1
15. Set Window_Size =1
16. //Collection and storage of a sample k scans interferogram
17. Set spectrometer to collect a k scans interferogram (default: k=1)
18. Start the k scans interferogram collection
19. Wait until spectrometer is done with the k scan interferogram collection
20. Retrieve interferogram data from spectrometer.
21. Store interferogram data at InterferogramArray [Interferogram_Index] position
22. The number of averaged interferograms increases gradually with each new scanned interferogram, until Window_Size equals Max_Window_Size 23. Calculate the Interferogram average of Window_Size interferograms $$Interferogram = \frac{1}{Window\_Size} \sum_{i=1}^{Window\_Size} InterferogramArray[i]$$

24. If (Window_Size<Max_Window_Size), then Window_Size =value of Window_Size+1
25. If (Interferogram_Index=Max_Window_Size), then set Interferogram_Index=0
26. Set Interferogram_Index=value of Interferogram_Index+1
27. //Calculate the sample spectra of the averaged Window_Size interferogram
28. Use the appropriate apodization, phase correction and Fourier transform algorithms to compute the sample spectra of the average interferogram stored into Interferogram and store the result into Sample
29. //and obtain its absorbance spectra against Background
30. Compute the absorption spectra base on the background spectra stored into Background and sample spectra stored into Sample and store the results into Absorbance
31. Send Absorbance to the Data Quantification Process so concentration of impurities on it can be quantified.
32. If the life of background spectra as expired, then go line number 7, else go to line number 16.

The data quantification method follows:

Data Quantification Process Method

1. //Reservation of system resources to store the past q estimations of the p elements so we can observe and estimate big changes on concentration in any of the p elements.
2. Reserve enough systems resources to store a two dimensional data of array of p by q to store the calculated concentration of p components, and track these concentrations over the past q concentration estimations per component. (Concentration_Tracker)
3. Set Tracker_Index=1
4. Wait until and absorbance spectra is received
5. //Calculate the concentration of the p elements
6. Use any available quantitative analysis algorithm to perform a multi-component quantitative analysis to determine the concentration of different components over the absorbance spectra received.
7. //and store only the last q concentration estimations
8. Store the concentration estimation j at Concentration_Tracker[j][Tracker_Index] for j=1..p
9. If (Tracker_Index=q), then Tracker_Index=0;
10. Set Tracker_Index=value of Tracker_Index+1;
11. //Perform statistical analysis to determine if the last concentration is within a normal concentration range or out of range concentration
12. If the mean, variation, or standard deviation of the differentiation of these q values per component j goes beyond a certain threshold, a positive and significant increase on concentration can be estimated with certain degree of confidence and proper action can be taken. Go back to 4

FIG. 1 illustrates the application of the invention to FTIR spectrometry. The individual scans (k=1) or scan sets (k>1) of interferograms from both background scans and sample scans are converted first to "single beam" spectral records and thence to absorbance spectra in the normal manner of Fourier Transform data processing. Variables available to the operator are:

k=number of scans used to create a single interferogram at a specific spectrometer resolution (default k=1);
t=time to perform k scans; and
x=window size (number of k scans interferograms used to produce a sample spectra).

FIG. 2 demonstrates that the quantification analysis of this invention is performed at every scan of the spectrometer (at every t time); and not like in the conventional method where the quantification analysis is performed at a minimum of x scans (at every x*t time). Since every estimation of the quantified sample concentration is the average of the concentration of the previous x scans, the difference between the previous concentration and the current concentration is used as a parameter to determine how much the concentration is increasing or decreasing. As a consequence, the difference parameter provides an early warning if the concentrations of chemical species being monitored go beyond minimum or maximum thresholds.

The present invention provides three primary features:
1. Real-time gas analysis;
2. On-line gas sampling automation process; and
3. Self-diagnostics and self-validation tools.

Each one of these features has its own particular requirements and set of rules.

The system of the present invention is shown in a block diagram (see, FIG. 3). The system hardware prototype is shown in FIG. 4 which the SPGAS system has to control and automate.

Real-time Gas Analysis

As discussed earlier, FTIR spectroscopy offers the best characteristics to perform real-time detection of moisture and other impurities that may be present in the corrosive gases used by the semiconductor industry and other industries. Since the infrared light detector is not in contact with the corrosive sample, it is not affected and the instrument can therefore be set for a continuous operation and scanning of the sample.

The real-time gas analysis is preferably performed through an FTIR spectrometer, which contains a special gas sample compartment or gas cell that is connected directly to a gas line that supplies the sample gas. Since the spectrometer is connected directly to a computer (see, FIG. 5) the spectrometer can be set to perform continuously an x number of scans of the sample gas and store this data as an interferogram. Every time an interferogram is completed, the computer retrieves this interferogram from the spectrometer and performs the quantitative gas analysis of the impurities.

The gas analysis process is in two main processes (see, FIG. 6). One process is the data collection and the second process is the data processing.

Process 1 controls the interaction between the spectrometer and the computer. Additionally, process 1 interacts with and synchronizes other sub-processes that set and control the sampling and the environmental conditions of the spectrometer. These sub-processes control the gas handling system and the temperature controller (see, FIG. 7).

On-line Gas Sampling Automation Process

The system of the present invention must be capable of controlling the gas flow through the gas manifold; hence, the gas handling system is automated preferably by using pneumatic valves that are controlled individually by a digital I/O card connected to the computer.

A gas handling control protocol controls these valves and groups them according to the gas flowing requirements. The gas handling system is capable of handling multiple (e.g., four) different states of which one is always on:

1. All valves off;
2. Purging spectrometer (always "on");
3. Purging system; and
4. Sample gas flowing.

These are discussed in detail below.

1. All Valves Off

The "all valves off" is the initial state of the gas handling system. Also, in the case of the system losing electrical power, emergency shutdown, system shutdown or any other critical error on the system, all valves would return to this state.

2. Purging Spectrometer

The purging spectrometer (always "on") requires a constant purge with a high purity gas to reduce the fluctuation of the environment inside the spectrometer. Normally ultra-dry nitrogen is used as a purging gas since its molecules do not have an absorption signature in the infrared spectrum. This state is always "on" since the spectrometer requires constant purging.

3. Purging System

The entire gas handling system occasionally requires purging so impurities can be driven out of the system. This purging includes removing the impurities on the walls of the gas cell to prevent counting these impurities as part of the impurity level of the sampling gas.

4. Sample Gas Flowing

This state allows the sampling gas to flow through the system to fill and pass through the gas cell. The scanning of the gas is performed during this stage to determine the concentration of impurities of the flowing gas.

Table 2 summarizes the state of each individual valve for each one of the gas handling system states.

TABLE 2

Gas Handling System States

|  | Valves | | | |
| --- | --- | --- | --- | --- |
|  | V1 | V2 | V3 | V4 |
| All Valves Off | ■ | ■ | ■ | ■ |
| Purging Spectrometer | ○ | ○ | ○ | ○ |
| Purging System | ■ | □ | ■ | □ |
| Sample Gas Flowing | □ | ■ | □ | ○ |

■ Close
□ Open
○ Open/Close

Self-diagnostics and Self-validation Tools

SPGAS is able to interact with each one of the components of the hardware system and determine their state and proper functionality. So, each electronic hardware component provides a feedback of its status. Every time a fail condition from the electronic hardware is detected, it is recorded into a log file and accordingly triggers an alarm condition to the severity of the failure.

The feedback from the various system components are used to validate the conditions prior to the quantification of impurities through SPGAS. SPGAS verifies that all parameters are within an acceptable range.

Gas Handling System

In the preferred embodiment, the automatic gas handling system uses four pneumatic valves (see, FIG. 4). These valves are controlled through a computer by using a digital I/O card. The digital I/O card is connected to a valve driver board to actuate each pneumatic valve and a separate digital line is used for each valve. By turning on and off each digital port of the digital I/O card, the valves are controlled. The valve driver board is connected to a solenoid valve array, which directs the pneumatic flow to the pneumatic valves (see, FIG. 8). Each valve is controlled pneumatically; but if a feedback is required from each valve, indicator switches may be installed on each valve to report the state of each valve.

Although pneumatic valves are shown in the drawings, other types of valve controls, known in the art, may also be used in accordance with the present invention.

Digital I/O Board

The use of a parallel digital input/output PC board provides the required functionality and interaction between SPGAS and other pieces of hardware outside the computer. This board allows one to control the gas handling system driver, receive valve state feedbacks from all the valves, position the transfer mirrors to two positions within the purge box of the gas cell, and receive the state signals from the emergency shutdown button.

The numbers of digital I/O ports required by the system are as follow:

4 digital outputs to control 4 valves of the gas handling system;

1 digital output to set the two positions of the mirrors inside the purge box;

4 digital inputs for state of all the valves of the system;

2 digital inputs for state of the mirror position inside the purge box; and 1 digital input for state of the emergency stop button.

Therefore, the system requires five digital output ports to control the system and seven digital input ports for feedback from the system.

The preferred digital I/O board is a PIO-24 parallel digital interface board. This board has three TTL/CMOS-compatible, digital I/O ports, PA, PB, and PC. PA and PB are both byte wide (8-bit) and are usable as inputs or outputs. PC is also a byte wide but is adaptable for use as two separate 4-bit ports: PC lower and PC upper, each of which is usable as input or output.

Port PA is preferably configured as an output port to control all the output operations. Port PB and PC are configured as input ports to receive feedback from the system. Table 3 shows a preferred bit map assignment of every port.

TABLE 3

Digital I/O Port Mapping

| | | Values | | | | Mirrors | | Emergency | |
| --- | --- | --- | --- | --- | --- | --- | --- | --- | --- |
| | | 1 | 2 | 3 | 4 | In | Out | Stop | Reserved |
| PA Output | 0 | ✓ | | | | | | | |
| | 1 | | ✓ | | | | | | |
| | 2 | | | ✓ | | | | | |
| | 3 | | | | ✓ | | | | |
| | 4 | | | | | | | | ✓ |
| | 5 | | | | | | | | ✓ |
| | 6 | | | | | | | | ✓ |
| | 7 | | | | | | ✓ | | |

TABLE 3-continued

Digital I/O Port Mapping

| PB Input | 0 | ✓ | | | | | | |
|---|---|---|---|---|---|---|---|---|
| | 1 | | ✓ | | | | | |
| | 2 | | | ✓ | | | | |
| | 3 | | | | ✓ | | | |
| | 4 | | | | | | | ✓ |
| | 5 | | | | | | | ✓ |
| | 6 | | | | | | | ✓ |
| | 7 | | | | | | | ✓ |

| PC Input | 0 | | | | | | ✓ | |
|---|---|---|---|---|---|---|---|---|
| | 1 | | | | ✓ | | | |
| | 2 | | | | | ✓ | | |
| | 3 | | | | | | | ✓ |
| | 4 | | | | | | | ✓ |
| | 5 | | | | | | | ✓ |
| | 6 | | | | | | | ✓ |
| | 7 | | | | | | | ✓ |

Temperature Controller

Moisture is very difficult to work with. Its tendency to adhere to surfaces with which it makes contact slows down the concentration estimation. The walls of the pipes and gas cell will adsorb moisture if the moisture in the gas increases and they will slowly desorb moisture if moisture in the gas decreases until a stable point is reached.

Heating the walls and mirrors of the gas cell accelerates the process of releasing moisture adhered to the gas cell internal walls and mirrors. The gas cell is heated to a certain temperature for working conditions and to a higher temperature for self-cleaning by use of a temperature controller and resistive heater. By allowing SPGAS to interact with the temperature controller, SPGAS schedules and automates the self-cleaning and working conditions of the gas cell.

Spectrometer

The use of FTIR spectroscopy for gas analysis requires special considerations due to the fact that gases inside a specific volume, compared to against a solid or a liquid, have a significantly smaller number of molecules over the same volume. Therefore, the total amount of infrared light absorbed by the gas is a lot less than the total amount of infrared light absorbed by a liquid or a solid, producing a weaker absorption signal and decreasing the detection limit of the spectrometer over gases.

The detection limit of the instrument is increased when the infrared light travels a longer path through the gas sample or if the gas pressure inside the sample compartment is increased. The increase of pressure inside the gas compartment is less preferable since this increases the quantity of the gas consumed per sample. The path that the infrared light has to travel through the sample gas is increased considerably by using a long path gas cell to sample the gas. The long path gas cell increases the path by receiving and reflecting the infrared light multiple times inside its body before it lets the light go out and be received by the infrared detector. So, the longer the distance the infrared light travels the more infrared light is absorbed by the sample gas, which increases the height of the absorption peaks and makes them easier to detect.

The use of an FTIR spectrometer requires continuous purging, e.g., with dry nitrogen. This purging provides a stable environment for the spectrometer and reduces interfering impurities inside the spectrometer; otherwise the variation of these absorbing impurities inside the spectrometer counts as part of the gas that the system is sampling.

Long Path Gas Cell

The use of a White cell in the present invention (see, FIG. 9) provides a very high percentage of light transmission, which is important for observing spectra that are very weak or compounds at very low concentrations. It is useful for any gas that does not injure the mirror surfaces.

Since SPGAS analyzes corrosive gases, the gas cell construction and mirrors must withstand such gases. The gas cell preferably has a heating element attached to the outside wall. This heating element in conjunction with the temperature controller heats the inside walls and mirrors of the gas cell, reducing moisture inside the cell.

Comparing the original light throughput for the gas cell when new, against the actual light throughput at a later time, allows one to determine the degradation of the internal optics over time, thus monitoring the performance and life of the gas cell.

The gas cell is preferably equipped with motorized movable mirrors and mirror position feedback. These features allow a computer-directed removal of the transfer mirrors of the purge box, resulting in a straight through reference or background spectra without going through the gas cell optical path (see, FIGS. 10 and 11).

FIG. 12 and Table 4 show the hardware controller and the logic in charge of moving the mirrors in and out.

TABLE 4

Purge Box DC Motor Hardware Driver True Table

| Set Mirrors x | Mirrors In Feedback y | Mirrors Out Feedback z | Motor Direction x | Move Motor (xy)(xz) |
|---|---|---|---|---|
| 0 | 0 | 0 | 0 | 1 |
| 0 | 0 | 1 | 0 | 1 |
| 0 | 1 | 0 | 0 | 0 |
| 0 | 1 | 1 | 0 | 0 |
| 1 | 0 | 0 | 1 | 1 |
| 1 | 0 | 1 | 1 | 0 |
| 1 | 1 | 0 | 1 | 1 |
| 1 | 1 | 1 | 1 | 0 |

The logic behind this hardware controller is to provide a simple interactive interface with a computer through a digital I/O port. These interactions are the computer indicating the position of the mirrors through an output port (in or out) and the hardware controller telling the computer the position of the mirrors through two input ports (in, out or moving). Two switches inside the purge box signal the position of the mirrors, i.e., in or out.

Emergency Shutdown

An emergency shutdown button controls the power supply to the gas handling system and vacuum system. Since all valves are normally closed, a cut of the electrical power closes all valves and turn pumps off. By pressing the emergency button, the power supply is cut off and sends a signal to the computer through the digital I/O card so proper actions can be taken by the system (see, FIG. 8)

Software

The following is a description of control of the hardware associated with collection of spectral data. The proper functionality of this hardware provides reliable spectral data for analysis.

Hardware Control

SPGAS manages the control and synchronization of several instrument hardware components. The control of just one single piece of hardware is a hard task. The synchronization of several pieces of hardware becomes even more difficult due to the diversity of the hardware components, the way they are connected to the computer, their protocols, and their functionality.

Through the use of object-oriented programming, this complexity is encapsulated by defining a base class that provides a common interface and the means to synchronize the different but similar procedures that have to be performed on each piece of hardware. These similar procedures are the opening and closing of communications With the instrument, the instrument testing and validation, the configurings, the starting and stopping of the process of which each instrument is in charge, and finally the error detection of the instrument.

This encapsulation allows the creation of derived classes that specialize in the control, synchronization and verification of the instrument that it has to manage. The following is the definition of "TInstrument," which is the base class for all the instrument class definitions.

---

1. Methods or procedures (all defined as virtual)
   - Open
   - Close
   - Reset
   - Validation
   - Config
   - Start
   - Stop
   - WaitForEvent
   - CheckStatus
   - ExecuteInstructions
   - SetPointReach
   - ReportStatus
   - ErrorState
2. Callback procedures or events
   - On_Error
   - On_Timer
   - On_Instruction
   - On_InstructionDone
   - On_CheckStatusDone
   - On_SetPointDone
   - One_SetPointReached
3. Properties or data members
   - Status
   - Status_Descriptor
   - LastError
   - Error_Descriptor
   - Timer_Interval

---

FIG. 13 and FIG. 14 show the state diagrams that every instrument follows; and Table 5 summarizes the action or procedure performed at each state.

TABLE 5

TInstrument's Class Description

| Method | Description |
| --- | --- |
| Open | The proper channels to link the computer with the instrument are opened |
| Configuration | The instrument is initialized to the required working configuration |
| Validation | A test is done over the instrument to see if it works within parameters |
| Start | The instrument starts functioning |
| Run | The instrument executes instructions and performs checks on the conditions of the instrument |
| Stop | The instrument stops functioning |
| Close | The communication channels between the computer and the instrument are closed |

TABLE 5-continued

TInstrument's Class Description

| | |
| --- | --- |
| Done | The instrument controller stops all its activities and it is either to be reinitialized or destroyed |
| ReportStatus | The instrument is asked to report its status to another object (Watch Dog) to verify that it is still operational |
| Error | Depending on the severity of the error, it may allow the instrument to continue, reinitialize, call to stop the system operation and set the proper alarm conditions |

| Event | Callback Procedure Description |
| --- | --- |
| On_Error | Called in case of error |
| On_Timer | Called during the Run State every x milliseconds |
| On_Instruction | Called before a command is executed by the instrument in the Run Stage |
| On_InstructionDone | Called after a command is executed successfully by the instrument in the Run Stage |
| On_CheckStatusDone | Called after the status of the instrument is checked successfully and the instrument has not reached the set point |
| On_SetPointReached | Called after the status of the instrument is checked successfully and the instrument has reached the set point |
| On_SetPointDone | Called after the SetPointReached method has been executed. |

| Property | Description |
| --- | --- |
| Status | Actual status of the instrument (Numerical value) |
| Status_Description | Actual status of the instrument (String value) |
| LastError | Last error reported (Numerical value) |
| Error_Description | Last error reported (String value) |
| Timer_Interval | Timer interval in ms |

Each object that is a descendent of TInstrument runs in its own separate thread, independently of the other TInstrument objects. So, every instrument is monitored, closed, and restarted separately in case of trouble.

Digital I/O Controller

Since a digital I/O card functions as intermediate hardware between the software and other pieces of hardware of the system (valve system and transfer mirror positioning system) outside the computer, a digital I/O controller administers its resources. This controller controls the interaction of other controllers that requires the use of a digital I/O card (see, FIG. 15). When a port is programmed as an output, one can return the data that the port is outputting by reading the same location.

The following is the TDigital_IO class definition (ancestor: TInstrument):

1. Additional methods or procedures
   - SetPortMode
   - SetPin
   - GetPin
   - ReservePins
   - ReleasePins
2. Additional callback procedures or events
   - (None)
3. Additional properties or data members
   - PortAPinState
   - PortBPinState
   - PortCPinState "TDigital_IO" class is a descendent of TInstrument. The additional members and properties added to the TDigital_IO class allow the individual control and verification of each digital I/O port and they assign each port in groups to other components that require a digital I/O card (see Table 6).

TABLE 6

TDigitalIO's Class Description

| Method | Description |
| --- | --- |
| SetPortMode | Sets ports A, B and C for input or output |
| SetPin | Sets an output port to 0 or 1 |
| GetPin | Gets the state of a port |
| ReservePins | Reserves I/O ports so no other instrument using a TDigitalIO object can access them |
| ReleasePins | Releases the I/O ports reserved by an instrument |

| Property | Description |
| --- | --- |
| PortAPinState | Stores the 8 pin state of port A |
| PortBPinState | Stores the 8 pin state of port B |
| PortCPinState | Stores the 8 pin state of port C |

Gas Handling System Controller

The gas handling system preferably has four control valves (see, FIG. 4). These four valves dictate the type and the path of the gas flowing through the gas cell and the system. As discussed previously (see, FIG. 8) the gas handling system relies heavily on the digital I/O controller to set and retrieve the status of all the valves in the system. For this reason the gas handling system object requires communication with the TDigital_IO object class.

The TGasHandling class definition is as follows (ancestor: TInstrument):

1. Additional methods or procedures
   MapValve
   DefineStates
2. Additional callback procedures or events
   (None)
3. Additional properties or data members
   Valve
   State
   DigitalIO The TGasHandling class requires only a few additions to the TInstrument class. This class model allows the mapping of the different valves with their respective I/O port and state. After the mapping is done, it only requires specifying the desired state of the gas handling system for this class to turn on and off the required valves. Table 7 shows TGasHandling's class description.

TABLE 7

TGasHandling's Class Description

| Method | Description |
| --- | --- |
| MapValve | Maps a valve to a specific bit port of the digital I/O controller |
| DefineStates | Defines the different states of the gas handling system |

| Property | Description |
| --- | --- |
| Valve | Sets and inquires the state of each valve individually |
| State | Sets and inquires the state of the gas handling system |
| DigitalIO | Points to the TDigital_IO object class |

Emergency Shutdown Controller

The emergency shutdown is preferably a simple controller. Its primary function is to inform the computer that the emergency shutdown has been activated. This information is received through a digital I/O port. Therefore, this control also requires using the TDigital_IO object class to monitor the state of the port connected to the emergency shutdown button.

The "TEmergencyButton" (ancestor: TInstrument) class takes care of monitoring the port where the emergency button is connected and of calling the event "OnEmergency" in case the emergency button has been activated, as follows:

1. Additional methods or procedures
   MapEmergencyButton
2. Additional callback procedures or events
   OnEmergency
3. Additional properties or data members
   State
   DigitalIO Table 8 shows the TEmergencyButton class description.

TABLE 8

TEmergencyButton Class Descriptor

| Method | Description |
| --- | --- |
| MapEmergecyButton | Maps the emergency button to a specific bit port of the digital I/O controller |

| Event | Description |
| --- | --- |
| OnEmergency | Called when the emergency button is activated |

| Property | Description |
| --- | --- |
| State | Inquires the state of the gas handling system |
| DigitalIO | Points to the TDigital_IO object class |

Purge Box Movable Mirrors Controller

The purge box controller also requires interacting with a TDigital_IO object class to command the purge box hardware to move the mirrors in and out or to find their position. The "TPurgeBox" (ancestor: TInstrument) class maps the required I/O ports to control the purge box hardware, as follows:

1. Additional methods or procedures
   MapPurgeBox
2. Additional callback procedures or events
   OnMirrorsIn
   OnMirrorsOut
3. Additional properties or data members
   State
   DigitalIO Table 9 shows TPurgeBox class description.

TABLE 9

TPurgeBox Class Descriptor

| Method | Description |
| --- | --- |
| MapPurgeBox | Maps the purge box input and output ports to a specific bit port of the digital I/O controller |

| Event | Description |
| --- | --- |
| OnMirrorsIn | Called when the mirrors go from the out to the in position |
| OnMirrorsOut | Called when the mirrors go from the in to the out position |

TABLE 9-continued

TPurgeBox Class Descriptor

| Property | Description |
|---|---|
| State | Inquires the position of the mirrors (in, out or moving) |
| DigitalIO | Points to the TDigital_IO object class |

Temperature Controller

A temperature controller controls the temperature of the gas cell. This temperature controller is preferably programmed and controlled through a serial communication port. The temperature controller enables a computer or PLC to read and write directly to registers containing the controller's parameters by using the controller's protocol.

The protocol is preferably a messaging structure, widely used to establish master-slave communication between intelligent devices. A message sent from a master to a slave contains the address of the slave, the "command" (e.g., "read register" or "write register"), the data, and a check sum (LRC or CRC).

Since the protocol is a messaging structure, it is independent of the underlying physical layer. It is preferably implemented using a traditional RS232, RS422, or RS485 over a variety of media (e.g., fiber, radio, cellular, etc.).

Messages are sent between the computer and the controller. These messages are sent in packets that are delimited by a pause for as long as the time it takes to send, e.g., 30 bits. Each message packet preferably begins with a one-byte controller address, e.g., from 0x01 to 0xF7. The second byte in the message packet identifies the message command: e.g., read (0x03 or 0x04); write (0x06 or 0x10); or loop back (0x08). The next n bytes of the message packet preferably contain register addresses and/or data. The last two bytes in the message packet contain a two-byte cyclical redundancy checksum ("CRC") for error detection. FIG. 16 shows the format of a controller packet.

The format of the register and/or data of a controller package varies depending on the command sent to the controller.

The "read" command follows the syntax shown in FIG. 17.

And, the answer to this command from the RTU unit follows the syntax shown in FIG. 18.

Since the communication from the computer to the temperature controller requires a special protocol, a "MODBUSSocket" object is provided to deal exclusively with the communication between the computer and the temperature controller (see, FIG. 19).

Spectrometer Controller

The spectrometer controller is the most important part of the system. All the data used for the gas analysis comes from the spectrometer. The spectrometer controller is in constant communication with the spectrometer. It sends commands, retrieves and processes the spectral data from the instrument and verifies the status of the spectrometer, and validates energy throughput of the infrared source and detector. The "TSpectrometer" (ancestor: TInstrument) class definition is as follows (also see Table 10):

1. Additional methods or procedures
   StartCollection
   StopCollection
   Collect
   ConvertToFormat
2. Additional callback or procedures or events
   OnBeforeCollectBackground
   OnAfterCollectBackground
   OnBeforeCollectSample
   OnAfterCollectSample
3. Additional properties or data members
   FirstXValue            FinalSpectraFormat
   LastXValue             Spectra
   ApodizationType        Background
   PhaseCorrectionApodizationType   Sample
   NumPhaseCorrectionPoints         Absorbance
   CollectionLoop

TABLE 10

TSpectrometer's Class Description

| Method | Description |
|---|---|
| StartCollection | Starts scanning a new spectra |
| StopCollection | Stops scanning the current spectra |
| Collect | Retrieves spectra from spectrometer |
| ConvertToFormat | Converts a spectra format to another spectra format |

| Event | Callback Procedure Description |
|---|---|
| OnBeforeCollectBackground | Called before a background spectra is collected |
| OnAfterCollectBackground | Called after a background spectra is collected |
| OnBeforeCollectSample | Called before a sample spectra is collected |
| OnAfterCollectSample | Called after a sample spectra is collected |

| Property | Description |
|---|---|
| FirstXValue and LastXValue | Specifies the frequency range in wavenumbers (in $cm^{-1}$) to be covered by the conversion of the spectra from a time domain format to a frequency domain format |
| ApodizationType | Type of apodization used for the conversion of the spectra from time domain to frequency domain |
| PhaseCorrection ApodizationType | Type of apodization used for the phase correction of the spectra |
| NumPhaseCorrectionPoints | Number of points used from the original spectra to perform a phase correction of the spectra |
| CollectionLoop | If true, this will start a new spectra scanning immediately after the last spectra scanning is done |
| FinalSpectraFormat | Specifies the final format of the spectra |
| Spectra | Stores the spectra Interferogram |
| Background | Stores the background spectra |
| Sample | Stores the sample spectra |
| Absorbance | Stores the absorption spectra of the sample spectra with respect to the background spectra |

The present invention encapsulates a function call library to simplify and provide a more standard interface to access the spectrometer. The class TSpectrometer controls the spectrometer. Like the rest of the instruments, TSpectrometer is also a child class derived from TInstrument.

1. Additional methods or procedures
   LoadSpectra
   SaveSpectra
   I2SingleBeam
   CalcAbsorbance Absorbance2Transmission
Transmission2Absorbance 2. Additional properties or data members
   Format
   Apodization
   PhaseApodization
   Resolution
   NumScans
   PathLength
   FirstPoint
   LastPoint
   MaxLaserFrequency
   NumDataPoints
   NurhPhasePoints
   StepSize The "TSpectraData" class stores and manipulates the spectral data, as follows: (also see Table 11): The spectral manipulation includes the math to transform an interferogram into a single beam spectrum, or a single beam spectrum into a transmission or absorption spectrum base on a background or reference spectrum.

TABLE 11

TSpectraData Class Description

| Method | Description |
| --- | --- |
| LoadSpectra | Loads Spectra file from disk |
| SaveSpectra | Saves Spectra File to disk |
| I2SingleBeam | Transforms an Interferogram into a single beam spectra |
| CalcAbsorbance | Calculates the absorption spectra based on a background spectra |
| Absorbance2Transmission | Transforms an absorption spectra into a transmission spectra |
| Transmission2Absorbance | Transforms a transmission spectra into an absorption spectra |

| Property | Description |
| --- | --- |
| Format | Describes the spectrum format (interferogram, single beam, absorption, transmission) |
| Apodization | Describes the apodization used to convert this spectrum from an interferogram to a single beam spectrum |
| PhaseApodization | Describes the apodization used for the phase correction calculation of the spectra |
| Resolution | Describes the spectrometer resolution used during the scanning of the spectra |
| NumScans | Describes the numbers of scans used to obtain a spectrum |
| PathLength | Describes the path length of the gas cell used to collect a spectrum |
| FirstPoint | Specifies the first x coordinate point in wavenumbers (in $cm^{-1}$) of the first data point |
| LastPoint | Specifies the last x coordinate point in wavenumbers (in $cm^{-1}$) of the last data point |
| MaxLaserFrequency | Describes the maximum sampling frequency |
| NumDataPoints | Specifies the number of spectral data points |
| NumPhasePoints | Specifies the number of points used to calculate the phase correction of the spectrum |
| StepSize | Specifies the separation between spectral points is uniformly distributed, and StepSize specifies the distance between points (in $cm^{-1}$) |

System Integration

As discussed previously, the present invention is divided into two main processes (see, FIG. 6). Process 1 controls and synchronizes the hardware and Process 2 handles and manipulates the spectral data to produce the quantitative analysis. Processes 1 and 2 each run in its own thread, independent of each other. Process 1 stores the collected interferogram into a queue, and Process 2 monitors this queue and then removes and processes the interferograms stored in the queue.

In order to control the hardware, Process 1 follows a simple flow diagram (see, FIG. 6) on each state of the flow diagram, Process 1 commands each instrument involved in that stage to execute a specific task. Since each instrument controller is self contained, Process 1 does not need to keep interacting with each controller to complete the assigned task. It only needs to wait until all the commanded controllers have completed the assigned tasks to continue to the next stage of the flow diagram.

Each commanded controller reports to Process 1 on the success or failure of the task that each specific controller was assigned to perform.

As a precaution method, a "Watch Dog" routine is implemented into Process 1, so each controller can be monitored. This gives Process 1 the capability to detect a troubled controller and to take proper actions against the troubled controller.

The operation of Process 2 is preferably simpler. This process maintains a constant monitoring of the interferogram queue. Each time an interferogram enters the queue, Process 2 processes it and calculates the estimated concentration of the various molecular species specified by a calibration file. This calibration file contains the spectral information and concentrations of the impurities to be analyzed.

After the analysis of the impurities is performed, the results are reported, and the interferogram queue is monitored again until another interferogram is available. Then, the cycle is repeated.

Gas Analysis

Spectral Data Manipulation

The steps to convert an interferogram into a single beam spectrum are better explained by having an understanding of how a spectrometer works. The following section is a summarized review of the process based on chapters 1–3 of "Fourier Transform Infrared Spectroscopy" (see, P. R. Griffiths and J. A. de Haseth, "Fourier Transform Infrared Spectroscopy", John Wiley & Sons, New York, 1986).

Monochromatic Light Sources

Today, most of the FTIR Spectrometers are based on the two-beam interferometer originally designed by Michelson in 1891. The Michelson interferometer is a device that divides a beam of radiation into two paths and then recombines the two beams after a path difference has been introduced. A condition is thereby created under which interference between the beams occurs. The intensity variations of the beam emerging from the interferometer is measured as a function of the path difference by a detector. The simplest form of a Michelson interferometer is show in FIG. 20.

Background Discussion

The interferometer has two mutually perpendicular plane mirrors, one of which can move along an axis that is perpendicular to its plane. The movable mirror moves at a constant velocity. Between the fixed mirror and movable mirror is a beamsplitter, where a beam of radiation from an external source is partially reflected to the fixed mirror (at point F) and partially transmitted to the movable mirror (at point M). The variation in intensity of the beam passing to the detector and returning to the source as a function of the path difference ultimately yields the spectral information in a Fourier transform spectrometer.

The path difference between the beams traveling to the fixed and movable mirrors is 2(OM-F); (see, FIG. 20). This optical path difference is called the retardation and is usually given the symbol δ. When the fixed mirror and the movable mirror are equidistant from the beamsplitter (zero retardation), the two beams are perfectly in phase on recombination with the beamsplitter. At this point, the beams interfere constructively.

The following discusses an idealized situation where a source of monochromatic radiation produces an infinitely narrow and perfect collimated beam. The wavelength of the radiation is λ (in centimeters) and its wavenumber is $\bar{v}$ (reciprocal centimeters). If the movable mirror is moved a distance of ¼λ, the retardation is now ½λ; and the recombination of the beams at the beamsplitter is out of phase and interfere destructively.

If the mirror is moved at a constant velocity, the signal at the detector is seen to vary sinusoidally, with a maximum being registered each time that the retardation is an integer multiple of λ. The intensity at any point where δ=nλ (where n is an integer) is equal to the intensity of the source (/($\bar{v}$)). At other values of δ, the intensity of the beam at the detector, is given by:

$$I'(\delta)=0.5I(\bar{v})\{1+\cos 2\pi\bar{v}\delta\} \quad \text{Equation 2}$$

It can be seen that I'(δ) is composed of a constant (dc) component and a modulated (ac) component. Only the ac component is important in spectrometric measurements. The interferogram from a monochromatic source measured with an ideal interferometer is given by:

$$I(\delta)=0.5I(\bar{v})\cos 2\pi\delta \quad \text{Equation 3}$$

In practice, the amplitude of an interferogram as observed after detection is proportional not only to the intensity of the source but also the beamsplitter efficiency, detector response, and amplifier characteristics. Of these factors, only I($\bar{v}$) varies from one measurement to the next for a given system configuration, while the others factors remain constant. Therefore, Equation 3 may be modified by a single wavenumber-dependent correction factor, H($\bar{v}$), to give:

$$I(\delta)=0.5H(\bar{v})I(\bar{v})\cos 2\pi\delta, \quad \text{Equation 4}$$

where 0.5 H($\bar{v}$)/($\bar{v}$) may be set equal to B($\bar{v}$), the single-beam spectral intensity. The simplest equation representing the interferogram is, therefore:

$$I(\delta)=B(\bar{v})\cos 2\pi\delta \quad \text{Equation 5}$$

Polychromatic Sources

In the particular case where the spectrum of a source of monochromatic radiation is to be determined, performing the Fourier transform of a measured interferogram is a trivial operation. However, if the source emits several discrete spectral lines or continuous radiation, the interferogram is more complex. For a monochromatic source, the envelope of the interferogram has an infinitely large width (i.e. it will be a pure cosine wave). Conversely, for broadband spectral sources, the decay is very rapid.

When the source is a continuum, the interferogram is represented by the integral:

$$I(\delta) = \int_{-\infty}^{+\infty} B(\bar{v})\cos 2\pi\bar{v}\delta d\bar{v} \quad \text{Equation 6}$$

which is one-half of a cosine Fourier transform pair, the other being:

$$B(\bar{v}) = \int_{-\infty}^{+\infty} I(\delta)\cos 2\pi\bar{v}\delta d\delta \quad \text{Equation 7}$$

It may be noted that I(δ) is an even function, so that Equation 7 may be rewritten as:

$$B(\bar{v}) = 2\int_{0}^{+\infty} I(\delta)\cos 2\pi\bar{v}\delta d\delta \quad \text{Equation 8}$$

Equation 6 shows that one can measure the complete spectrum from 0 to +∞ (in reciprocal centimeters) at infinitely high resolution. However, Equation 8 shows that in order to achieve this, one has to scan the moving mirror of the interferogram an infinitely long distance. The effect of measuring the signal over a limited retardation is to cause the spectrum to have a finite resolution.

Apodization

The resolution of a spectrum measured interferometrically depends on the maximum retardation of the scan. Thus, if the maximum retardation of an interferometer is $\Delta_{max}$, the best resolution that one can obtain using this interferometer, $\Delta\bar{v}$, is given by:

$$\Delta\bar{v}=(\Delta_{max})^{-1} \quad \text{Equation 9}$$

By restricting the maximum retardation of the interferogram to Δ centimeters, one is effectively multiplying the complete interferogram by a truncation function, D(δ), which is unity between δ=−Δ and +Δ, and zero at all other points—that is:

$$D(\delta) = \begin{cases} 1 & \text{if } -\Delta \leq \delta \leq +\Delta \\ 0 & \text{if } \delta|\Delta| \end{cases} \quad \text{Equation 10}$$

In view of the shape of this function, D(δ) is often called a boxcar truncation function. By analogy to Equation 8, the spectrum in this case is given by the equation:

$$B(\bar{v}) = 2\int_{0}^{+\infty} I(\delta)D(\delta)\cos 2\pi\bar{v}\delta d\delta \quad \text{Equation 11}$$

The effect of multiplying I(δ) by the boxcar function D(δ) is to yield a spectrum on Fourier transformation that is the convolution of FT (Fourier transform) of I(δ) measured with an infinitely long retardation and the FT of D(δ). The FT of I(δ) is the true spectrum, B($\bar{v}$), while the FT of D(δ), f($\bar{v}$), is given by:

$$f(\bar{v}) = \frac{2\Delta\sin(2\pi\bar{v}\Delta)}{2\pi\bar{v}\Delta} \quad \text{Equation 12}$$
$$\equiv 2\Delta\text{sinc}(2\pi\bar{v}\Delta)$$

When a spectrum is measured on a monochromator, the true spectrum is convoluted with the triangular slit function of the monochromator. This situation with FT-IR spectrometry is equivalent, except that the true spectrum is convoluted with the sine function f($\bar{v}$). Since the FT-IR spectrometer does not have any slits, f($\bar{v}$) has been called the instrumental line shape ("ILS") function. The sine x function is not a particularly useful line shape for infrared spectrometry in view of its fairly large amplitude at wavenumbers well away from $\bar{v}$. The first minimum reaches below zero by an amount that is 22% of the height at $\bar{v}$. If a second weak line happens to be present in the spectrum at the frequency of this minimum, it is not be seen in the computed spectrum. One method of circumventing the problem of these secondary minima is through the process known as apodization.

If instead of using the boxcar function, one uses a simple weighting function of the form:

$$A_1(\delta) = \begin{cases} 1 - \left|\frac{\delta}{\Delta}\right| & \text{for } -\Delta \leq \delta \leq \Delta \\ 0 & \text{for } \delta > |\Delta| \end{cases} \qquad \text{Equation 13}$$

the true spectrum would be convoluted with the Fourier transform of $A_1(\delta)$, and this function would, therefore, determine the ILS. The Fourier transform of $A_1(\delta)$ has the form:

$$f_1(\bar{v}) = \Delta \text{sinc}^2(\pi\bar{v}\Delta) \qquad \text{Equation 14}$$

By using this ILS, the amplitude of the side lobes that the spectrum presents due to the ILS function are considerably reduced from the amplitude of the side lobes of a sine function. Suppression of the magnitude of these oscillations is known as apodization. The function $A_1(\delta)$ is called triangular apodization function and is the most common apodization function used in infrared Fourier transform spectrometry.

Phase Correction

Up to this point, it has been assumed that Equations 6 and 8 give an accurate representation of the interferogram. In practice, an additional term often has to be added to the phase angle, $2\pi\bar{v}\delta$, to describe the actual measured interferogram. Correction to the phase angle may arise due to optical, electronic, or sampling effects. Two common examples that lead to a change of the cosine term of these equations follow:

1. If one makes use of the fact that the interferogram as represented by Equation 6 is symmetric about $\delta=0$, but that the first data point is actually sampled before the zero retardation point, at $\delta=-\epsilon$, the interferogram takes the form:

$$I(\delta) = \int_0^{+\infty} B(\bar{v})\cos 2\pi\bar{v}(\delta - \varepsilon)d\bar{v} \qquad \text{Equation 15}$$

2. Electronic filters designed to remove high-frequency noise from the interferogram have the effect of putting a wavenumber-dependent phase lag, $\theta_{\bar{v}}$, on each cosinusoidal component of the interferogram, and the resulting signal is given by:

$$I(\delta) = \int_0^{+\infty} B(\bar{v})\cos(2\pi\bar{v}\delta - \theta_{\bar{v}})d\bar{v} \qquad \text{Equation 16}$$

Since any cosine wave $\cos(\alpha-\beta)$ can be represented by:

$$\cos(\alpha-\beta) = \cos \alpha \cdot \cos \beta + \sin \alpha \cdot \sin \beta \qquad \text{Equation 17}$$

the addition of a second term to the phase angle, $2\pi\bar{v}\delta$, has the effect of adding sine components to the cosine wave interferogram. Two properties of sine and cosine waves are important in this respect:

(a) $\cos \theta$ and $\sin \theta$ are orthogonal \qquad Equation 18

(b) $\cos \theta - i \sin \theta = e^{-i\theta}$

In light of this relationship (Euler's equation), Equation 16 may be rewritten in the transcendental exponential notation (see, C. T. Foskeft, Transform Techniques in Chemistry, Plenum Publishing, New York, 1978) as:

$$I(\delta) = \int_0^{+\infty} B(\bar{v})e^{2\pi\bar{v}\delta}\,d\bar{v} \qquad \text{Equation 19}$$

For this representation, $I(\delta)$ and $B(\bar{v})$ are said to be linked through the complex Fourier transform. To recover $B(\bar{v})$ from $I(\delta)$ the inverse complex transform:

$$B(\bar{v}) = \int_{-\infty}^{+\infty} I(\delta)e^{-2\pi\bar{v}\delta}\,d\delta \qquad \text{Equation 20}$$

is performed. The process of removing these sine components from the interferogram, or removing their effects from a spectrum, is known as phase correction.

When a recorded interferogram $I(\delta)$ is transformed to produce a spectrum $B'(\bar{v})$, a complex Fourier transform must be used unless the interferogram is symmetric. Hence, from Equation 20, after transformation, $B'(\bar{v})$ is calculated by the complex addition:

$$B'(\bar{v}) = Re(\bar{v}) + iIm(\bar{v}) \qquad \text{Equation 21}$$

where $Re(\bar{v})$ and $Im(\bar{v})$ are the real and imaginary parts of $B'(\bar{v})$, respectively. If $I(\delta)$ is symmetrically sampled (i.e. there is an equal number of points on both sides of the centerburst), we can calculate the magnitude spectrum of $B'(\bar{v})$, which is denoted $|B'(\bar{v})|$:

$$|B(\bar{v})| = \{Re(\bar{v})^2 + Im(\bar{v})^2\}^{1/2} \qquad \text{Equation 22}$$

The magnitude spectrum exhibits zero phase error but has noise nonlinearities. The magnitude (Equation 22) and the complex spectra (Equation 21) are related by the phase angle $\theta_{\bar{v}}$:

$$B'(\bar{v}) = |B(\bar{v})|e^{i\theta_{\bar{v}}} \qquad \text{Equation 23}$$

The complex spectrum $B'(\bar{v})$ contains all the spectral information, but it is dispersed into two complex planes by the phase. The true spectrum $B(\bar{v})$ lacks the noise nonlinearities of the magnitude spectrum. The object of phase correction is to produce the true spectrum $B(\bar{v})$. Since $\theta_{\bar{v}}$ usually varies slowly with wavenumber, it is possible to factor $e^{i\theta_{\bar{v}}}$ from Equation 23. In this case:

$$B(\bar{v}) = B'(\bar{v})e^{-i\theta_{\bar{v}}} \qquad \text{Equation 24}$$
$$= Re(\bar{v})\cos\theta_{\bar{v}} + Im(\bar{v})\sin\theta_{\bar{v}}$$

When $e^{i\theta_{\bar{v}}}$ is transposed from one side to the other of equation Equation 24, only the real terms are retained from the trigonometric expansion; because the true and amplitude spectra are real functions. Equation 24 represents a phase correction algorithm for double-sided interferograms and the phase angle is calculated as shown:

$$\theta_{\bar{v}} = \arctan\frac{\operatorname{Im}(\bar{v})}{\operatorname{Re}(\bar{v})} \qquad \text{Equation 25}$$

The phase angle is, in practice, a slowly varying function with wavenumber; therefore $\theta_{\bar{v}}$ does not need to be measured to a high resolution. The phase angle is adequately calculated from a short, symmetrically-sampled interferogram and subsequently applied to a much higher resolution spectra. Therefore, an asymmetrically-sampled interferogram is collected as long as there is a short symmetrically-sampled portion that provides the phase angle. Mertz developed this method of phase correction (see, L. Mertz, Transformations in Optics, Wiley, New York, 1965; L. Mertz, Infrared Physics 7, 17, 1967).

Mertz Method

The calculation of the spectra is based on the Mertz method to calculate the true spectrum (or single beam spectrum). Its steps can be summarized as follow:

Collect sample interferogram I;
From I obtain a short double-side interferogram I';
Apply apodization function $A(\delta)$ to I';
Rotate interferogram I' to zero phase;
Calculate the complex spectrum $B'_s(\bar{v})$ FFT of I';
Calculate the phase curve $\theta_{\bar{v}}$ from $B'_s(\bar{v})$;
Calculate and interpolate the cosine and sine values of the phase curve $\theta_{\bar{v}}$ to full resolution;
Apply apodization function $A(\delta)$ to I;
Calculate the complex spectrum $B'(\bar{v})$ by using FFT over I; and
Finally calculate the true spectrum $B(\bar{v})$ from the cosine and sine values of the phase curve $\theta_{\bar{v}}$ and the complex spectrum $B'(\bar{v})$.

For a complete pictorial example of obtaining the true spectrum, (see, P. R. Griffiths and J. A. de Haseth, "Fourier Transform Infrared Spectroscopy", John Wiley & Sons, New York, 1986).

The only thing left to do is to calculate the absorption spectrum $A(\bar{v})$. As mentioned previously, the absorption spectrum is calculated based on the single beam background spectrum $B_s(\bar{v})$ and the single beam sample spectrum $S_s(\bar{v})$.

The absorption spectrum is defined as:

$$A(\bar{v}) = -\log_{10}(T(\bar{v})/100) \qquad \text{Equation 26}$$

where $T(\bar{v})$ is the ratio of the transmittance spectrum of the sample spectrum over the background spectrum as follows:

$$T(\bar{v}) = \frac{S_s(\bar{v})}{B_s(\bar{v})} * 100 \qquad \text{Equation 27}$$

So, one can rewrite Equation 26 into:

$$A(\bar{v}) = \log_{10}\left(\frac{B_s(\bar{v})}{S_s(\bar{v})}\right) \qquad \text{Equation 28}$$

which gives the absorption spectrum.

Quantification Analysis

Beer's Law

The Beer-Lambert relationship (or Beer's law) states that the concentration C is directly proportional to the absorbance A. Generally, this relationship is more often applied by comparing the height of a maximum absorption peak of a reference gas to the height of the corresponding peak in a sample spectrum. However, this technique suffers if the baseline is not accurately known, and it fails completely in those cases where an individual spectral feature of a sample is below the noise level. These problems are reduced if the proper least square fitting routines are applied to the data.

The application of any least square method to multicomponent quantitative infrared analysis requires a known relationship. Beer's law provides this required relationship. That is:

$$A = abC \qquad \text{Equation 29}$$

where a is the absorptivity and b is the pathlength.

Multivariate calibration methods have had a major impact on the quantitative analysis of infrared spectral data. They have been shown to improve analysis precision, accuracy, reliability, and applicability for infrared spectral analyses relative to the more conventional univariate methods of data analysis. Rather than attempting to find and use only an isolated spectral feature in the analysis of spectral data, multivariate methods derive their power from the simultaneous use of multiple intensities (i.e. multiple variables) in each spectrum. Thus, the problem of spectral interferences can be eliminated with the use of any one of the various multivariate methods. These methods include, but are not limited to, classical least squares ("CLS," also known as the K-matrix method) (see, D. M. Haaland, R. G. Easterling, D. A. Vopicka, "Multivariate Least-Squares Methods Applied to Quantitative Spectral Analysis of Multicomponents Samples", Applied Spectroscopy, Volume 39, pp. 73–84, 1985); inverse least square ("ILS," also known as the P-matrix method) (see, H. J. Kisner, C. W. Brown, and G. J. Kavamos, "Multiple Analytical Frequencies and Standards for the Least-Square Spectrometric Analysis of Serum Lipids", Analytical Chemistry, Volume 55, pp. 1703–1707, 1983); the Q-matrix method (see, G. L. McClure, P. B. Roush, J. F. Williams, and C. A. Lehmann, "Application of Computerized Quantitative Infrared Spectroscopy to the Determination of the Principal Lipids Found in Blood Serum", Computerized Quantitative Infrared Analysis (G. L. McClure ed), pp. 131–154, ASTM Special Publication 934, 1987); cross correlation (see, C. K. Mann, J. R. Goleniewski, and C. A. Sismanidis, "Spectrophotometric Analysis by Cross-Correlation", Applied Spectroscopy, Volume 36, pp. 223–229, 1982); Kalman filtering (see, S. L. Monfre and S. D. Brown, "estimation of Ester Hydrolysis Parameters by Using FTIR Spectroscopy and the Extended Kalman Filter", Analytical Chemistry, Volume 200, p. 397, 1988), partial least square (PLS) (see, D. M. Haaland and E. V. Thomas, "Partial Least-Square Methods for Spectral Analysis", Analytical Chemistry, Volume 60, pp. 1193–1202, 1988), and principal component regression ("PCR") (see, D. M. Haaland and E. V. Thomas, "Partial Least-Square Methods for Spectral Analysis", Analytical Chemistry, Volume 60, pp. 1193–1202, 1988). The more heavily used multivariable calibration methods in infrared spectroscopy are CLS, ILS, PLS and PCR. According to D. M. Haaland, "Multivariate Calibration Methods Applied to the Quantitative Analysis of Infrared Spectra", Computer-Enhanced Analytical Spectroscopy, Volume 3, New York, 1992, CLS, PLS and PCR almost always outperform the frequency limited ILS method. This is because the full-spectrum methods take advantage of the signal averaging effect obtained when multiple intensities with redundant information are included in the analysis. The standard CLS method performs almost as good as the other methods. By recommendation of Haaland (see, D. M. Haaland, Private Communcation, Spring of '98), a variation of the CLS method is believed to outperform PLS and PCR. This method is a multi-band, multi-component weighted analysis version of the CLS and is based on the work of Haaland, (see, D. M. Haaland and R. G. Easterling, "Improved Sensitivity of Infrared Spectroscopy by the Application of Least-Square Methods", Applied Spectroscopy, Volume 34, Number 5, pp. 539–548, 1980; D. M. Haaland and R. G. Easterling, "Application of New Least-Square Methods for the Quantitative Infrared Analysis of Multicomponent Samples", Applied Spectroscopy, Volume 36, Number 6, pp. 665–673, 1982; David M. Haaland, "Multivariate Calibration Methods Applied to Quantitative FT-IR Analyses", Practical Fourier Transform Infrared Spectroscopy, Chapter 8, 1990). This method is preferably used for all the quantification analyses.

Weighted Multi-band CLS

Least-square regression analysis methods have been applied broadly to the quantitative analysis of infrared spectra. Early least-square methods fit Gaussian or Lorentzian peak shapes to spectra, but these band shapes are not general and hence not as accurate as other criteria. One procedure of least-square curve fitting was presented by Antoon et al (see, M. K. Antoon, J. H. Koenig, Applied Spectroscopy, Volume 31, p. 518, 1977). In this method, no prescribed band shapes were fit to spectra; rather standard spectra were fit to the mixture. CLS involves using mixtures of known compositions as the standard and calculating the concentration of unknown mixtures directly. It is possible to write Beer's law (Equation 29) as:

$$A = kc \qquad \text{Equation 30}$$

where k is equal to the product of the absorptivity (a) and the pathlength (b). For multicomponent systems, absorbances are additive, so the total absorbance at a single wavenumber is:

$$A = \sum_{i=1}^{I} k_i c_i + e \qquad \text{Equation 31}$$

where $k_{ij}$ is the proportionality constant for the $I^{th}$ component, $c_i$ is its concentration, I is the number of components and e is the random error. A series of such equations may be written for each wavelength in a spectrum:

$$A_j = \sum_{i=1}^{I} k_{ji} c_i + e_j \quad j = 1, 2, \cdots, n \qquad \text{Equation 32}$$

where $A_j$ is now the absorbance at the $j^{th}$ wavenumber, $k_{ji}$ is the proportionality constant at the $j^{th}$ wavenumber for the $I^{th}$ component and $e_j$ is the random error at the $j^{th}$ wavenumber. The error is assumed to be normally distributed with the expectation of zero. The full spectrum then yields a series of n equations, where n is the number of frequencies. These may be put into matrix form:

$$A = KC + E \qquad \text{Equation 33}$$

where

A is the n×m matrix whose columns represent the spectrum of each of the m standard mixtures, K is the n×I matrix whose columns represent the I pure-component spectra at unit concentration and unit relative pathlength, C is the I×m matrix of the known component concentrations, and E is the n×m matrix of the random measured errors in the spectra.

The least-square estimate of the matrix of pure-component spectra $\hat{K}$ is given by:

$$\hat{K} = AC^T(CC^T)^{-1} \qquad \text{Equation 34}$$

This is the simplest solution. The matrix to be inverted in Equation 34 is a small I×I matrix, and this inversion is performed readily with a computer. Therefore, as many frequencies as desired can be added without increasing the size of the matrix to be inverted.

It is assumed that E is a noise matrix that is a random observation from a probability distribution that has a mean of zero and a variance of $\sigma^2 V$, where V is a known n×n matrix and $\sigma^2$ can be estimated from the spectral residuals.

In the analysis of an unknown sample, the matrix $\hat{K}$ is used for concentration prediction of a sample spectrum as a vector of dimension n×1. The matrix $\hat{K}$ can also be augmented by a column of ones to account for spectral offsets, a column of evenly incremented values for linear baselines, and a column of squared values for quadratic baseline corrections to the model. The latter two columns should be mapped from −1 to 1 to provide better computational precision. The model for predicting sample concentration from the unknown sample spectrum, is then:

$$a = \hat{K}c + e \qquad \text{Equation 35}$$

The weighted least-squares estimate of sample concentrations, c, is:

$$c = (\hat{K}^T V^{-1} \hat{K})^{-1} \hat{K}^T V^{-1} a \qquad \text{Equation 36}$$

and the unknown $\sigma^2$ is estimated by:

$$\hat{\sigma}^2 = \frac{(aV^{-1}a^T) - c^T(\hat{K}^T V^{-1} a)}{n - m} \qquad \text{Equation 37}$$

It is assumed that the errors are independent but with different variances at each wavenumber for each spectrum. In this case, V is diagonal and can be easily inverted by inverting its diagonal elements. The diagonal elements of V are estimated for each sample spectrum a by using the elements $a_j$ at each wavenumber j as the diagonal elements of V, since the variance of the shot noise increases directly with the spectral intensity.

The above CLS prediction can be performed separately for each spectral band w. The result is a series of w concentrations for each component in the w bands. The final calculated concentrations for each analyte are formed by a weighted average of concentrations found for each analyte in each band. The least-squares estimated concentration for component i in the band w is $c_{wi}$. The matrix $(\hat{K}^T V^{-1} \hat{K})_w^{-1}$ is used to estimate the variance of $c_{wi}$. Let $s_{wj}$ be the $j^{th}$ diagonal element of $(\hat{K}^T V^{-1} \hat{K})_w^{-1}$ corresponding to $c_{wi}$. This diagonal element represents the inverse of the summary net-analyte signal for component i. An estimate of $\sigma^2$ per band w, i.e. $\hat{\sigma}_w^2$, is calculated using Equation 37. $\hat{\sigma}_w^2$ represents a summary statistic proportional to the squared spectral residual in band w for the sample spectrum. The method to estimate the relative concentration of component i in the mixture is to take a weighted average of the concentration $c_{wi}$, where the weight is the reciprocal of the products of $S_{wj}$ and $\hat{\sigma}_w^2$. The reported summary concentration for component i from all bands is given by:

$$c_i = \frac{\sum_{j=1}^{w}\left(\frac{c_{ij}}{s_j^i * \sigma^2}\right)}{\sum_{j=1}^{w}\left(\frac{1}{s_j^i * \sigma^2}\right)} \quad i = 1, 2 \ldots 1 \qquad \text{Equation 38}$$

Equation 38 gives highest weight to those bands where component i has its largest net-analyte signals and also exhibits small spectral residuals; i.e. those bands that follow Beer's linear additive model and all the components within those bands are included in the calibration model. Thus, this weighted average concentration is a statistically efficient measure of the $I^{th}$ component concentration.

Noise and Spectrometer Drift Reduction

For any spectrometer, conventional or interferometric, the SNR of a spectrum measured at a given resolution is proportional to the square root of the measured time. The relationship between the SNR and $t^{1/2}$ holds in FT-IR spectrometry (see, S. Wolf and R. N. Tauber, Silicon Processing for VLSI Era, Volume 1, Lattice Press, California, 1986, pp. 345, 378). For measurements made with a rapid scanning interferometer operating with a certain mirror velocity at a given resolution, SNR therefore increases with the square root of the number of scans being averaged. Note that SNR of a spectrum measured using a single one second scan may be increased by an order of magnitude by averaging 100 scans in a time of less than 2 min. To increase the SNR by another order of magnitude necessitates averaging 10,000 scans, takes about three hours.

The collection of spectra over a long period of time has certain problems. One of these problems is the non-linear fluctuation of the spectra baselines over time due to spectrometer drift. Another source of problem is the small changes in concentration of the impurities present inside the spectrometer due to changes in impurity level in the purging gas or due to impurities absorbed on the inside walls of the spectrometer that are desorbed back into the volume (such as moisture due to changes in temperature). Even changes in the atmospheric pressure perturb the baselines of the spectra.

To compute the absorption spectra of a. particular sample, one needs the background spectra of the instrument and the spectra of that particular sample. As mentioned previously, changes in concentration of impurities inside the spectrometer and spectrometer drift affect the baselines of the absorption spectra. These changes shorten the life and usability of the collected background spectra.

The transmittance spectra are defined as follows:

$$T = \frac{S}{B} \qquad \text{Equation 39}$$

where T is the transmittance, B is the background spectra and S is the sample spectra. B basically describes the spectrometer line shape or point of reference and S this line shape minus the deviation from this line shape at certain regions due to transmittance loss produced by the absorption of the sample being analyzed.

The traditional method for collecting absorption spectra involves collecting first a background spectra $B_i$ and then collecting a sample spectra $S_k$ (where i and k represent the number of averaged scans per spectra). $B_i$ is defined as $$B_i = \begin{cases} i = 1 & \gamma + \varepsilon_1 \\ i > 1 & \gamma + \dfrac{\sum_{j=1}^{i}\varepsilon_j}{i} + \dfrac{\sum_{j=2}^{i}\Delta D_j}{i-1} \end{cases} \qquad \text{Equation 40}$$

where $\gamma$ represents the true spectrometer line shape, $\varepsilon_i$ represents the uniform distributed random noise and $\Delta D_j$ the small increment or decrement of spectral drift during the j scan. And, $S_i$ is defined as:

$$S_k = \gamma + \theta + \frac{\sum_{j=2}^{i}\Delta D_j}{i-1} + \frac{\sum_{l=1}^{k}(\Delta D_l + \varepsilon_l)}{k} \qquad \text{Equation 41}$$

where $\theta$ represents the loss of transmittance due to the sample being analyzed. By incorporating this into Equation 39 we obtain:

$$T_{i,k} = \frac{S_k}{B_i} \qquad \text{Equation 42}$$

$$T_{i,k} = \frac{\gamma + \theta + \dfrac{\sum_{j=2}^{i}\Delta D_j}{i-1} + \dfrac{\sum_{l=1}^{k}(\Delta D_l + \varepsilon_l)}{k}}{\gamma + \dfrac{\sum_{j=1}^{i}\varepsilon_j}{i} + \dfrac{\sum_{j=2}^{k}\Delta D_j}{i-1}} \qquad \text{Equation 43}$$

By calculating the limits of Equation when i and k go to infinity, one obtains Equation 44 where the average of noise $\varepsilon$ goes to 0; this shows that the effects of the noise can be eliminated but not the effects of spectrometer drift.

$$T_{i,k} = 1 + \frac{\theta + \dfrac{\sum_{l=1}^{k}\Delta D_l}{k}}{\gamma + \dfrac{\sum_{j=2}^{i}\Delta D_j}{i-1}} \qquad \text{Equation 44}$$

But, it can be bounded by:

$$\tilde{T}_T = 1 + \frac{\theta \pm D_{\max}}{\gamma \pm D_{\max}} \qquad \text{Equation 45}$$

where the spectral drift $D_{max}$, goes to any value from 0 to the maximum possible drift that the instrument can experience per scan.

If an alternating collection of x scans of backgrounds and x scans of samples are collected—that is, every other scan is a background spectrum and every other scan +1 is a sample spectrum, the $B_i$ is defined as:

$$B_i = \qquad \text{Equation 46}$$

$$\begin{cases} i = 1 & \gamma + \varepsilon_1 \\ i > 1 & \gamma + \dfrac{2\sum_{j=1}^{(i+1)/2}\varepsilon_{2j-1}}{i+1} + \dfrac{\sum_{j=2}^{i}\Delta D_j}{i-1} \quad i = 1, 3, 5, 7, 9 \ldots \end{cases}$$

and $S_i$ as $$S_k = \gamma + \theta + \frac{\sum_{j=2}^{k} \Delta D_j}{k} + \frac{2\sum_{l=2}^{k/2} \varepsilon_{2l}}{k} \quad k = i+1 \qquad \text{Equation 47}$$

and by the incorporation of Equation 46 and Equation 47 into Equation 39 one obtains:

$$T_{i,k} = \frac{\gamma + \theta + \frac{\sum_{j=2}^{k} \Delta D_j}{k} + \frac{2\sum_{l=2}^{k/2} \varepsilon_{2l}}{k}}{\gamma + \frac{2\sum_{j=2}^{(i+1)/2} \varepsilon_{2j-1}}{i+1} + \frac{\sum_{j=2}^{i} \Delta D_j}{i-1}} \qquad \text{Equation 48}$$

And, by calculating the limit of Equation 48 when i and k go to infinity, one obtains:

$$T_{i,k} = 1 + \frac{\theta}{\gamma + \frac{\sum_{j=2}^{i} \Delta D_j}{i-1}} \qquad \text{Equation 49}$$

which can be bounded by:

$$\tilde{T}_s = 1 + \frac{\theta}{\gamma \pm D_{\max}} \qquad \text{Equation 50}$$

Finally, by comparing the effects of spectral drift from Equation 45 and Equation 50 to Equation 39 one obtains:

$$|T - T_s| \leq |T - T_T| \qquad \text{Equation 51}$$

Therefore, by increasing the number of scans per spectra and using an alternating collection of spectra, one can obtain absorption spectra with a higher SNR level and reduced effects from the spectrometer drift compared to the traditional method.

Spectra Collection Time Reduction

There does not exist a way to reduce the time to take x number of scans per spectra except by using a faster type of detector. An object of the present invention is to provide a monitoring system capable of detecting changes in the level of impurities. Changes in the level of impurities can happen very slowly by (small changes) or very rapidly (big changes) over time. To detect small changes in concentration, it is necessary for the system to be able to see those changes, so the SNR level needs to be higher and a longer collection time is required. Since these changes occur slowly over time and only become significant if they go beyond a threshold or maximum acceptable impurity level, a larger number of scans per spectra can be used. On the other hand, if big changes in the impurities level occur in small periods of time, they are likely to go beyond a maximum acceptable impurity level. So, large spectral collection times are not acceptable. However, large changes in the impurity level require smaller SNR levels than small changes to be detected; that translates into less scanning time, since it requires fewer scans per sample.

By using an alternating collection of samples and backgrounds, a continuous "stream" of single scan spectra flows from the spectrometer to the computer; which the computer then adds together to produce a spectra that is the average of x scans. But since the computer is receiving all the scans, these scans are stored to produce a running average of x scans for every successive scan. Once x+1 scans have been collected, the first scan is erased and the x+1 scan incorporated into the averaged spectra. Subsequently, a chemometrics process is applied to the newly averaged data.

The chemometrics generate an average concentration of the impurities over a t period of time; t is the time required to generate x number scans per sample spectra, but generated, due to the running average procedure, at every scan. Hence, small changes in impurity levels can be observed. In addition, by comparing and analyzing the latest concentration estimation and the previous concentration estimation, it is possible to observe rapid changes in concentration levels of the impurities for each scan.

Therefore, Equations 46 and 47 are redefined to calculate the running average of x scans per spectra, as follows:

$$B_i = \gamma + \frac{\sum_{j=1}^{x} \varepsilon_{i-2j+2}}{x} + \frac{\sum_{j=2}^{2x-1} \Delta D_{i-j+2}}{2x-2} \quad \text{for } i = \qquad \text{Equation 52}$$
$$2x-1, 2x+1, 2x+3, 2x+5, \ldots$$

$$S_i = \gamma + \theta + \frac{\sum_{j=2}^{2x} \Delta D_{i-j+2}}{2x-1} + \frac{\sum_{j=2}^{2x} \varepsilon_{i-2j+2}}{x} \quad \text{for } i = \qquad \text{Equation 53}$$
$$2x, 2x+2, 2x+4, 2x+6, \ldots$$

where x is equal to the number of scans to be averaged per spectra (window size), and i represents the i scan coming from the spectrometer. Finally:

$$T_i = \begin{cases} i \text{ is even} & \frac{S_i}{B_{i-1}} \\ i \text{ is odd} & \frac{S_{i-1}}{B_i} \end{cases} \qquad \text{Equation 54}$$

and the absorption spectra based on Equation 54 becomes:

$$A_i = \log_{10}\left(\frac{1}{T_i}\right) \qquad \text{Equation 55}$$

In this way, an absorption spectrum is obtained at every scan of the spectrometer, and its concentration is estimated. This spectrum reflects the estimated average concentration over the time required to collect 2x scans.

By using $A_i$ to calculate the concentration of impurities, one obtains:

$$C_i = Q(A_i) \qquad \text{Equation 56}$$

where Q is a function to calculate the concentration of impurities, and $C_i$ is the estimated concentration of impurities of $A_i$. Finally, one can observe rapid changes in concentration by using:

$$\hat{C}_i = \begin{cases} i = 1 & C_i \\ i > 1 \ i < x & i(C_i - C_{i-1}) + C_{i-1} \\ i \geq x & x(C_i - C_{i-1}) + C_{i-x} \end{cases} \qquad \text{Equation 57}$$

By observing $\hat{C}_i$, big changes in concentration can be monitored. Unfortunately $\hat{C}_i$ also reflects a lot of noise; so small changes in concentration cannot be detected.

However, $\hat{C}_i$ is a good estimator for rapid and big changes in concentration.

System Performance

The following is a description of the critical steps required to obtain an optimal chemometric analysis of the different gas species to be analyzed.

Only the most important steps and results for a successful quantification analysis applied to a prototype system are described below. (The other steps that have been previously discussed or are known to those skilled in the art.) These important steps are the dry-down of the gas cell, the collection of spectra with a stable baseline, the generation of calibration data for the quantification analysis, and finally the detection of impurities.

System Dry-down

Since one of the objects of the invention is the detection of low concentrations of moisture in gases, the initial concentration of moisture inside the gas cell plays a very important role in the quantification analysis. Any moisture adsorbed onto or desorbed from the optical surfaces and the walls inside the gas cell will produce significant changes in the moisture absorption bands. This prevents the true estimation of moisture concentration. Therefore, it is preferable to put the gas cell through a purging cycle, e.g., using ultra-pure dry nitrogen, to bring the moisture inside the cell to a minimum before any gas analysis can be performed. The dry-down of the cell is a slow process since moisture is easily adsorbed by different materials. As an analogy, the inside walls and optics of the gas cell act like a sponge; when they come in the presence of moisture, they start adsorbing it. This moisture adsorbed by walls and optics inside the gas cell may get released back into the gas cell volume. These two effects of adsorption and desorption of moisture by the gas cell may alter the true concentration estimation of moisture in a gas, which is also dependent upon the temperature, pressure, and moisture concentration inside the gas cell.

An effective method to remove the moisture inside the gas cell is by heating the gas cell while purging, e.g., with ultra-dry nitrogen. This produces a faster release of the moisture adsorbed by the walls and optics and prevents moisture from being readsorbed.

System Baseline Stability

The stability and the flatness of the spectrometer baseline play an important role during quantification analysis. The quantification analysis bases its estimation on how well the reference spectra match the sample spectra (curve fitting). Changes into the baseline produce changes in the concentration estimation.

As seen in FIG. 21, the baseline after collection of a long background and sample is not center-lined around the x-axis and is far from being linear.

This deviation of the system baseline can be compensated to a certain degree by changing Equation 32. Equation 32 is based on the assumption that the system baseline is centered around the x-axis and is linear. So, Equation 32 is changed to:

$$A_{jp} = a_p + b_p v_j + \sum_{i=1}^{l} k_{ji} c_i + e_j \quad j = 1, 2, \cdots, n \quad \text{Equation 58}$$

where $a_p$, $b_p$ are the intercept and slope for a linear baseline at peak p and $v_j$ is the frequency. The new baseline assumption of Equation 58 is that the baseline of the system is linear over each absorption peak. Equation 58 provides an improvement on the accuracy of the estimated concentration (see, D. M. Haaland, Private Communication, Spring of '98).

The "SpectraStream" provides an improved system baseline, which is closer to being center-lined around the x-axis and linear than the system baseline collected with traditional methods (see, FIG. 22).

The SpectraStream not only helps to produce a more linear baseline, but it also helps to reduce the problems associated with changes of the impurity levels within the purging gas and from desorption of moisture from the inside walls of the spectrometer.

FIG. 23 shows how the system baseline is affected if the instrument is not purged with at least the manufacturer's prescribed flow rate for the instrument (e.g., with dry-nitrogen). As can be seen, the baseline is corrupted by traces of moisture which may get counted as part of the moisture concentration of the gas being analyzed.

In contrast, FIG. 24 shows how SpectraStream is much less affected by not using the specified purging flow rates recommended by the manufacturer. For example, the manufacturer recommends a minimum flow rate of 2.5 slm dry-nitrogen. FIG. 23 reflects a collection time of 1 hour, with a flow rate of 1 slm; while FIG. 24 reflects a collection time of 7 hours with no purging of the instrument at all.

One important aspect of baseline correction is the baseline distortion produced by gas cell optics and windows. Small imperfections on the mirror surfaces, small differences in the reflectivity of the gold, or differences in infrared absorption by the various windows materials at different light frequencies all produce distortions to the spectrometer baseline.

As mentioned before, there are two methods for baseline collection. The first one uses the gas cell to collect the reference spectra and the sample spectra. The reference spectra are collected without the sample gas present inside the gas cell. This means that the gas cell needs to be completely clean, free of any traceable sample or impurity, especially those being analyzed. Since this method uses the same optical path for its reference and sample spectra, its baseline does not reflect the distortion produced by the gas cell optics.

The second method, which is the preferred method of the invention, collects its reference spectra by removing the gas cell transfer optics and letting the infrared light go straight through the spectrometer sample compartment, without going through the gas cell optics. By using this method, the baseline reflects the imperfections of the optics and the levels of absorption by the gas cell windows, plus the spectrometer drift. SpectraStream can be used to collect the baseline spectra and reduce the effects of spectrometer drift.

At this point, SpectraStream becomes an invaluable tool by collecting the baseline spectra of the gas cell when it has been purged and cleaned. These baseline spectra have a very small amount of distortion due to spectrometer drift. The distortion introduced by the gas cell optics is removed by subtracting the baseline of the gas cell from the sample spectra (see, FIG. 25). Even better, the gas cell base line (FIG. 34) can be curve fit to the sample spectra, producing a good baseline correction, which will improve the quantification analysis (see, FIG. 35).

It is also important to note at this point that the use of SpectraStream helps with the collection of calibration spectra, providing a superior quality over traditional calibration spectra collections. The calibration spectra collected with SpectraStream has a better signal to noise ratio, since the collection time is greatly increased with minimal distortion from spectrometer drift.

Impurity Detection

Two methods based on SpectraStream were previously described to monitor the concentration of impurities. These methods provide two types of estimated concentrations. One is a slow response method with high accuracy for the detection of the overall concentration of impurities over a long period of time. The other one is a fast response method with a lower accuracy than the first method; but it reflects fast and large changes in impurity concentration in the gas being analyzed.

The first method that estimates concentrations with high accuracy offers a good tracking of the level of impurities concentration when the monitored gas lines or gas distribution system are somewhat stable—changes of concentration occur slowly over time. This provides a way to visualize if a production process is working over the specified operational range.

The second method tracks the system when its dynamics are changing fast; this allows one to trigger alarms earlier if impurities are going beyond the working acceptable range.

FIG. 26 illustrates a system going from a stable to an unstable working condition. The slow response method shows how the concentration was stable around 50 ppb, but that it suddenly started to increase. Traditionally, it would be hard to tell by how much the concentration has shifted up; as one would be in a blind spot. The fast response method of the present invention clears this blind spot. Despite the fact that the fast response method is not as accurate as the slow response method, it shows that the concentration shifted from 50 ppb to upwards around 1000 ppb. Both methods, together, give one a clearer picture of the impurity dynamics of the system.

EXAMPLE 1

An MB-100 FTIR Spectrometer from ABB Bomem was selected. This is a ruggedized spectrometer designed for industrial use. This spectrometer offered a direct communication interface so that the computer interacted with it for the collection of spectra and to verify the status of the spectrometer. By comparing the actual readings against the original readings of the instrument when it was first new, any degradation of the infrared source and the detector was ascertained. A Watlow Series 96 temperature controller with an RS-232 serial communication port was used. Through this port the temperature controller was accessed and controlled by the computer. It offered a robust communication protocol with error detection and state variables to monitor the status of the controller. A 4Runner gas cell from CIC Photonics of Albuquerque, New Mexico, was selected for our system since it was specifically designed to handle corrosive gases. This gas cell offered a 4-meter pathlength and a low 0.6-liter volume. The 4-meter pathlength allowed the detection of moisture impurities at ppb concentration levels. A Keithley's Metrabyte PIO-24 digital I/O card was selected since it is very simple to use and to control. The PIO-24 digital I/O card uses four locations in I/O space to control the card (see Table 12). This card emulates the 8255 PPI Control Word Mode 0. On power up or whenever the PC bus RESET line is asserted, all ports are initially set up in the Input mode.

TABLE 12

PIO-24 I/O Address Map

| Location | Function | Type |
| --- | --- | --- |
| Base Address + 0 | PA Port | Read/Write |
| Base Address + 1 | PB Port | Read/Write |
| Base Address + 2 | PC Port | Read/Write |
| Base Address + 3 | Control | Write Only |

The PA and PB Ports are byte-wide, and the control register sets the direction of all lines within a port. The PC port is used as a byte-wide port, or it can be split into two ports of four bits (nibble wide). The PC0–3 lines are known as PC-lower, and the PC4–7 lines as PC-upper. Direction of the PC upper and lower ports are independently programmable. A MODBUS Remote Terminal Unit (RTU), made by Schneider Automation, Inc., was selected for the temperature controller. For a more detailed review of the MODBUS protocol implementation in WATLOW temperature controllers (OPEN MODBUS/TCP SPECIFICATION, Schneider Automation, Inc. http://www.modicon.com/openmbus/standards/openmbus.htm). A Bomem MB-100 Spectrometer was selected. This spectrometer was designed for industrial application and provided a. robust design. This spectrometer was accessed and controlled through a library of function calls provided by Bomem (see, Bomem Windows NT Acquisition Driver, ABB Bomem Inc., Inv. #: IMZ8442, Rev.: 1–0, November., 1997).

Some alternative embodiments are discussed below. The use of ultra-dry nitrogen and a vacuum generator reduces the dry-down time associated with the gas cell. This produces a vacuum-purging cycle inside the gas cell, which, in some applications, may be more effective than just purging with ultra-dry nitrogen. The use of infrared detectors with higher SNR than the level provided by a DTGS detector, such as a MCT (mercury cadmium telluride) detector, can provide enhancements in the detection of impurities.

EXAMPLE 2

A manual manifold version of the one presented in FIG. 4 was used to perform the impurity detection analysis: An MB100 FTIR spectrometer with a DTGS (Deuterated Triglycine Sulphate) detector was used. A DTGS detector, compared to other type of detectors, is a slow response detector; the speed of the movable mirrors is only 0.4 cm/s. This detector is capable of running at room temperature. The instrument resolution was set to 2 $cm^{-1}$. This instrument configuration produces a sample spectrum every 11 seconds.

The gas cell used was a CIC Photonics' (Albuquerque, N. Mex.) 4Runner; the sample gas flow rate was set to 1 slpm. Ultra-pure dry nitrogen (impurities less that 1 ppb) was used for purging the spectrometer, gas cell, and purge box with transfer optics. The complete system was purged for 24 hours prior to the quantification analysis.

Only methane, carbon dioxide, carbon monoxide, and moisture levels were monitored from two gas tanks filled up with argon or nitrogen as the diluent gases.

The concentrations of impurities in the nitrogen gas tank were measured as shown in Table 13.

TABLE 13

Measured Concentrations of Impurities in Nitrogen

| Molecule | Concentration (ppb) |
| --- | --- |
| $CH_4$ | 20 |
| CO | 480 |
| $CO_2$ | 1 |
| $H_2O$ | 350 |

The concentrations of impurities in the argon gas tank were measured as shown in Table 14.

TABLE 14

Measured Concentrations of Impurities in Argon

| Molecule | Concentration (ppb) |
| --- | --- |
| $CH_4$ | 1100 |
| CO | 50 |
| $CO_2$ | 400 |
| $H_2O$ | 9000 |

Based upon the previous described experimental setup, the impurities of the nitrogen gas tank were monitored for a period of time; then the sample gas tank was changed from nitrogen to argon. The effects of this change are reflected in FIGS. 27 through 30.

It can be observed in FIG. 27 that the change in the concentration of methane as an impurity, once the gas tank was switched, did not occur immediately. This delay of seconds was due to the time required for the gas to travel through the gas pipelines to reach the gas cell. Once the gas reached the gas cell, it mixed with the gas inside and caused the observed change in concentration.

As can be observed in FIG. 28 and FIG. 30, the sharper the change in concentration of the impurity being monitored the easier it is for the fast response detection method to be effective. The drastic effects that moisture and carbon dioxide had on the quantification analysis at the time of switching tanks should be noticed; the exposure of the internal part of pipeline system to air during the switching of gas tanks introduced a large amount of these two molecular species. This effect is more difficult to be observed with methane and carbon monoxide due to their low concentration relative to moisture and carbon dioxide.

FIG. 30 shows the behavior of moisture in the air surrounding the gas manifold system and gas cell. The system was first exposed to a low concentration of moisture (350 ppb) from the nitrogen gas tank; then this gas tank was changed and the concentration of moisture suddenly increased to a high concentration (9000 ppb). The concentration peak at 14000 ppb was due to moisture present in the atmospheric air around the manifold system when the gas tank was changed. Nevertheless, the more important effect to be observed is that the measured moisture concentration went down first from 14,000 ppb to 8000 ppb and then from 8000 ppb up to 9000 ppb.

The moisture dropped below the 9000 ppb because it is easily adsorbed on the inside walls of the manifold system and gas cell; this adsorption process continues until a steady state point is reached between the internal walls of the gas manifold system and the concentration of moisture in the flowing gas.

The main factors determining the detection limits for the impurities is the signal to noise ratios of the absorption bands for each molecular species: Different molecules, even at the same concentrations, do not absorb infrared radiation with the same intensity. Each molecular species has a distinctive molecular absorption coefficient.

FIG. 31 shows that carbon dioxide has the strongest SNR level, moisture, and the lowest SNR level with respect to the other molecules. It also shows that by increasing the number of scans, the standard error of the quantification analysis is reduced.

FIG. 32 indicates that the SNR level of methane is greater than the SNR of carbon monoxide. However, the SNR level of carbon monoxide is slightly lower than that of methane. The difference arises from the concentration level of these molecules. Moisture and carbon monoxide are not able to generate a standard error below 15 ppb, because the calibration spectra are not an exact match to the spectra collected at that concentration. Any deviation between the calibration spectra and the sample spectra is reflected as an increase in the standard error. These deviations are directly proportional to the concentration of the molecule being analyzed. Therefore, if one analyzes a lower concentration of moisture and carbon monoxide, a lower standard error is obtained in the quantification analysis of these molecules.

FIGS. 32 and 33 compare the standard method of collecting spectra against the SpectraStream method of the present invention. It can be seen that the collection of additional scans per spectrum does not always improve the standard method. This is because of the unpredictable effects of the spectrometer drift. Using the SpectraStream method to reduce the effects of spectrometer drift, the drift is less pronounced.

The invention provides an integrated, automated, controlled, and synchronized hardware system capable of producing an optimal quantification analysis in real-time. The testing of the complete integral system has shown that the weighted multi-band CLS quantification analysis applied to the spectra collected by the system—which offers a higher SNR, reduced the effects of spectrometer drift and removed spectral artifacts introduced by the system optics and it is capable of producing a limit of detection for gas impurities of at least 10–25 ppb/v at every spectral scan of the spectrometer.

FIG. 34 shows a simulated quantification analysis of the SpectraStream processing when applied to a critical chemical impurity in a gas stream being monitored with a FTIR spectrometer in combination with a long path gas cell. The simulation is for an impurity whose acceptable concentration level is 50 ppb, but which becomes a process problem if the concentration exceeds, as an example, 400 ppb. In this illustration, a fairly standard scan set of k=128 scans is assumed. The contribution of each current single scan to the quantification is shown as "normal noise" for the first 200 units of time; At that time point, however, the next single scan jumps to 400 ppb and above, whereas the value of the 128-scan average barely changes. Hence, significant time passes after the actual perturbation of the gas stream purity before it is detectable. This time interval typically last s 10 to 15 minutes minimum before the process engineer recognizes that a systematic process change has occurred. At the point that a correction is applied, the single scan data points respond instantly, but the k-scan sets continue to reflect the averaging of the perturbed concentration level. Only after another significant time period passes does the averaged data return to a level reflecting the actual concentration of the 2impurity. Once again, the correction is immediately displayed by the single scan data points.

As illustrated, this invention overlays the single scan data of a spectral scan onto the averaged data of multiple scans from a scanning spectrometer and presents an output display and detection capability with a time resolution equal to the time between single scans. Using a FTIR spectrometer as an example of a chemical process monitoring instrument, the time resolution for averaged data of several minutes or more is enhanced by 10-to-100-fold to seconds.

The methods created for this invention, and modifications thereof, may be adapted to any spectral analysis system which relies upon spectral scans for the identification, qualification, quantification, and time resolution of physical or chemical phenomena. All scanning spectrometers encompassing spectra from x-rays to microwaves are applicable. The best time resolution is the minimum single scan period of the spectrometer, although multiple scans may be used. Hence, this invention is applicable to all existing and future spectral scanning instruments.

What is claimed is:

1. A system for detection of impurities in gases, the system comprising:
   a Fourier transform infrared spectrometer; and
   means for computation comprising:
      means for system control computation;
      means for spectral analysis computation; and
      means for chemometrics computation employing a running average of estimated impurity levels from a plurality of scans; and
   wherein said system control computation means and said spectral analysis computation means reduce spectrometer drift and perturbations from molecular background absorption by alternating scans between background spectra and sample spectra, which in conjuction with said chemometrics computation means increases signal-to-noise ratio.

2. The system of claim 1 additionally comprising a detector operating at approximately room temperature, said system having a limit of detection of gas impurities of between approximately 10–25 ppb/v.

3. The system of claim 1 wherein said system control computation means comprises gas flow control means controlling gas flow through a gas manifold.

4. The system of claim 1 wherein said system control computation means comprises temperature control means for control of moisture buildup.

5. The system of claim 1 wherein said system control computation means comprises means for adjusting a transfer mirror.

6. The system of claim 1 wherein said chemometrics computation means computes an average concentration of an impurity at every scan.

7. The system of claim 6 wherein said chemometrics computation means is responsive to changes in impurity concentrations occurring from both scan to scan and over said plurality of scans.

8. The system of claim 1 wherein said chemometrics computation means assumes that a system baseline is not necessarily centered around an x-axis of collected spectra so as to reduce errors resulting from baseline drift.

9. A method for detection of impurities in gases, the method comprising the steps of:
   providing a Fourier transform infrared spectrometer; and
   employing a means for computation comprising:
      employing means for system control computation;
      performing spectral analysis using means for spectral analysis computation; and
      performing chemometrics analysis employing a running average of estimated impurity levels from a plurality of scans using means for chemometrics computation; and
   wherein employing system control computation means and performing spectral analysis comprise reducing spectrometer drift and perturbations from molecular background absorption by alternating scans between background spectra and sample spectra, which in conjunction with the chemometrics analysis step increases signal-to-noise ratio.

10. The method of claim 1 additionally comprising employing a detector operating at approximately room temperature and establishing a limit of detection of gas impurities of between approximately 10–25 ppb/v.

11. The method of claim 9 wherein employing system control computation means comprises controlling gas flow through a gas manifold using gas flow control means.

12. The method of claim 9 wherein employing system control computation means comprises controlling moisture buildup employing temperature control means.

13. The method of claim 9 wherein employing system control computation means comprises adjusting a transfer mirror.

14. The method of claim 9 wherein performing chemometrics analysis comprises computing an average concentration of an impurity at every scan.

15. The method of claim 14 wherein performing chemometrics analysis comprises reporting changes in impurity concentrations occurring from both scan to scan and over the plurality of scans.

16. The method of claim 9 wherein the step of performing the chemometrics analysis assumes that a system baseline is not necessarily centered around an x-axis of collected spectra so as to reduce errors resulting from baseline drift.

17. A system for detection of impurities in gases, the system comprising:
   a Fourier transform infrared spectrometer;
   means for computation comprising:
      means for system control computation;
      means for spectral analysis computation; and
      means for chemometrics computation employing a running average of estimated impurity levels from a plurality of scans; and
   a detector operating at approximately room temperature, said system having a limit of detection of gas impurities of between approximately 10–25 ppb/v.

18. A system for detection of impurities in gases, the system comprising:
   a Fourier transform infrared spectrometer; and
   means for computation comprising:
      means for system control computation;
      means for spectral analysis computation; and
      means for chemometrics computation employing a running average of estimated impurity levels from a plurality of scans; and wherein said system control computation means comprises temperature control means for control of moisture buildup.

19. A system for detection of impurities in gases, the system comprising:
   a Fourier transform infrared spectrometer; and
   means for computation comprising:
      means for system control computation;
      means for spectral analysis computation; and
      means for chemometrics computation employing a running average of estimated impurity levels from a plurality of scans; and
   wherein said chemometrics computation means computes an average concentration of an impurity at every scan.

20. A method for detection of impurities in gases, the method comprising the steps of:
   providing a Fourier transform infrared spectrometer;
   employing a means for computation comprising:
      employing means for system control computation;
      performing spectral analysis using means for spectral analysis computation; and
      performing chemometrics analysis employing a running average of estimated impurity levels from a plurality of scans using means for chemometrics computation; and
   employing a detector operating at approximately room temperature and establishing a limit of detection of gas impurities of between approximately 10–25 ppb/v.

21. A method for detection of impurities in gases, the method comprising the steps of:
   providing a Fourier transform infrared spectrometer; and
   employing a means for computation comprising:
      employing means for system control computation;
      performing spectral analysis using means for spectral analysis computation; and
      performing chemometrics analysis employing a running average of estimated impurity levels from a plurality of scans using means for chemometrics computation; and
   wherein employing system control computation means comprises controlling moisture buildup employing temperature control means.

22. A method for detection of impurities in gases, the method comprising the steps of:
   providing a Fourier transform infrared spectrometer; and
   employing a means for computation comprising:
      employing means for system control computation;
      performing spectral analysis using means for spectral analysis computation; and
      performing chemometrics analysis employing a running average of estimated impurity levels from a plurality of scans using means for chemometrics computation; and
   wherein performing chemometrics analysis comprises computing an average concentration of an impurity at every scan.

* * * * *